US012673224B2

(12) United States Patent
Sverdlik et al.

(10) Patent No.: US 12,673,224 B2
(45) Date of Patent: Jul. 7, 2026

(54) DEVICES AND METHODS FOR PULMONARY HYPERTENSION TREATMENT

(71) Applicant: Sonivie Ltd., Rosh HaAyin (IL)

(72) Inventors: Ariel Sverdlik, Tel-Aviv (IL); Or Shabtay, Kibbutz Farod (IL); Lilah Marziano, Ganei-Tikva (IL)

(73) Assignee: SONIVIE LTD., Rosh Haayin (IL)

( * ) Notice: Subject to any disclaimer, the term of this patent is extended or adjusted under 35 U.S.C. 154(b) by 1241 days.

(21) Appl. No.: 16/540,191

(22) Filed: Aug. 14, 2019

(65) Prior Publication Data

US 2019/0366130 A1 Dec. 5, 2019

Related U.S. Application Data

(62) Division of application No. 15/529,137, filed as application No. PCT/IL2015/051145 on Nov. 25, 2015, now abandoned.

(Continued)

(51) Int. Cl.
A61N 7/02 (2006.01)
A61B 18/00 (2006.01)
A61N 7/00 (2006.01)

(52) U.S. Cl.
CPC ................. *A61N 7/02* (2013.01); *A61N 7/00* (2013.01); *A61N 7/022* (2013.01);
(Continued)

(58) Field of Classification Search
CPC . A61N 7/02; A61N 7/022; A61N 7/00; A61N 2007/003; A61N 2007/0043;
(Continued)

(56) References Cited

U.S. PATENT DOCUMENTS

| 4,319,580 A | 3/1982 | Colley et al. |
| 5,038,789 A | 8/1991 | Frazin |

(Continued)

FOREIGN PATENT DOCUMENTS

| CA | 2954897 | 11/2016 |
| CN | 1279595 | 1/2001 |

(Continued)

OTHER PUBLICATIONS

Advisory Action Before the Filing of An Appeal Brief Dated Feb. 4, 2019 From the US Patent and Trademark Office Re. U.S. Appl. No. 14/190,113. (6 pages).

(Continued)

*Primary Examiner* — Boniface N Nganga
(74) *Attorney, Agent, or Firm* — Seager, Tufte & Wickhem, LLP

(57) ABSTRACT

The present invention in some embodiments thereof relates to a method for selectively modifying nerve activity without causing substantial damage to non-targeted tissue, comprising introducing a catheter device comprising one or more ultrasonic transceivers to the pulmonary artery lumen, receiving, using the one or more ultrasonic transceivers, echo signals reflected from the non-targeted tissue following emission of ultrasound energy by the one or more transceivers, analyzing the received echo signals to identify at least one of a type and location of the non-targeted tissue relative to the one or more transceivers, and emitting ultrasound energy from the one or more ultrasonic transceivers in accordance with the analysis, to modify nerve activity without substantially damaging the identified non-targeted tissue.

22 Claims, 23 Drawing Sheets
(16 of 23 Drawing Sheet(s) Filed in Color)

Related U.S. Application Data

(60) Provisional application No. 62/084,782, filed on Nov. 26, 2014.

(52) U.S. Cl.
CPC .............. *A61B 2018/00023* (2013.01); *A61B 2018/0022* (2013.01); *A61B 2018/00255* (2013.01); *A61B 2018/00267* (2013.01); *A61B 2018/00351* (2013.01); *A61B 2018/00375* (2013.01); *A61B 2018/00404* (2013.01); *A61B 2018/00434* (2013.01); *A61B 2018/00541* (2013.01); *A61B 2018/00577* (2013.01); *A61B 2018/00642* (2013.01); *A61B 2018/00708* (2013.01); *A61B 2018/00732* (2013.01); *A61B 2018/00761* (2013.01); *A61B 2018/00791* (2013.01); *A61B 2018/00863* (2013.01); *A61N 2007/003* (2013.01); *A61N 2007/0043* (2013.01); *A61N 2007/0052* (2013.01); *A61N 2007/0078* (2013.01)

(58) Field of Classification Search
CPC .... A61N 2007/0052; A61N 2007/0078; A61B 2018/0022; A61B 2018/00023; A61B 2018/00255; A61B 2018/00267; A61B 2018/00351; A61B 2018/22404; A61B 2018/00434; A61B 2018/00541; A61B 2018/00577; A61B 2018/00642; A61B 2018/00708; A61B 2018/00732; A61B 2018/00761; A61B 2018/00791; A61B 2018/00863

See application file for complete search history.

(56) References Cited

U.S. PATENT DOCUMENTS

| | | | |
|---|---|---|---|
| 5,226,847 A | 7/1993 | Thomas, III et al. |
| 5,421,338 A | 6/1995 | Crowley et al. |
| 5,467,251 A | 11/1995 | Katchmar |
| 5,471,988 A | 12/1995 | Fujio et al. |
| 5,494,039 A | 2/1996 | Onik et al. |
| 5,524,630 A | 6/1996 | Crowley |
| 5,590,653 A | 1/1997 | Aida et al. |
| 5,620,417 A | 4/1997 | Jang et al. |
| 5,620,479 A | 4/1997 | Diederich |
| 5,657,760 A | 8/1997 | Ying et al. |
| 5,699,804 A | 12/1997 | Rattner |
| 5,707,367 A | 1/1998 | Nilsson |
| 5,735,280 A | 4/1998 | Sherman et al. |
| 5,762,066 A | 6/1998 | Law et al. |
| 5,772,642 A | 6/1998 | Ciamacco, Jr. et al. |
| 5,895,355 A | 4/1999 | Schaer |
| 5,895,356 A | 4/1999 | Andrus et al. |
| 5,971,949 A | 10/1999 | Levin et al. |
| 6,007,499 A | 12/1999 | Martin et al. |
| 6,042,556 A | 3/2000 | Beach et al. |
| 6,073,048 A | 6/2000 | Kieval et al. |
| 6,077,225 A | 6/2000 | Brock-Fisher |
| 6,117,101 A | 9/2000 | Diederich et al. |
| 6,119,041 A | 9/2000 | Pomeranz et al. |
| 6,120,442 A | 9/2000 | Hickey |
| 6,165,127 A | 12/2000 | Crowley |
| 6,210,393 B1 | 4/2001 | Brisken |
| 6,216,041 B1 | 4/2001 | Tierney et al. |
| 6,235,024 B1 | 5/2001 | Tu |
| 6,261,233 B1 | 7/2001 | Kantorovich |
| 6,296,619 B1 | 10/2001 | Brisken et al. |
| 6,379,320 B1 | 4/2002 | Lafon et al. |
| 6,428,477 B1 | 8/2002 | Mason |
| 6,451,013 B1 | 9/2002 | Bays et al. |
| 6,500,121 B1 | 12/2002 | Slayton et al. |
| 6,511,428 B1 | 1/2003 | Azuma et al. |
| 6,511,436 B1 | 1/2003 | Asmar |
| 6,514,249 B1 | 2/2003 | Maguire et al. |
| 6,524,271 B2 | 2/2003 | Brisken et al. |
| 6,527,759 B1 | 3/2003 | Tachibana et al. |
| 6,547,788 B1 | 4/2003 | Maguire et al. |
| 6,575,906 B1 | 6/2003 | Schembri, Jr. et al. |
| 6,599,288 B2 | 7/2003 | Maguire et al. |
| 6,607,502 B1 | 8/2003 | Maguire et al. |
| 6,623,687 B1 | 9/2003 | Gervasi et al. |
| 6,645,147 B1 | 11/2003 | Jackson et al. |
| 6,740,040 B1 | 5/2004 | Mandrusov et al. |
| 6,752,805 B2 | 6/2004 | Maguire et al. |
| 6,953,460 B2 | 10/2005 | Maguire et al. |
| 6,955,173 B2 | 10/2005 | Lesh |
| 6,978,174 B2 | 12/2005 | Gelfand et al. |
| 7,001,336 B2 | 2/2006 | Mandrusov et al. |
| 7,037,271 B2 | 5/2006 | Crowley |
| 7,084,004 B2 | 8/2006 | Vaiyapuri et al. |
| 7,156,816 B2 | 1/2007 | Schwartz et al. |
| 7,162,303 B2 | 1/2007 | Levin et al. |
| 7,166,098 B1 | 1/2007 | Steward et al. |
| 7,220,233 B2 | 5/2007 | Nita et al. |
| 7,220,258 B2 | 5/2007 | Myhr |
| 7,220,261 B2 | 5/2007 | Truckai et al. |
| 7,285,116 B2 | 10/2007 | De la Rama et al. |
| 7,326,201 B2 | 2/2008 | Fjield et al. |
| 7,341,583 B2 | 3/2008 | Shiono et al. |
| 7,344,529 B2 | 3/2008 | Torchia et al. |
| 7,347,859 B2 | 3/2008 | Garabedian et al. |
| 7,410,486 B2 | 8/2008 | Fuimaono et al. |
| 7,460,369 B1 | 12/2008 | Blish, II |
| 7,470,241 B2 | 12/2008 | Weng et al. |
| 7,479,106 B2 | 1/2009 | Banik et al. |
| 7,510,536 B2 | 3/2009 | Foley et al. |
| 7,538,425 B2 | 5/2009 | Myers et al. |
| RE40,815 E | 6/2009 | Kudaravalli et al. |
| 7,540,846 B2 | 6/2009 | Harhen et al. |
| 7,540,870 B2 | 6/2009 | Babaev |
| 7,563,260 B2 | 7/2009 | Whitmore et al. |
| 7,617,005 B2 | 11/2009 | Demarais et al. |
| 7,620,451 B2 | 11/2009 | Demarais et al. |
| 7,621,929 B2 | 11/2009 | Nita et al. |
| 7,647,115 B2 | 1/2010 | Levin et al. |
| 7,653,438 B2 | 1/2010 | Deem et al. |
| 7,655,005 B2 | 2/2010 | Bhola |
| 7,678,104 B2 | 3/2010 | Keidar |
| 7,704,212 B2 | 4/2010 | Wekell et al. |
| 7,713,210 B2 | 5/2010 | Byrd et al. |
| 7,717,948 B2 | 5/2010 | Demarais et al. |
| 7,727,228 B2 | 6/2010 | Abboud et al. |
| 7,736,317 B2 | 6/2010 | Stephens et al. |
| 7,756,583 B2 | 7/2010 | Demarais et al. |
| 7,762,954 B2 | 7/2010 | Nix et al. |
| 7,771,372 B2 | 8/2010 | Wilson |
| 7,819,826 B2 | 10/2010 | Diederich et al. |
| 7,819,868 B2 | 10/2010 | Cao et al. |
| 7,824,348 B2 | 11/2010 | Barthe et al. |
| 7,850,683 B2 | 12/2010 | Elkins et al. |
| 7,850,685 B2 | 12/2010 | Kunis et al. |
| 7,853,333 B2 | 12/2010 | Demarais |
| 7,854,733 B2 | 12/2010 | Govari |
| 7,883,506 B2 | 2/2011 | McIntyre et al. |
| 7,940,969 B2 | 5/2011 | Nair et al. |
| 8,216,216 B2 | 7/2012 | Warnking et al. |
| 8,221,402 B2 | 7/2012 | Francischelli et al. |
| 8,401,667 B2 | 3/2013 | Gustus et al. |
| 8,419,729 B2 | 4/2013 | Ibrahim et al. |
| 8,540,662 B2 | 9/2013 | Stehr et al. |
| 8,568,403 B2 | 10/2013 | Soltesz et al. |
| 8,585,695 B2 | 11/2013 | Shih |
| 8,715,209 B2 | 5/2014 | Gertner |
| 8,974,446 B2 | 3/2015 | Nguyen et al. |
| 10,368,893 B2 | 8/2019 | Sverdlik et al. |
| 11,318,331 B2 | 5/2022 | Shabtay |
| 2001/0007940 A1 | 7/2001 | Tu et al. |
| 2001/0014780 A1 | 8/2001 | Martin et al. |
| 2001/0053885 A1 | 12/2001 | Gielen et al. |
| 2002/0002371 A1 | 1/2002 | Acker et al. |
| 2002/0016624 A1 | 2/2002 | Patterson et al. |
| 2002/0019627 A1 | 2/2002 | Maguire et al. |

(56) References Cited

U.S. PATENT DOCUMENTS

| | | | |
|---|---|---|---|
| 2002/0022833 A1 | 2/2002 | Maguire et al. |
| 2002/0026127 A1 | 2/2002 | Balbierz et al. |
| 2002/0048310 A1 | 4/2002 | Heuser |
| 2002/0055754 A1 | 5/2002 | Ranucci et al. |
| 2002/0065512 A1 | 5/2002 | Fjield et al. |
| 2002/0077643 A1 | 6/2002 | Rabiner et al. |
| 2002/0169394 A1 | 11/2002 | Eppstein et al. |
| 2002/0188218 A1 | 12/2002 | Lipman |
| 2003/0013968 A1 | 1/2003 | Fjield et al. |
| 2003/0092667 A1 | 5/2003 | Tachibana et al. |
| 2003/0125726 A1 | 7/2003 | Maguire et al. |
| 2003/0135115 A1 | 7/2003 | Burdette et al. |
| 2003/0151417 A1 | 8/2003 | Koen |
| 2003/0153850 A1 | 8/2003 | Davis et al. |
| 2003/0158545 A1* | 8/2003 | Hovda .................. A61B 18/148 |
| | | 606/49 |
| 2003/0163190 A1 | 8/2003 | LaFont et al. |
| 2003/0181901 A1 | 9/2003 | Maguire et al. |
| 2003/0195496 A1 | 10/2003 | Maguire et al. |
| 2003/0199747 A1 | 10/2003 | Michlitsch et al. |
| 2003/0199768 A1 | 10/2003 | Cespededs et al. |
| 2004/0006333 A1 | 1/2004 | Arnold et al. |
| 2004/0019687 A1 | 1/2004 | Ozawa et al. |
| 2004/0073660 A1 | 4/2004 | Toomey |
| 2004/0082859 A1 | 4/2004 | Schaer |
| 2004/0102361 A1 | 5/2004 | Bodin |
| 2004/0102769 A1 | 5/2004 | Schwartz et al. |
| 2004/0143358 A1 | 7/2004 | Silverbrook |
| 2004/0162458 A1 | 8/2004 | Green et al. |
| 2005/0015079 A1 | 1/2005 | Keider |
| 2005/0020967 A1 | 1/2005 | Ono |
| 2005/0096542 A1 | 5/2005 | Weng et al. |
| 2005/0096647 A1 | 5/2005 | Steinke et al. |
| 2005/0159676 A1 | 7/2005 | Taylor et al. |
| 2005/0215946 A1 | 9/2005 | Hansmann et al. |
| 2005/0240124 A1 | 10/2005 | Mast |
| 2005/0240170 A1 | 10/2005 | Zhang et al. |
| 2005/0288730 A1 | 12/2005 | Deem et al. |
| 2006/0009753 A1 | 1/2006 | Fjield et al. |
| 2006/0052774 A1 | 3/2006 | Garrison et al. |
| 2006/0058711 A1 | 3/2006 | Harhen et al. |
| 2006/0079816 A1 | 4/2006 | Barthe et al. |
| 2006/0084966 A1 | 4/2006 | Maguire et al. |
| 2006/0173387 A1 | 8/2006 | Hansmann et al. |
| 2006/0229594 A1 | 10/2006 | Francischelli et al. |
| 2006/0241442 A1 | 10/2006 | Barthe et al. |
| 2006/0241739 A1 | 10/2006 | Besselink et al. |
| 2006/0264809 A1 | 11/2006 | Hansmann et al. |
| 2006/0287604 A1 | 12/2006 | Hickey |
| 2007/0043291 A1 | 2/2007 | Fidel |
| 2007/0043297 A1 | 2/2007 | Miyazawa |
| 2007/0088346 A1 | 4/2007 | Mirizzi et al. |
| 2007/0142831 A1 | 6/2007 | Shadduck |
| 2007/0142879 A1 | 6/2007 | Greenberg et al. |
| 2007/0167824 A1 | 7/2007 | Lee et al. |
| 2007/0203479 A1 | 8/2007 | Auth et al. |
| 2007/0222339 A1 | 9/2007 | Lukacs et al. |
| 2007/0225619 A1 | 9/2007 | Rabiner et al. |
| 2007/0233057 A1 | 10/2007 | Konishi |
| 2007/0249997 A1 | 10/2007 | Goodson, IV et al. |
| 2007/0282407 A1 | 12/2007 | Demarais et al. |
| 2008/0004481 A1 | 1/2008 | Bax et al. |
| 2008/0039745 A1 | 2/2008 | Babaev |
| 2008/0077202 A1 | 3/2008 | Levinson |
| 2008/0086073 A1 | 4/2008 | McDaniel |
| 2008/0114354 A1 | 5/2008 | Whayne et al. |
| 2008/0125829 A1 | 5/2008 | Velasco et al. |
| 2008/0139971 A1 | 6/2008 | Lockhart |
| 2008/0146924 A1 | 6/2008 | Smith et al. |
| 2008/0171934 A1 | 7/2008 | Greenan et al. |
| 2008/0179736 A1 | 7/2008 | Hartwell et al. |
| 2008/0183110 A1 | 7/2008 | Davenport et al. |
| 2008/0195000 A1 | 8/2008 | Spooner et al. |
| 2008/0213331 A1 | 9/2008 | Gelfand et al. |
| 2008/0214966 A1 | 9/2008 | Slayton et al. |
| 2008/0215039 A1 | 9/2008 | Slatkine et al. |
| 2008/0228111 A1 | 9/2008 | Nita |
| 2008/0249518 A1 | 10/2008 | Warnking et al. |
| 2008/0281297 A1 | 11/2008 | Pesach et al. |
| 2008/0300571 A1 | 12/2008 | LePivert |
| 2008/0300655 A1 | 12/2008 | Cholette |
| 2008/0312643 A1 | 12/2008 | Kania et al. |
| 2009/0018446 A1 | 1/2009 | Medan et al. |
| 2009/0030339 A1 | 1/2009 | Cheng et al. |
| 2009/0036914 A1 | 2/2009 | Houser |
| 2009/0093737 A1 | 4/2009 | Chomas et al. |
| 2009/0131930 A1 | 5/2009 | Gelbart et al. |
| 2009/0149782 A1 | 6/2009 | Cohen et al. |
| 2009/0163807 A1 | 6/2009 | Sliwa |
| 2009/0216246 A1 | 8/2009 | Nita et al. |
| 2009/0221939 A1 | 9/2009 | Demarais et al. |
| 2009/0221955 A1 | 9/2009 | Babaev |
| 2009/0254078 A1 | 10/2009 | Just et al. |
| 2009/0281478 A1 | 11/2009 | Duke |
| 2009/0299360 A1 | 12/2009 | Ormsby |
| 2010/0036293 A1 | 2/2010 | Isola et al. |
| 2010/0081933 A1 | 4/2010 | Sverdlik et al. |
| 2010/0091112 A1 | 4/2010 | Veeser et al. |
| 2010/0114082 A1 | 5/2010 | Sharma |
| 2010/0125198 A1 | 5/2010 | Thapliyal et al. |
| 2010/0130892 A1 | 5/2010 | Warnking |
| 2010/0137860 A1 | 6/2010 | Demarais et al. |
| 2010/0152625 A1 | 6/2010 | Milo |
| 2010/0168624 A1 | 7/2010 | Sliwa |
| 2010/0168649 A1 | 7/2010 | Schwartz et al. |
| 2010/0168731 A1 | 7/2010 | Wu et al. |
| 2010/0185156 A1 | 7/2010 | Kanner et al. |
| 2010/0191112 A1 | 7/2010 | Demarais et al. |
| 2010/0198040 A1 | 8/2010 | Friedman et al. |
| 2010/0210946 A1 | 8/2010 | Harada et al. |
| 2010/0222851 A1 | 9/2010 | Deem et al. |
| 2010/0228162 A1 | 9/2010 | Sliwa et al. |
| 2010/0262014 A1 | 10/2010 | Huang |
| 2010/0331686 A1 | 12/2010 | Hossack et al. |
| 2010/0331950 A1 | 12/2010 | Strommer |
| 2011/0009779 A1 | 1/2011 | Romano et al. |
| 2011/0028962 A1 | 2/2011 | Werneth et al. |
| 2011/0034809 A1 | 2/2011 | Eberle et al. |
| 2011/0066217 A1 | 3/2011 | Diller et al. |
| 2011/0071380 A1 | 3/2011 | Goldenberg et al. |
| 2011/0092781 A1 | 4/2011 | Gertner |
| 2011/0092880 A1 | 4/2011 | Gertner |
| 2011/0106132 A1 | 5/2011 | Barbut et al. |
| 2011/0112400 A1 | 5/2011 | Emery et al. |
| 2011/0178441 A1 | 7/2011 | Tyler |
| 2011/0201973 A1 | 8/2011 | Stephens et al. |
| 2011/0257563 A1 | 10/2011 | Thapliyal et al. |
| 2011/0264075 A1 | 10/2011 | Leung et al. |
| 2011/0264086 A1 | 10/2011 | Ingle |
| 2011/0270247 A1 | 11/2011 | Sherman |
| 2011/0282203 A1 | 11/2011 | Tsoref et al. |
| 2011/0282249 A1 | 11/2011 | Tsoref et al. |
| 2011/0301662 A1 | 12/2011 | Bar-Yoseph et al. |
| 2011/0319759 A1 | 12/2011 | Liu et al. |
| 2011/0319765 A1 | 12/2011 | Gertner et al. |
| 2012/0010512 A1 | 1/2012 | O'Laughlin et al. |
| 2012/0016273 A1 | 1/2012 | Diederich |
| 2012/0053577 A1 | 3/2012 | Lee et al. |
| 2012/0065494 A1 | 3/2012 | Gertner et al. |
| 2012/0083717 A1 | 4/2012 | Alleman et al. |
| 2012/0095335 A1 | 4/2012 | Sverdlik et al. |
| 2012/0095371 A1 | 4/2012 | Sverdlik et al. |
| 2012/0095372 A1 | 4/2012 | Sverdlik et al. |
| 2012/0123243 A1 | 5/2012 | Hastings |
| 2012/0123270 A1 | 5/2012 | Klee et al. |
| 2012/0157841 A1 | 6/2012 | Glaenzer et al. |
| 2012/0203098 A1 | 8/2012 | Raju et al. |
| 2012/0209116 A1 | 8/2012 | Hossack et al. |
| 2012/0215106 A1* | 8/2012 | Sverdlik .............. G01N 29/348 |
| | | 601/2 |
| 2012/0232409 A1 | 9/2012 | Stahmann et al. |
| 2012/0232436 A1 | 9/2012 | Warnking |
| 2012/0245455 A1 | 9/2012 | Bauman et al. |
| 2012/0265227 A1 | 10/2012 | Sverdlik et al. |

(56) References Cited

U.S. PATENT DOCUMENTS

| 2012/0268886 A1 | 10/2012 | Leontiev et al. |
| 2012/0283605 A1 | 11/2012 | Lewis, Jr. |
| 2012/0310233 A1 | 12/2012 | Dimmer et al. |
| 2012/0316559 A1 | 12/2012 | Mayse et al. |
| 2013/0072928 A1 | 3/2013 | Schaer |
| 2013/0123670 A1 | 5/2013 | Smith |
| 2013/0131668 A1 | 5/2013 | Schaer |
| 2013/0197555 A1* | 8/2013 | Schaer .................. A61N 7/022 606/170 |
| 2013/0204068 A1* | 8/2013 | Gnanashanmugam ...................... A61B 18/18 601/3 |
| 2013/0204167 A1 | 8/2013 | Sverdlik et al. |
| 2013/0204242 A1 | 8/2013 | Sverdlik et al. |
| 2013/0207519 A1 | 8/2013 | Chaggares et al. |
| 2013/0211292 A1 | 8/2013 | Sverdlik et al. |
| 2013/0211396 A1 | 8/2013 | Sverdlik et al. |
| 2013/0211437 A1 | 8/2013 | Sverdlik et al. |
| 2013/0218054 A1 | 8/2013 | Sverdlik et al. |
| 2013/0218068 A1 | 8/2013 | Sverdlik et al. |
| 2013/0225595 A1 | 8/2013 | Gillies et al. |
| 2013/0226040 A1 | 8/2013 | Michael et al. |
| 2013/0267875 A1 | 10/2013 | Thapliyal et al. |
| 2013/0274607 A1 | 10/2013 | Anand et al. |
| 2013/0296836 A1 | 11/2013 | Barbut et al. |
| 2013/0310680 A1 | 11/2013 | Werahera et al. |
| 2013/0310822 A1 | 11/2013 | Mayse et al. |
| 2014/0005706 A1 | 1/2014 | Gelfand et al. |
| 2014/0012133 A1 | 1/2014 | Sverdlik et al. |
| 2014/0024975 A1 | 1/2014 | Little et al. |
| 2014/0039286 A1 | 2/2014 | Hoffer |
| 2014/0039314 A1 | 2/2014 | Stoianovici et al. |
| 2014/0039477 A1 | 2/2014 | Sverdlik et al. |
| 2014/0058294 A1 | 2/2014 | Gross et al. |
| 2014/0074076 A1 | 3/2014 | Gertner |
| 2014/0088585 A1 | 3/2014 | Hill et al. |
| 2014/0114215 A1 | 4/2014 | Melder et al. |
| 2014/0163540 A1 | 6/2014 | Iyer et al. |
| 2014/0163652 A1 | 6/2014 | Witzel et al. |
| 2014/0180197 A1 | 6/2014 | Sverdlik et al. |
| 2014/0180277 A1 | 6/2014 | Chen |
| 2014/0194866 A1 | 7/2014 | Wang |
| 2014/0255647 A1 | 9/2014 | Johnson et al. |
| 2014/0257262 A1 | 9/2014 | Carpentier et al. |
| 2014/0276135 A1 | 9/2014 | Agah et al. |
| 2014/0359111 A1 | 12/2014 | Hilmo et al. |
| 2015/0057599 A1 | 2/2015 | Chen |
| 2015/0073400 A1 | 3/2015 | Sverdlik et al. |
| 2015/0112234 A1 | 4/2015 | McCaffrey et al. |
| 2015/0119715 A1 | 4/2015 | Baumann et al. |
| 2015/0150459 A1 | 6/2015 | Werahera et al. |
| 2015/0190660 A1 | 7/2015 | Sarge et al. |
| 2015/0242486 A1 | 8/2015 | Chari et al. |
| 2015/0272668 A1 | 10/2015 | Chen |
| 2015/0366544 A1 | 12/2015 | Yap et al. |
| 2016/0059044 A1 | 3/2016 | Gertner |
| 2016/0059489 A1 | 3/2016 | Wang |
| 2016/0113699 A1 | 4/2016 | Sverdlik et al. |
| 2016/0220851 A1 | 8/2016 | Mayse et al. |
| 2016/0374710 A1 | 12/2016 | Sinelnikov et al. |
| 2017/0027645 A1 | 2/2017 | Ben Oren et al. |
| 2017/0050374 A1 | 2/2017 | Minardi et al. |
| 2017/0120333 A1 | 5/2017 | DeMuth et al. |
| 2017/0246482 A1 | 8/2017 | Hananel et al. |
| 2017/0312021 A1 | 11/2017 | Pilcher et al. |
| 2017/0354461 A1 | 12/2017 | Rothman et al. |
| 2018/0055988 A1 | 3/2018 | Brun |
| 2018/0326227 A1 | 11/2018 | Sverdlik et al. |
| 2018/0353203 A1 | 12/2018 | Lupotti et al. |
| 2019/0290350 A1 | 9/2019 | Sverdlik et al. |
| 2019/0308003 A1 | 10/2019 | Sverdlik et al. |
| 2020/0238107 A1 | 7/2020 | Shabtay et al. |
| 2020/0368244 A1 | 11/2020 | Shabtay et al. |
| 2021/0178194 A1 | 6/2021 | Sverdlik et al. |
| 2022/0241617 A1 | 8/2022 | Shabtay et al. |
| 2022/0287634 A1 | 9/2022 | Sverdlik et al. |
| 2023/0389954 A1 | 12/2023 | Sverdlik et al. |

FOREIGN PATENT DOCUMENTS

| CN | 101610735 | 12/2009 |
| CN | 101820820 | 9/2010 |
| EP | 1384445 | 1/2004 |
| EP | 1424100 | 6/2004 |
| EP | 1799302 | 3/2006 |
| EP | 1769759 | 4/2007 |
| EP | 1802370 | 7/2007 |
| EP | 2092957 | 8/2009 |
| EP | 2218479 | 8/2010 |
| EP | 2455133 | 5/2012 |
| JP | 07-227394 | 8/1995 |
| JP | 09-122139 | 5/1997 |
| JP | 10-248854 | 9/1998 |
| JP | 2008-536562 | 9/2008 |
| JP | 2010-517695 | 5/2010 |
| JP | 2019-018526 | 2/2019 |
| JP | 6650925 | 2/2020 |
| WO | WO 91/10405 | 7/1991 |
| WO | WO 99/16366 | 4/1999 |
| WO | WO 00/67648 | 10/2000 |
| WO | WO 01/45550 | 6/2001 |
| WO | WO 02/096501 | 12/2002 |
| WO | WO 2004/054448 | 7/2004 |
| WO | WO 2006/022790 | 3/2006 |
| WO | WO 2006/041847 | 4/2006 |
| WO | WO 2006/041881 | 4/2006 |
| WO | WO 2006/042163 | 4/2006 |
| WO | WO 2007/001981 | 1/2007 |
| WO | WO 2007/078997 | 7/2007 |
| WO | WO 2007/115307 | 10/2007 |
| WO | WO 2007/127176 | 11/2007 |
| WO | WO 2008/003058 | 1/2008 |
| WO | WO 2008/098101 | 8/2008 |
| WO | WO 2008/102363 | 8/2008 |
| WO | WO 2010/009473 | 1/2010 |
| WO | WO 2010/118307 | 10/2010 |
| WO | WO 2011/053757 | 5/2011 |
| WO | WO 2011/060200 | 5/2011 |
| WO | WO-2011075328 A1 * | 6/2011 | ............. A61B 18/02 |
| WO | WO 2012/052920 | 4/2012 |
| WO | WO 2012/052921 | 4/2012 |
| WO | WO 2012/052922 | 4/2012 |
| WO | WO 2012/052924 | 4/2012 |
| WO | WO 2012/052925 | 4/2012 |
| WO | WO 2012/052926 | 4/2012 |
| WO | WO 2012/052927 | 4/2012 |
| WO | WO-2012052927 A1 * | 4/2012 | ....... A61B 17/22012 |
| WO | WO 2012/061713 | 5/2012 |
| WO | WO 2013/030743 | 3/2013 |
| WO | WO 2013/111136 | 8/2013 |
| WO | WO 2013/134479 | 9/2013 |
| WO | WO 2013/157009 | 10/2013 |
| WO | WO 2013/157011 | 10/2013 |
| WO | WO 2013/162694 | 10/2013 |
| WO | WO 2014/141052 | 9/2014 |
| WO | WO 2014/188430 | 11/2014 |
| WO | WO 2016/084081 | 6/2016 |
| WO | WO 2016/084081 A8 | 6/2017 |
| WO | WO 2018/173052 | 9/2018 |
| WO | WO 2018/173053 | 9/2018 |

OTHER PUBLICATIONS

Advisory Action Dated Jun. 16, 2020 from the US Patent and Trademark Office Re. U.S. Appl. No. 13/449,539. (5 pages).

Applicant-Initiated Interview Summary Dated Apr. 2, 2019 From the US Patent and Trademark Office Re. U.S. Appl. No. 13/905,224. (3 pages).

Applicant-Initiated Interview Summary Dated Jan. 4, 2016 From the US Patent and Trademark Office Re. U.S. Appl. No. 13/449,539.

Applicant-Initiated Interview Summary Dated Jul. 14, 2016 From the US Patent and Trademark Office Re. U.S. Appl. No. 13/449,539.

(56) References Cited

OTHER PUBLICATIONS

Applicant-Initiated Interview Summary Dated Nov. 14, 2018 From the US Patent and Trademark Office Re. U.S. Appl. No. 13/449,539. (3 pages).
Applicant-Initiated Interview Summary Dated Jan. 21, 2015 From the US Patent and Trademark Office Re. U.S. Appl. No. 13/449,539.
Applicant-Initiated Interview Summary Dated Feb. 22, 2016 From the US Patent and Trademark Office Re. U.S. Appl. No. 13/880,066.
Applicant-Initiated Interview Summary Dated Jan. 24, 2014 From the US Patent and Trademark Office Re. U.S. Appl. No. 13/449,539.
Applicant-Initiated Interview Summary Dated Apr. 25, 2018 From the US Patent and Trademark Office Re. U.S. Appl. No. 14/394,276. (3 pages).
Applicant-Initiated Interview Summary Dated Sep. 28, 2016 From the US Patent and Trademark Office Re. U.S. Appl. No. 13/905,224.
Communication Pursuant to Article 94(3) EPC Dated Dec. 2, 2020 From the European Patent Office Re. Application No. 15862313.2. (9 Pages).
Communication Pursuant to Article 94(3) EPC Dated Nov. 4, 2014 From the European Patent Office Re. Application No. 11833950.6.
Communication Pursuant to Article 94(3) EPC Dated Feb. 8, 2016 From the European Patent Office Re. Application No. 11833950.6.
Communication Pursuant to Article 94(3) EPC Dated Apr. 10, 2015 From the European Patent Office Re. Application No. 11782222.1.
Communication Pursuant to Article 94(3) EPC Dated Jun. 10, 2014 From the European Patent Office Re. Application No. 117822476.3.
Communication Pursuant to Article 94(3) EPC Dated Jun. 10, 2014 From the European Patent Office Re. Application No. 11784782.2.
Communication Pursuant to Article 94(3) EPC Dated Apr. 14, 2014 From the European Patent Office Re. Application No. 11782221.3.
Communication Pursuant to Article 94(3) EPC Dated Jul. 20, 2016 From the European Patent Office Re. Application No. 11782221.3.
Communication Pursuant to Article 94(3) EPC Dated Sep. 26, 2014 From the European Patent Office Re. Application No. 11782222.1.
Communication Pursuant to Article 94(3) EPC Dated Jul. 27, 2016 From the European Patent Office Re. Application No. 11782222.1.
Communication Pursuant to Article 94(3) EPC Dated Oct. 30, 2014 From the European Patent Office Re. Application No. 11782221.3.
Communication Pursuant to Rule 164(1) EPC: Supplementary Partial European Search Report and the European Provisional Opinion Dated May 18, 2018 From the European Patent Office Re. Application No. 15862313.2. (15 Pages).
Decision of Rejection Dated Sep. 2, 2022 From the China National Intellectual Property Administration Re. Application No. 20188003196.2 and its Summary in English. (4 Pages).
Decision of Rejection Dated Apr. 28, 2016 From the Japanese Patent Office Re. Application No. 2013-534435 and Its Machine Translation in English.
Final Official Action Dated Jun. 3, 2021 From the US Patent and Trademark Office Re. U.S. Appl. No. 13/905,224. (17 Pages).
Final Official Action Dated Jul. 12, 2022 from US Patent and Trademark Office Re. U.S. Appl. No. 16/494,322. (28 pages).
Final Official Action Dated Sep. 15, 2022 from US Patent and Trademark Office Re. U.S. Appl. No. 16/451,087. (13 pages).
International Preliminary Report on Patentability Dated May 2, 2013 From the International Bureau of WIPO Re. Application No. PCT/IB2011/054634.
International Preliminary Report on Patentability Dated May 2, 2013 From the International Bureau of WIPO Re. Application No. PCT/IB2011/054635.
International Preliminary Report on Patentability Dated May 2, 2013 From the International Bureau of WIPO Re. Application No. PCT/IB2011/054636.
International Preliminary Report on Patentability Dated May 2, 2013 From the International Bureau of WIPO Re. Application No. PCT/IB2011/054638.
International Preliminary Report on Patentability Dated May 2, 2013 From the International Bureau of WIPO Re. Application No. PCT/IB2011/054639.

International Preliminary Report on Patentability Dated May 2, 2013 From the International Bureau of WIPO Re. Application No. PCT/IB2011/054640.
International Preliminary Report on Patentability Dated May 2, 2013 From the International Bureau of WIPO Re. Application No. PCT/IB2011/054641.
International Preliminary Report on Patentability Dated Dec. 3, 2015 From the International Bureau of WIPO Re. Application No. PCT/IL2014/050457.
International Preliminary Report on Patentability Dated Oct. 3, 2019 From the International Bureau of WIPO Re. Application No. PCT/IL2018/050321. (11 Pages).
International Preliminary Report on Patentability Dated Oct. 3, 2019 From the International Bureau of WIPO Re. Application No. PCT/IL2018/050322. (16 Pages).
International Preliminary Report on Patentability Dated Aug. 7, 2014 From the International Bureau of WIPO Re. Application No. PCT/IL2013/050068.
International Preliminary Report on Patentability Dated Jun. 8, 2017 From the International Bureau of WIPO Re. Application No. PCT/IL2015/051145. (16 Pages).
International Preliminary Report on Patentability Dated Oct. 30, 2014 From the International Bureau of WIPO Re. Application No. PCT/IL2013/050339.
International Preliminary Report on Patentability Dated Oct. 30, 2014 From the International Bureau of WIPO Re. Application No. PCT/IL2013/050341.
International Search Report and the Written Opinion Dated May 2, 2016 From the International Searching Authority Re. Application No. PCT/IL2015/051145.
International Search Report and the Written Opinion Dated Feb. 7, 2012 From the International Searching Authority Re. Application No. PCT/IB2011/054641.
International Search Report and the Written Opinion Dated Oct. 11, 2013 From the International Searching Authority Re. Application No. PCT/IL2013/050341.
International Search Report and the Written Opinion Dated Sep. 19, 2013 From the International Searching Authority Re. Application No. PCT/IL2013/050068.
International Search Report and the Written Opinion Dated Nov. 20, 2014 From the International Searching Authority Re. Application No. PCT/IL2014/050457.
International Search Report and the Written Opinion Dated Jun. 22, 2012 From the International Searching Authority Re. Application No. PCT/IB2011/054640.
International Search Report and the Written Opinion Dated Jan. 23, 2012 From the International Searching Authority Re. Application No. PCT/IB2011/054635.
International Search Report and the Written Opinion Dated Jan. 25, 2012 From the International Searching Authority Re. Application No. PCT/IB2011/054636.
International Search Report and the Written Opinion Dated Jan. 27, 2012 From the International Searching Authority Re. Application No. PCT/IB2011/054634.
International Search Report and the Written Opinion Dated Jan. 27, 2012 From the International Searching Authority Re. Application No. PCT/IB2011/054638.
International Search Report and the Written Opinion Dated Aug. 28, 2018 From the International Searching Authority Re. Application No. PCT/IL2018/050322. (40 Pages).
International Search Report and the Written Opinion Dated Aug. 29, 2018 From the International Searching Authority Re. Application No. PCT/IL2018/050321. (16 Pages).
International Search Report and the Written Opinion Dated Jan. 31, 2012 From the International Searching Authority Re. Application No. PCT/IB2011/054639.
Invitation Pursuant to Rule 137(4) EPC Dated Apr. 4, 2014 From the European Patent Office Re. Application No. 11785792.0.
Invitation Pursuant to Rule 137(4) EPC Dated Apr. 8, 2014 From the European Patent Office Re. Application No. 11782222.1.
Invitation Pursuant to Rule 137(4) EPC Dated Apr. 10, 2014 From the European Patent Office Re. Application No. 11782476.3.

(56) References Cited

OTHER PUBLICATIONS

Invitation Pursuant to Rule 137(4) EPC Dated Mar. 21, 2016 From the European Patent Office Re. Application No. 11782222.1.
Invitation to Pay Additional Fees Dated Sep. 3, 2013 From the International Searching Authority Re. Application No. PCT/IL2013/050339.
Invitation To Pay Additional Fees Dated Mar. 4, 2016 From the International Searching Authority Re. Application No. PCT/IL2015/051145.
Invitation to Pay Additional Fees Dated Sep. 4, 2014 From the International Searching Authority Re. Application No. PCT/IL2014/050457.
Invitation to Pay Additional Fees Dated Aug. 5, 2013 From the International Searching Authority Re. Application No. PCT/IL2013/050341.
Invitation to Pay Additional Fees Dated Apr. 17, 2012 From the International Searching Authority Re. Application No. PCT/IB2011/054640.
Invitation to Pay Additional Fees Dated Jun. 21, 2018 From the International Searching Authority Re. Application No. PCT/IL2018/050322. (3 Pages).
Invitation to Pay Additional Fees Dated Jul. 24, 2013 From the International Searching Authority Re. Application No. PCT/IL2013/050068.
Invitation to Pay Additional Fees Dated Jun. 25, 2018 From the International Searching Authority Re. Application No. PCT/IL2018/050321. (2 Pages).
Notice of Allowance Dated Mar. 6, 2019 From the US Patent and Trademark Office Re. U.S. Appl. No. 14/394,276. (11 Pages).
Notice of Allowance Dated Oct. 6, 2014 From the US Patent and Trademark Office Re. U.S. Appl. No. 13/880,061.
Notice of Allowance Dated Nov. 7, 2013 From the US Patent and Trademark Office Re. U.S. Appl. No. 13/049,013.
Notice Of Allowance Dated Dec. 8, 2015 From the US Patent and Trademark Office Re. U.S. Appl. No. 14/049,238.
Notice of Allowance Dated Jan. 8, 2015 From the US Patent and Trademark Office Re. U.S. Appl. No. 13/880,061.
Notice of Allowance Dated Feb. 10, 2022 from US Patent and Trademark Office Re. U.S. Appl. No. 13/905,224. (8 pages).
Notice of Allowance Dated Aug. 11, 2020 from the US Patent and Trademark Office Re. U.S. Appl. No. 13/449,539. (11 pages).
Notice Of Allowance Dated Sep. 14, 2016 From the US Patent and Trademark Office Re. U.S. Appl. No. 13/879,400.
Notice Of Allowance Dated Jul. 18, 2016 From the US Patent and Trademark Office Re. U.S. Appl. No. 13/879,400.
Notice of Allowance Dated Jun. 21, 2013 From the US Patent and Trademark Office Re. U.S. Appl. No. 13/049,151.
Notice of Allowance Dated Sep. 23, 2020 from the US Patent and Trademark Office Re. U.S. Appl. No. 14/889,890. (8 pages).
Notice Of Allowance Dated Mar. 26, 2019 From the US Patent and Trademark Office Re. U.S. Appl. No. 14/190,113. (8 pages).
Notice of Allowance Dated Dec. 29, 2021 from US Patent and Trademark Office Re. U.S. Appl. No. 16/494,321. (51 pages).
Notice of Non-Compliant Amendment Dated Sep. 23, 2015 From the US Patent and Trademark Office Re. U.S. Appl. No. 13/880,124.
Notice of Reason for Rejection Dated Aug. 25, 2015 From the Japanese Patent Office Re. Application No. 2013-534435.
Notification of Office Action and Search Report Dated Apr. 1, 2021 From the State Intellectual Property Office of the People's Republic of China Re. Application No. 201880031396.2 and Its Translation of Office Action Into English. (9 Pages).
Notification of Office Action and Search Report Dated Dec. 1, 2014 From The State Intellectual Property Office of the People's Republic of China Re. Application No. 201180060862.8.
Notification of Office Action and Search Report Dated Mar. 14, 2022 From the State Intellectual Property Office of the People's Republic of China Re. Application No. 20188003196.2 and Its Translation of Office Action Into English. (15 Pages).

Office Action Dated Jul. 30, 2014 From The State Intellectual Property Office of the People's Republic of China Re. Application No. 201180060741.3 and Its Summary in English.
Official Action Dated Aug. 2, 2021 from the US Patent and Trademark Office Re. U.S. Appl. No. 16/494,321. (10 pages).
Official Action Dated Jul. 2, 2015 From the US Patent and Trademark Office Re. U.S. Appl. No. 13/879,400.
Official Action Dated Dec. 3, 2014 From the US Patent and Trademark Office Re. U.S. Appl. No. 13/462,956.
Official Action Dated Jun. 3, 2016 From the US Patent and Trademark Office Re. U.S. Appl. No. 13/880,066.
Official Action Dated Jun. 3, 2019 From the US Patent and Trademark Office Re. U.S. Appl. No. 13/449,539. (13 Pages).
Official Action Dated Nov. 3, 2017 From the US Patent and Trademark Office Re. U.S. Appl. No. 14/394,276. (11 pages).
Official Action Dated Nov. 4, 2014 From the US Patent and Trademark Office Re. U.S. Appl. No. 13/879,400.
Official Action Dated Aug. 5, 2015 From the US Patent and Trademark Office Re. U.S. Appl. No. 13/905,224.
Official Action Dated Jan. 5, 2016 From the US Patent and Trademark Office Re. U.S. Appl. No. 13/880,124.
Official Action Dated Jun. 5, 2015 From the US Patent and Trademark Office Re. U.S. Appl. No. 14/049,238.
Official Action Dated Nov. 5, 2014 From the US Patent and Trademark Office Re. U.S. Appl. No. 13/049,022.
Official Action Dated Feb. 6, 2015 From the US Patent and Trademark Office Re. U.S. Appl. No. 14/190,113.
Official Action Dated Jan. 6, 2017 From the US Patent and Trademark Office Re. U.S. Appl. No. 14/190,113. (11 pages).
Official Action Dated Oct. 7, 2014 From the US Patent and Trademark Office Re. U.S. Appl. No. 13/880,109.
Official Action Dated May 8, 2013 From the US Patent and Trademark Office Re. U.S. Appl. No. 13/462,956.
Official Action Dated Aug. 10, 2018 From the US Patent and Trademark Office Re. U.S. Appl. No. 14/190,113. (11 pages).
Official Action Dated Jun. 10, 2016 From the US Patent and Trademark Office Re. U.S. Appl. No. 14/190,113.
Official Action Dated Mar. 10, 2016 From the US Patent and Trademark Office Re. U.S. Appl. No. 13/449,539.
Official Action Dated Sep. 10, 2014 From the US Patent and Trademark Office Re. U.S. Appl. No. 14/049,238.
Official Action Dated Mar. 11, 2021 from the US Patent and Trademark Office Re. U.S. Appl. No. 16/494,321. (7 pages).
Official Action Dated Oct. 11, 2018 From the US Patent and Trademark Office Re. U.S. Appl. No. 14/394,276. (200 Pages).
Official Action Dated Sep. 11, 2015 From the US Patent and Trademark Office Re. U.S. Appl. No. 13/880,066.
Official Action Dated Apr. 13, 2020 from the US Patent and Trademark Office Re. U.S. Appl. No. 14/889,890. (23 pages).
Official Action Dated Aug. 13, 2020 from the US Patent and Trademark Office Re. U.S. Appl. No. 13/905,224. (24 pages).
Official Action Dated Apr. 14, 2014 From the US Patent and Trademark Office Re. U.S. Appl. No. 13/879,400.
Official Action Dated Aug. 14, 2015 From the US Patent and Trademark Office Re. U.S. Appl. No. 13/449,539.
Official Action Dated May 16, 2019 From the US Patent and Trademark Office Re. U.S. Appl. No. 15/529,137. (11 pages).
Official Action Dated Oct. 16, 2019 From the US Patent and Trademark Office Re. U.S. Appl. No. 13/449,539.(8 Pages).
Official Action Dated Jul. 17, 2013 From the US Patent and Trademark Office Re. U.S. Appl. No. 13/049,013.
Official Action Dated Nov. 17, 2017 From the US Patent and Trademark Office Re. U.S. Appl. No. 13/905,224. (19 pages).
Official Action Dated Dec. 19, 2013 From the US Patent and Trademark Office Re. U.S. Appl. No. 13/049,022.
Official Action Dated Mar. 20, 2014 From the US Patent and Trademark Office Re. U.S. Appl. No. 13/449,539.
Official Action Dated Oct. 20, 2017 From the US Patent and Trademark Office Re. U.S. Appl. No. 14/190,113. (7 pages).
Official Action Dated Apr. 21, 2017 From the US Patent and Trademark Office Re. U.S. Appl. No. 14/394,276. (13 pages).
Official Action Dated Feb. 21, 2019 From the US Patent and Trademark Office Re. U.S. Appl. No. 14/889,890. (19 pages).

(56)                    References Cited

OTHER PUBLICATIONS

Official Action Dated Jan. 21, 2022 From the US Patent and Trademark Office Re. U.S. Appl. No. 16/451,087. (150 Pages).
Official Action Dated Jun. 21, 2018 From the US Patent and Trademark Office Re. U.S. Appl. No. 13/449,539. (8 pages).
Official Action Dated Apr. 23, 2014 From the US Patent and Trademark Office Re. U.S. Appl. No. 13/880,061.
Official Action Dated Oct. 24, 2012 From the US Patent and Trademark Office Re. U.S. Appl. No. 13/049,013.
Official Action Dated Oct. 24, 2019 From the US Patent and Trademark Office Re. U.S. Appl. No. 14/889,890. (54 pages).
Official Action Dated Sep. 25, 2013 From the US Patent and Trademark Office Re. U.S. Appl. No. 13/462,956.
Official Action Dated Sep. 25, 2015 From the US Patent and Trademark Office Re. U.S. Appl. No. 14/190,113.
Official Action Dated Jul. 26, 2016 From the US Patent and Trademark Office Re. U.S. Appl. No. 13/880,124.
Official Action Dated Dec. 27, 2016 From the US Patent and Trademark Office Re. U.S. Appl. No. 13/449,539. (13 pages).
Official Action Dated Apr. 29, 2016 From the US Patent and Trademark Office Re. U.S. Appl. No. 13/905,224.
Official Action Dated Aug. 29, 2013 From the US Patent and Trademark Office Re. U.S. Appl. No. 13/449,539.
Official Action Dated Jan. 29, 2013 From the US Patent and Trademark Office Re. U.S. Appl. No. 13/049,151.
Official Action Dated Aug. 31, 2021 from the US Patent and Trademark Office Re. U.S. Appl. No. 16/494,322. (27 pages).
Official Action Dated Oct. 31, 2018 From the US Patent and Trademark Office Re. U.S. Appl. No. 13/905,224. (23 pages).
Restriction Official Action Dated Jan. 4, 2019 From the US Patent and Trademark Office Re. U.S. Appl. No. 15/529,137. (8 pages).
Restriction Official Action Dated Oct. 5, 2012 From the US Patent and Trademark Office Re. U.S. Appl. No. 13/049,151.
Restriction Official Action Dated Jul. 7, 2014 From the US Patent and Trademark Office Re. U.S. Appl. No. 14/049,238.
Restriction Official Action Dated Apr. 14, 2015 From the US Patent and Trademark Office Re. U.S. Appl. No. 13/880,124.
Restriction Official Action Dated Nov. 17, 2014 From the US Patent and Trademark Office Re. U.S. Appl. No. 13/880,066.
Restriction Official Action Dated May 24, 2018 From the US Patent and Trademark Office Re. U.S. Appl. No. 14/889,890. (8 pages).
Restriction Official Action Dated Feb. 27, 2015 From the US Patent and Trademark Office Re. U.S. Appl. No. 13/905,224.
Restriction Official Action Dated Mar. 27, 2015 From the US Patent and Trademark Office Re. U.S. Appl. No. 13/880,095.
Restriction Official Action Dated Oct. 27, 2016 From the US Patent and Trademark Office Re. U.S. Appl. No. 14/394,276.
Restriction Official Action Dated Jun. 28, 2013 From the US Patent and Trademark Office Re. U.S. Appl. No. 13/449,539.
Restriction Official Action Dated Aug. 30, 2012 From the US Patent and Trademark Office Re. U.S. Appl. No. 13/049,013.
Restriction Official Action Dated Oct. 30, 2014 From the US Patent and Trademark Office Re. U.S. Appl. No. 13/880,083.
Search Report Dated Jul. 17, 2014 From The State Intellectual Property Office of the People's Republic of China Re. Application No. 201180060741.3 and Its Machine Translation in English.
Summons to Attend Oral Proceedings Pursuant to Rule 115(1) EPC Dated Mar. 11, 2022 From the European Patent Office Re. Application No. 15862313.2. (12 Pages).
Supplemental Notice of Allowance Dated Mar. 31, 2022 from US Patent and Trademark Office Re. U.S. Appl. No. 16/494,321. (4 pages).
Supplementary European Search Report and the European Search Opinion Dated Dec. 4, 2020 From the European Patent Office Re. Application No. 18771348.2. (9 Pages).
Supplementary European Search Report and the European Search Opinion Dated Sep. 5, 2018 From the European Patent Office Re. Application No. 15862313.2. (13 Pages).

Supplementary European Search Report and the European Search Opinion Dated Dec. 22, 2016 From the European Patent Office Re. Application No. 14801877.3. (9 Pages).
Supplementary European Search Report Dated Mar. 12, 2014 From the European Patent Office Re. Application No. 11833950.6.
Translation Dated Mar. 12, 2015 of Notification of Office Action and Search Report Dated Dec. 1, 2014 From The State Intellectual Property Office of the People's Republic of China Re. Application No. 201180060862.8.
Translation Dated Nov. 18, 2015 of Notice of Reason for Rejection Dated Aug. 25, 2015 From the Japanese Patent Office Re. Application No. 2013-534435.
Ahmed et al. "Renal Sympathetic Denervation Using An Irrigated Radiofrequency Ablation Catheter for the Management of Drug-Resistant Hypertension", Journal of the American College of Cardiology: Cardiovascular Interventions, JACC, 5(7): 758-765, 2012.
Ali et al. "Signal Processing Overview of Ultrasound Systems for Medical Imaging", Texas Instruments White Paper, SPRAB12: 1-27, Nov. 2008.
Anonymus "Indication for and Results of Sympathectomy in Patients With Peripheral Vascular Disease", Lumbar Sympathectomy, Poster, 34 P., 2009.
Aoyama et al. "Comparison of Cryothermia and Radiofrequency Current in Safety and Efficacy of Catheter Ablation Within the Canine Coronary Sinus Close to the Left Circumflex Coronary Artery", Journal of Cardiovascular Electrophysiology, 16: 1218-1226, Nov. 2005.
Atherton et al. "Micro-Anatomy of the Renal Sympathetic Nervous System: A Human Postmortem Histologic Study", Clinical Anatomy, p. 1-6, Oct. 4, 2011.
Bailey et al. "Cavitation Detection During Shock-Wave Lithotripsy", Ultrasound in Medicine and Biology, XP027605630, 31(9): 1245-1256, Sep. 1, 2005. Abstract, Fig.1, p. 1246, p. 1247, r-h col. p. 1249, r-h col.
Baker et al. "Operative Lumbar Sympathectomy for Severe Lower Limb Ischaemia: Still A Valuable Treatment Option", Annals of the Royal College of Surgeons of England, 76(1): 50-53, Jan. 1994.
Bambi et al. "Real-Time Digital Processing of Doppler Ultrasound Signals", IEEE International Conference on Acoustics, Speech, and Signal Processing, Proceedings, (ICASSP '05), (5): v/977-v/980, Mar. 23-23, 2005.
Bandyopadhyay et al. "Outcomes of Beta-Blocker Use in Pulmonary Arterial Hypertension: A Propensity-Matched Analysis", European Respiratory Journal, 46(3): 750-760, Published Online May 28, 2015.
Bharat et al. "Monitoring Stiffness Changes in Lesions After Radiofrequency Ablation at Different Temperatures and Durations of Ablation", Ultrasound in Medicine & Biology, 31(3): 415-422, 2005.
Bhatt et al. "A Controlled Trial of Renal Denervation for Resistant Hypertension", The New England Journal of Medicine, 270(15): 1393-1401, Published Online Mar. 29, 2014.
Blankestijn et al. "Renal Denervation: Potential Impact on Hypertension in Kidney Disease?", Nephrology, Dialysis, Transplantation, 26(9): 2732-2734, Apr. 19, 2011.
Brandt et al. "Effects of Renal Sympathetic Denervation on Arterial Stiffness and Central Hemodynamics in Patients With Resistant Hypertension", Journal of the American College of Cardiology, 60(19): 1956-1965, 2012.
Brandt et al. "Renal Sympathetic Denervation Reduces Left Ventricular Hypertrophy and Improves Cardiac Function in Patients With Resistant Hypertension", Journal of the American College of Cardiology, 59(10): 901-909, 2012.
Brasselet et al. "Effect of Local Heating on Restenosis and In-Stent Neointimal Hyperplasia in the Atherosclerotic Rabbit Model: A Dose-Ranging Study", European Heart Journal, 29: 402-412, 2008.
Brinton et al. "Externally Focused Ultrasound for Sympathetic Renal Denervation", Wave I First-In-Man Study, Kona Medical Inc., PowerPont Presentation, TCT 2012, 15 P., 2012.
Campese et al. "Renal Afferent Denervation Prevents the Progression of Renal Disease in the Renal Ablation Model of Chronic Renal Failure in the Rat", American Journal of Kidney Diseases, 26(5): 861-865, Nov. 1995. Abstract.

(56) References Cited

OTHER PUBLICATIONS

Campese et al. "Sympathetic Renal Innervation and Resistant Hypertension", International Journal of Hypertension, 2011(Art.ID 814354): 1-6, 2011.

Cardiosonic "Cardiosonic New Applications", Cardiosonic, p. 1-20, Mar. 2014.

Cardiosonic "Histological Map of Swine Pulmonary Arteries", Cardiosonic, Animal #223, Mar. 26, 2014.

Cardiosonic "Histological Map of Swine Pulmonary Arteries", Cardiosonic, Animal #234, Mar. 18, 2014.

Cardiosonic "Histological Map of Swine Pulmonary Arteries", Cardiosonic, Animal #234, Mar. 26, 2014.

Cardiosonic "Histopathology Report", Cardiosonic, 2 P., Dec. 26, 2013.

Cardiosonic "PA/Trachea—Feedback Provisional", Cardiosonic, 5 P, Jun. 9, 2014.

Cardiosonic "PAH Preliminary Development Meeting Minutes", Cardiosonic, 2 P., Mar. 23, 2014.

Chen et al. "Artery Denervation to Treat Pulmonary Arterial Hypertension. The Single-Center, Prospective, First-in-Man PADN-1 Study (First-in-Man Pulmonary Artery Denervation for Treatment of Pulmonary Artery Hypertension)", Journal of the American College of Cardiology, JACC, 62(12): 1092-1100, Sep. 17, 2013.

Chen et al. "Hemodynamic, Functional, and Clinical Responses to Pulmonary Artery Denervation in Patients With Pulmonary Arterial Hypertension of Different Causes: Phase II Results From the Pulmonary Artery Denervation-1 Study", Circulation: Cardiovascular Interventions, 8(11): e002837-1-e002837-10, Nov. 9, 2015.

Chen et al. "Percutaneous Pulmonary Artery Denervation Completely Abolishes Experimental Pulmonary Arterial Hypertension In Vivo", EuroIntervention, 9(2): 269-276, Jun. 22, 2013.

Ciarka et al. "Prognostic Significance of Sympathetic Nervous System Activation in Pulmonary Arterial Hypertension", American Journal of Respiratory and Critical Care Medicine, 181(11): 1269-1275, Published Online Mar. 1, 2010.

CIBIS-II Investigators and Committees "The Cardiac Insufficiency Bisoprolol Study II (CIBIS-II): A Randomised Trial", The Lancet, 353(9146): 9-13, Jan. 2, 1999.

Cohn et al. "A Comparison of Enalapril With Hydralazine-Isosorbide Dinitrate in the Treatment of Chronic Congestive Heart Failure", The New England Journal of Medicine, 325(5): 303-310, Aug. 1, 1991.

CONSENSUS Trial Study Group "Effects of Enalapril on Mortality in severe Congestive Heart Failure. Results of the Cooperative North Scandinavian Enalapril Survival Study (CONSENSUS)", The New England Journal of Medicine, 316(23): 1429-1435, Jun. 4, 1987.

Copty et al. "Localized Heating of Biological Media Using A 1-W Microwave Near-Field Probe", IEEE Transactions on Microwave Theory and Techniques, 52(8): 1957-1963, Aug. 2004.

Copty et al. "Low-Power Near-Field Microwave Applicator for Localized Heating of Soft Matter", Applied Physics Letters, 84(25): 5109-5111, Jun. 21, 2004.

Damianou et al. "Dependence of Ultrasonic Attenuation and Absorption in Dog Soft Tissues on Temperature and Thermal Dose", Journal of the Acoustical Society of America, 102(1): 628-634, Jul. 1997.

Davies et al. "First-in-Man Safety Evaluation of Renal Denervation for Chronic Systolic Heart Failure: Primary Outcome From REACH-Pilot Study", International Journal of Cardiology, 162: 189-192, 2013.

De Man et al. "Bisoprolol Delays Progression Towards Right Heart Failure in Experimental Pulmonary Hypertension", Circulation Heart Failure, 5(1): 97-105, Published Online Dec. 9, 2011.

De Man et al. "Neurohormonal Axis in Patients With Pulmonary Arterial Hypertension. Friend or Foe?", American Journal of Respiratory and Critical Care Medicine, 187(1): 14-19, Published Online Nov. 9, 2012.

Deneke et al. "Histopathology of Intraoperatively Induced Linear Radiofrequency Ablation Lesions in Patients With Chronic Atrial Fibrillation", European Heart Journal, 26: 1797-1803, 2005.

Dewhirst et al. "Basic Principles of Thermal Dosimetry and Thermal Thresholds for Tissue Damage From Hyperthermia", International Journal of Hyperthermia, 19(3): 267-294, May-Jun. 2003.

DiBona "Neural Control of Renal Function: Cardiovascular Implications", Hypertension, 13: 539-548, 1989.

DiBona "Neural Control of the Kidney: Past, Present, and Future", Hypertension, 41: 621-624, Dec. 16, 2002.

DiBona "Physiology in Perspective: The Wisdom of the Body. Neural Control of the Kidney", American Journal of Physiology, Regulatory, Integrative and Comparative Physiology, 289(3): R633-R641, Sep. 2005.

DiBona et al. "Differentiated Sympathetic Neural Control of the Kidney", American Journal of Physiology, 271: R84-R90, 1996.

DiBona et al. "Translational Medicine: The Antihypertensive Effect of Renal Denervation", American Journal of Physiology, Regulatory, Integrative and Comparative Physiology, 298(2): R245-R253, Feb. 2010.

Diederich et al. "Catheter-Based Ultrasound Applicators for Selective Thermal Ablation: Progress Towards MRI-Guided Applications in Prostate", International Journal of Hyperthermia, 20(7): 739-756, Nov. 2004.

Diederich et al. "Catheter-Based Ultrasound Devices and MR Thermal Monitoring for Conformal Prostate Thermal Therapy", 30th Annual International IEEE EMBS Conference, Vancouver, British Columbia, Canada, Aug. 20-24, 2008, p. 3664-3668, 2008.

Diederich et al. "Induction of Hyperthermia Using An Intracavitary Multielement Ultrasonic Applicator", IEEE Transactions on Biomedical Engineering, 36(4): 432-438, Apr. 1989.

Diederich et al. "Ultrasound Technology for Hyperthermia", Ultrasound in Medicine & Biology, 25(6): 871-887, 1999.

Donoho et al. "Stable Recovery of Sparse Overcomplete Representations in the Presence of Noise", IEEE Transactions on Information Theory, 52(1): 1-42, Jan. 2006.

Drake et al. "Problematic Anatomical Sites Around the Pulmonary Artery", Gray's Anatomy for Students, 9 P., 2004.

Esler "The 2009 Carl Ludwig Lecture: Pathophysiology of the Human Sympathetic Nervous System in Cardiovascular Diseases: The Transition From Mechanisms to Medical Management", Journal of Applied Physiology, 108: 227-237, 2010.

Esler et al. "Measurement of Total and Organ-Specific Norepinephrine Kinetics in Humans", American Journal of Physiology-Endocrinology Metabolism 10, 247(1/Pt.1): E21-E28, Jul. 1984.

Esler et al. "Renal Sympathetic Denervation for Treatment of Drug-Resistant Hypertension: One-Year Results From the Symplicity HTN-2 Randomized, Controlled Trial", Circulation, 126: 2976-2982, 2012.

Failla et al. "Sympathetic Tone Restrains Arterial Distensibility of Healthy and Atherosclerotic Subjects", Journal of Hypertension, 17: 1117-1123, 1999.

Fischell PeriVascular Renal Denervation (PVRD#), Ablative Solutions Inc., TransCatheter Therapeutics Meeting, Miami, FL, USA, Oct. 24, 2012, PowerPoint Presentation, 14 P., Oct. 2012.

Fort Wayne Metals "HHS Tube", Fort Wayne Metals Research Products Corporation, 2 P., 2009.

Fujikura et al. "Effects of Ultrasonic Exposure Parameters on Myocardial Lesions Induced by High-Intensity Focused Ultrasound", Journal of Ultrasound Medicine, 25: 1375-1386, 2006.

Galie et al. "2015 ESC/ERS Guidelines for the Diagnosis and Treatment of Pulonary Hypertension. The Joint Task Force for the Diagnosis and Treatment of Pulmonary Hypertension of the European Society of Cardiology (ESC) and the European Respiratory Society (ERS). Endorsed by: Association for European Paediatric and Congenital Cardiology (AEPC), International Society for Heart and Lung Transplantation (ISHLT)", European Heart Journal, 37(1): 67-119, Published Online Aug. 29, 2015.

Galie et al. "New Treatment Stategies for Pulmonary Arterial Hypertension. Hopes or Hypes?", Journal of the American College of Cardiology, 62(12): 1101-1102, Sep. 17, 2013.

(56) References Cited

OTHER PUBLICATIONS

Galie et al. "Updated Treatment Algorithm of Pulmonary Arterial Hypertension", Journal of the American College of Cardiology, 62(25/Suppl.D): D60-D72, 2013.

Gander et al. "Least-Squares Fitting of Circles and Ellipses", BIT Numerical Mathematics, 34(4): 558-578, Dec. 1994.

Giering et al. "Determination of the Specific Heat Capacity of Healthy and Tumorous Human Tissue", Thermochimica Acta, 251: 199-205, Mar. 1995.

Glazier et al. "Laser Balloon Angioplasty Combined With Local Intrcoronary Heparin Therapy: Immediate and Short-Term Follow-Up Results", American Heart Journal, 134: 266-273, 1997.

Goswami "Renal Denervation: A Percutaneous Therapy for HTN", Prairie Heart Institute, Synvacor, The VEINS: Venous Endovascular Interventions Strategies, Chicago, USA, 42 P., 2012.

Granada et al. "A Translational Overview for the Evaluation of Peri-Renal Denervation Technologies", Cardiovascular Research Foundation, Columbai University Medical Center, New York, USA, Alizee Pathology, 25 P., 2011.

Grassi et al. "Sympathetic Mechanisms, Organ Damage, and Anti-hypertensive Treatment", Current Hypertension Report, 13: 303-308, 2011.

Griffiths et al. "Thoraco-Lumbar Splanchnicectomy and Sympathectomy. Anaesthetic Procedure", Anaesthesia, 3(4): 134-146, Oct. 1948.

Grimson et al. "Total Thoracic and Partial to Total Lumbar Sympathectomy, Splanchnicectomy and Celiac Ganglionectomy for Hypertension", Annals of Surgery, 138(4): 532-547, Oct. 1953.

Heath et al. "The Structure of the Pulmonary Trunk at Different Ages and in Cases of Pulmonary Hypertension and Pulmonary Stenosis", The Journal of Pathology and Bacteriology, 77(2): 443-456, Apr. 1959.

Hering et al. "Renal Denervation in Moderate to Severe CKD", Journal of the American Society of Nephrology, 23: 1250-1257, 2012.

Hering et al. "Substantial Reduction in Single Sympathetic Nerve Firing After Renal Denervation in Patients With rRsistant Hypertension", Hypertension, 61: 1-14, Nov. 19, 2012.

Holdaas et al. "Modulation of Reflex Renal Vasoconstriction by Increased Endogenous Renal Prostaglandin Synthesis", The Journal of Pharmacology and Experimental Therapeutics, 232(3): 725-731, 1985.

Humbert et al. "Advances in Therapeutic Interventions for Patients With Pulmonary Arterial Hypertension", Circulation, XP055531396, 130(24): 2189-2208, Published Online Dec. 9, 2014.

Janssen et al. "Role of Afferent Renal Nerves in Spontaneous Hypertension in Rats", Hypertension, 13: 327-333, 1989.

Joner "Histopathological Characterization of Renal Arteries After Radiofrequency Catheter Based Sympathetic Denervation in A Healthy Porcine Model", Deutsches Herzzentrum M?nchen, Technische Universit?t M?nchen, PowerPoint Presentation, TCT 2012, 15 P., 2012.

Katholi "Renal Nerves in the Pathogenesis of Hypertension in Experimental Animals and Humans", American Journal of Physiology, 245: F1-F14, 1983.

Katholi et al. "Intrarenal Adenosine Produces Hypertension by Activating the Sympathetic Nervous System Via the Renal Nerves in the Dog", Journal of Hypertension, 2: 349-359, 1984.

Katholi et al. "Renal Nerves in the Maintenance of Hypertension: A Potential Therapeutic Target", Current Hypertension Reports, 12(3): 196-204, Jun. 2010.

Kleinlogel et al. "A Gene-Fusion Strategy for Stoichiometric and Co-Localized Expression of Light-Gated Membrane Proteins", Nature Methods, 8(12): 1083-1091, Dec. 2011.

Kline et al. "Functional Reinnervation and Development of Super-sensitivity to NE After Renal Denervation in Rats", American Journal of Physiology, 238: R353-R358, 1980.

Kolh "Carotid Denervation by Adventitial Stripping: A Promising Treatment of Carotid Sinus Syndrome?", European Journal of Vascular and Endovascular Surgery, 39(2): 153-154, Feb. 2010.

Krum et al. "Catheter-Based Renal Sympathetic Denervation for Resistant Hypertension: A Multicentre Safety and Proof-of-Principle Cohort Study", The Lancet, 373: 1275-1281, Apr. 11, 2009.

Krum et al. "Catheter-Based Renal Sympathetic Denervation for Resistant Hypertension: A Multicentre Safety and Proof-of-Principle Cohort Study", The Lancet, 373: 1275-1281, Mar. 30, 2009.

Kummer "Pulmonary Vascular Innervation and Its Role in Responses to Hypoxia: Size Matters!", Proceedings of the American Thoracic Society, 8(6): 471-476, Nov. 1, 2011.

Lafon "Miniature Devices for Minimally Invasive Thermal Ablation by High Intensity Ultrasound", Cargese Workshop 2009, University of Lyon, France, INSERM U556, Presentation, 39 P., 2009.

Lambert et al. "Redo of Percutaneous Renal Denervation in A Patient With Recurrent Resistant Hypertension After Primary Treatment Success", Catheterization and Cardiovascular Interventions, p. 1-11, 2012.

Lele "Effects of Focused Ultrasonic Radiation on Peripheral Nerve, With Observations on Local Heating", Experimental Neurology, 8: 47-83, 1963.

Lemoine et al. "Amputations and Sympathectomy in Peripheral Vascular Disease of the Lower Extremity. Experience With 180 Patients", Journal of the National Medical Association, 61(3): 219-221, May 1969.

Li et al. "Acoustic Proximity Ranging in the Presence of Secondary Echoes", IEEE Transactions on Instrumentation and Measurement, XP011102759, 52(5): 1593-1605, Oct. 1, 2003. p. 1593.

Lin et al. "Utility of the PlasmaKinetic™M Bipolar Forceps® for Control of the Renal Artery in A Porcine Model", JTUA, 14(3): 118-121, Sep. 2003.

Liu et al. "A Helical Microwave Antenna for Welding Plaque During Balloon Angioplasty", IEEE Transactions on Microwave Theory and Techniques, 44(10): 1819-1831, Oct. 1996.

Liu et al. "Pulmonary Artery Denervation Improves Pulmonary Arterial Hypertension Induced Right Ventricular Dysfunction by Modulating the Local Renin-Angiotensin-Aldosterone System", BMC Cardiovascular Disorders, 16(1): 192-1-192-10, Oct. 10, 2016.

Lopez et al. "Effects of Sympathetic Nerves on Collateral Vessels in the Limb of Atherosclerosis Primates", Atherosclerosis, 90: 183-188, 1991.

Mabin et al. "First Experience With Endovascular Ultrasound Renal Denervation for the Treatment of Resistant Hypertension", EuroIntervention, 8: 57-61, 2012.

Mahfoud et al. "Effect of Renal Sympathetic Denervation on Glucose Metabolism in Patients With Resistant Hypertension: A Pilot Study", Circulation, 123: 1940-1946, 2011.

Mahfoud et al. "Is There A Role for Renal Sympathetic Denervation in the Future Treatment of Resistant Hypertension?", Future Cardiology, 7(5): 591-594, 2011.

Mahfoud et al. "Renal Hemodynamics and Renal Function After Catheter-Based Renal Sympathetic Denervation in Patients With Resistant Hypertension", Hypertension, 60: 419-424, 2012.

Makris et al. "Resistant Hypertension Workup and Approach to Treatment", International Journal of Hypertension, 2011(Art. ID598694): 1-10, 2011.

Manasse et al. "Clinical Histopathology and Ultrstructural Analysis of Myocardium Following Microwave Energy Ablation", European Journal of Cardio-Thoracic Surgery, 23: 573-577, 2003.

Mangoni et al. "Effect of Sympathectomy on Mechanical Properties of Common Carotid and Femoral Arteries", Hypertension, 30: 1085-1088, 1997.

Martin et al. "Premise, Promise, and Potential Limitations of Invasive Devices to Treat Hypertension", Current Cardiology Reports, 13(1): 86-92, Feb. 2011.

Mazor "Efficacy of Renal Denervation Is Positively Impacted by Longitudinal Treatments", Vessix Vascular Inc., PowerPoint Presentation, TCT 2012, 20 P., 2012.

MERIT-HF Study Group "Effect of Metaprolol CR/XL in Chronic Heart Failure: Metoprolol CR/XL Randomised Intervention Trial in Congestive Heart Failure (MERIT-HF)", The Lancet, 353(9169): 2001-2007, Jun. 12, 1999.

(56) References Cited

OTHER PUBLICATIONS

Mogil et al. "Renal Innervation and Renin Activity in Salt Metabolism and Hypertension", American Journal of Physiology, 216(4): 693-697, Apr. 1969.

Moretti et al. "Beta Blocker for Patients With Pulmonary Arterial Hypertension: A Single Center Experience", International Journal of Cardiology, 184(1): 528-532, Available Online Feb. 24, 2015.

Mortensen et al. "Catheter-Based Renal Sympathetic Denervation Improves Central Hemodynamics and Arterial Stiffness: A Pilot Study", The Journal of Clinical Hypertension, 14(12): 861-870, Dec. 2012.

Nootens et al. "Neurohormonal Activation in Patients With Right Ventricular Failure From Pulmonary Hypertension: Relation to Hemodynamic Variables and Endothelin Levels", Journal of the American College of Cardiology, JACC, 26(7): 1581-1585, Dec. 1995.

Ohkubo et al. "Histological Findings After Angioplasty Using Conventional Balloon, Radiofrequency Thermal Balloon, and Stent for Experimental Aortic Coarctation", Pediatrics International, 46: 39-47, 2004.

Olafsson et al. "Ultrasound Current Source Density Imaging", IEEE Transactions on Biomedical Engineering, 55(7): 1840-1848, Jul. 2008.

Ong et al. "Successful Treatment of Resistant Hypertension With Percutaneous Renal Denervation Therapy", Heart, 98(23): 1754-1755, Dec. 2012.

Ormiston "OneShot (Covidien)", Maya Medical, Auckland, New Zealand, PowerPoint Presentation.

Ormiston et al. "First-in-Human Use of the OneShot™ M Renal Denervation System From Covidien", EuroIntervention, 8: 1090-1094, 2013.

Packer et al. "Effect of Carvedilol on Survival in Severe Chronic Heart Failure", The New England Journal of Medicine, 344(22): 1651-1658, May 31, 2001.

Page et al. "The Effect of Renal Denervation on Patients Suffering From Nephritis", The Journal of Clinical Investigation, 14(4): 443-458, Jul. 1935.

Papademetriou et al. "Renal Sympathetic Denervation for the Treatment of Difficult-to-Control or Resistant Hypertension", International Journal of Hypertension, 2011(Art.ID196518): Jan. 1-8, 2011.

Para Tech Coating "Parylene Properties", Para Tech Coating Inc., 1 P., 2010.

Perros et al. "Nebivolol for Improving Endothelial Dysfunction, Pulmonary Vascular Remodeling, and Right Heart Function in Pulmonary Hypertension", Journal of the American College of Cardiology, JACC, 65(7): 668-680, Feb. 24, 2015.

Pokushalov et al. "A Randomized Comparison of Pulmonary Vein Isolation With Versus Without Concomitant Renal Artery Denervation in Patients With Refractory Symptomatic Atrial Fibrillation and Resistant Hypertension", Journal of the American College of Cardiology, 60(13): 1163-1170, 2012.

Prapa et al. "Histopathology of the Great Vessels in Patients With Pulmonary Arterial Hypertension in Association With Congenital Heart Disease: Large Pulmonary Arteries Matter Too", international Journal of Cardiology, 168: 2248-2254, Available Online Feb. 28, 2013.

Prochnau et al. "Catheter-Based Renal Denervation for Drug-Resistant Hypertension by Using A Standard Electrophysiology Catheter", EuroIntervention, 7: 1077-1080, 2012.

Prochnau et al. "Efficacy of Renal Denervation With A Standard EP Catheter in the 24-h Ambulatory Blood Pressure Monitoring—Long-Term Follow-Up", International Journal of Cardiology, 157(3): 447-448, Jun. 14, 2012.

Qin "Physician's Prescription Manual", Wen-han, Qin: 590, People's Military Medical Press, Feb. 1998 with Machine Translation.

Quinn "Pre-Eclampsia and Partial Uterine Denervation", Medical Hypotheses, 64(3): 449-454, 2005. Abstract.

Rappaport "Treating Cardiac Disease With Catheter-Based Tissue Heating", IEEE Microwave Magazine, p. 57-64, Mar. 2002.

Reddy "Sound Intervention", Mount Sinai School of Medicine, MSSM, Presentation, 19 P., 2012.

Roehl et al. "Comparison of 3 Methods to Induce Acute Pulmonary Hypertension in Pigs", Comparative Medicine, 59(3): 280-286, Jun. 2009.

Rosanio et al. "Pulmonary Arterial Hypertension in Adults: Novel Drugs and Catheter Ablation Techniques Show Promise? Systematic Review on Pharmacotherapy and Interventional Strategies", BioMed Research International, XP055754039, 2014(IArt.743868): 1-17, Jun. 12, 2014.

Rothman "FIM Evaluation of A New, Multi-Electrode RF System for Renal Denervation (Medtronic)", Medtronic Inc., PowerPoint Presentation, 8 P., 2012.

Rothman et al. "Pulmonary Artery Denervation Reduces Pulmonary Artery Pressure and Induces Histological Changes in An Acute Porcine Model of Pulmonary Hypertension", Circulation: Cardiovascular Interventions, 8(11): e002569-1-e002569-7, Published Online Nov. 17, 2015.

Rousselle "Experimental Pathways for the Evaluation of Extrinsic Renal Nerve Distribution, Density, and Quantification (Swine Model)", Alizee Pathology in Collaboration With Jack Skirkball Center for Cardiovascular Research, TCT, 20 P., Nov. 8, 2011.

Rousselle "Renal Artery Dervation: Experimental Pathways for the Evaluation of Extrinsic Renal Nerve Distribution, Density, and Quantification (Swine Model)", Alizee Pathology, Cardiovascular Research Foundation, Nov. 8, 2011.

Sakakura et al. "Methodological Standardization for the Pre-Clinical Evaluation of Renal Sympathetic Denervation", JACC: Cardiovascular Interventions. 7(10): 1184-1193, Published Online Sep. 14, 2014.

Sangiorgi et al. "Histo-Morphometric Evaluation of 2D Characteristics and 3D Sympatetic Renal Nerve Distribution in Hypertensive Vs. Normotensive Patients", Department of Pathology, Department of Cardiology, University of Rome Tor Vergata, Department of Cardiology University of Modena and Reggio Emilia, Medtronic Cardiovascular, PowerPoint Presentation, TCT 2012, 22 P., 2012.

Sanni et al. "Is Sympathectomy of Benefit in Critical Leg Ischaemia Not Amenable to Revascularisation?", Interactive Cardio Vascular and Thoracic Surgery, 4: 478-483, 2005.

Scheinert "Cardiosonic TIVUS™ Technology: An Intra-Vascular Ultrasonic Catheter for Targeted Renal Denervation", Center for Vascular Medicine, Park Hospital Leipzig, Germany, PowerPoint Presentation, TCT 2012, 16 P., 2012.

Schelegle et al. "Vagal Afferents Contribute to Exacerbates Airway Responses Following Ozone and Allergen Challenge", Respiratory Physiology & Neurobiology, 181(3): 277-285, May 31, 2012.

Schlaich "Long-Term Follow Up of Catheter-Based Renal Denervation for Resistant Hypertension Confirms Durable Blood Pressure Reduction", Hypertension & Kidney Disease Laboratory, Baker IDI Heart & Diabetes Institute, Melbourne VIC, Australia, PowerPoint Presentation, TCT 2012, 22 P., 2012.

Schlaich et al. "Renal Sympathetic-Nerve Ablation for Uncontrolled Hypertension", New England Journal of Medicine, 361(9): 932-934, Aug. 27, 2009.

Schnyder et al. "Common Femoral Artery Anatomy Is Influenced by Demographics and Comorbidity: Implications for Cardiac and Peripherial Invasive Studies", Catheterization and Cardiovascular Interventions, 53(3): 289-295, Jul. 2001.

Schwartz "Strategies to Model Efficacy of Hypertension Devices", EuroPCR 2013, The Leading Cardiovascular Course, 24 P., 2013.

Shelton Jr. et al. "A Nondestructive Technique to Measure Pulmonary Artery Diameter and Its Pulsatile Variations", Journal of Applied Physiology, 33(4): 542-544, Oct. 1972.

Shung "Doppler Flow Measurements", Diagnostic Ultrasound-Imaging and Blood Flow Measurements, Chap.5:103-104, 2006.

Sievert et al. "Catheter-Based Technology Alternatives for Renal Denervation", Cardio Vascular Center Frankfurt, Germany, TCT 2012, Miami, FL, USA, Oct. 22-26, 2012, PowerPoint Presentation, 35 P., Oct. 2012.

Simonneau et al. "Updated Clinical Classification of Pulmonary Hypertension", Journal of the American College of Cardiology, 54(1/Suppl.S): S43-S54, Jun. 30, 2009.

(56) References Cited

OTHER PUBLICATIONS

Sitbon et al. "Beyond A Single Pathway: Combination Therapy in Pulmonary Arterial Hypertension", European Respiratory Review, 25(142): 408-417, Dec. 2016.

SOLVD Investigators "Effect of Enalapril on Survival in Patients With Reduced Left Ventricular Ejection Fractions and Congestive Heart Failure", The New England Journal of Medicine, 325(5): 293-302, Aug. 1, 1991.

Souchon et al. "Monitoring the Formation of Thermal Lesions With Heat-Induced Echo-Strain Imaging: A Feasibility Study", Ultrasound in Medicine & Biology, 31(2): 251-259, 2005.

Stefanadis "Vincristine Local Delivery for Renal Artery Denervation", Athens, Greece, PowerPoint Presentation, TCT 2012, 21 P., 2012.

Steigerwald et al. "Morphological Assessment of Renal Arteries After Radiofrequency Catheter-Based Sympathetic Denervation in A Porcine Model", Journal of Hypertension, 30(11): 2230-2239, Nov. 2012.

Swierblewska et al. "An Independent Relationship Between Muscle Sympathetic Nerve Activity and Pulse Wave Velocity in Normal Humans", Journal of Hypertension, 28: 979-984, 2010.

Symplicity HTN-1 Investigators "Catheter-Based Renal Sympathetic Denervation for Resistant Hypertension: Durability of Blood Pressure Reduction Out to 24 Months", Hypertension, 57: 911-917, Mar. 14, 2011.

Symplicity HTN-2 Investigators "Renal Sympathetic Denervation in Patients With Treatment-Resistant Hypertension (The Symplicity HTN-2 Trial): A Randomised Controlled Trial", The Lancet, 376(9756): 1903-1909, Published Online Nov. 17, 2010.

Symplicity HTN-2 Investigators "Renal Sympathetic Denervation in Patients With Treatment-Resistant Hypertension (The Symplicity HTN-2 Trial): A Randomised Controlled Trial", The Lancet, 376: 1903-1909, Dec. 4, 2010.

Szabo "Diagnostic Ultrasound Imaging Inside Out", Academic Press Series in Biomedical Engineering, 2004.

Techavipoo et al. "Temperature Dependence of Ultrasonic Propagation Speed and Attenuation in Excised Canine Liver Tissue Measured Using Transmitted and Reflected Pulses", Journal of the Acoustical Society of America, 115(6): 2859-2865, Jun. 2004.

Thenappan et al. "Beta-Blocker Therapy Is Not Associated With Adverse Outcomes in Patients With Pulmonary Arterial Hypertension. A Propensity Score Analysis", Circulation Heart Failure, 7(6): 903-910, Published Online Oct. 2, 2014.

Tibshirani "Regression Shrinkage and Selction Via the Lasso: A Retrospective", Journal of the Royal Statistical Society, Series B: Statistical Methodology, 73(Pt.3): 273-282, 2011.

Tibshirani "Regression Shrinkage and Selection Via the Lasso", Journal of the Royal Statistical Society, Series B: Methodological, 58(1): 267-288, 1996.

Toorop et al. "Clinical Results of Carotid Denervation by Adventitial Stripping in Caotid Sinus Syndrome", Europan Journal of Vascular and Endovascular Syndrome, 39: 146-152, 2010.

Tyreus et al. "Two-Dimensional Acoustic Attenuation Mapping of High-Temperature Interstitial Ultrasound Lesions", Physics in Medicine and Biology, 49: 533-546, 2004.

Van Albada et al. "Biological Serum Markers in the Managment of Pediatric Pulmonary Arterial Hypertension", Pediatric Research, 63(3): 321-327, Mar. 2008.

Van Campen et al. "Bisoprolol in Idiopathic Pulmonary Arterial Hypertension: an Explorative Study", European Respiratory Journal, 48: 787-796, 2016.

Velez-Roa et al. "Increased Sympathetic Nerve Activity in Pulmonary Artery Hypertension", Circulation, 110(10): 1308-1312, Sep. 7, 2004.

Verloop et al. "The Effects of Renal Denervation on Renal Haemodynamics", Interventions for Hypertenison & Heart Failure, Abstracts of EuroPCR & AsiaPCR/SingLIVE 2013, May 21, 2013.

Virmani "Translation Medicine and Renal Denervation: Pre-Clinical Animal Models and Histoanatomy", CVPath Institute, Gaithersburg, MD, USA, PowerPoint Presentation.

Voskuil et al. "Percutaneous Renal Denervation for the Treatment of Resistant Essential Hypertension; The First Dutch Experience", Netherlands Heart Journal, 19(7-8): 319-323, Aug. 2011.

Warwick et al. "Trackless Lesions in Nervous Tissues Produced by High Intensity Focused Ultrsound (High-Frequency Mechanical Waves)", Journal of Anatomy, 102(3): 387-405, 1968.

Wei-Feng "New Theories and New Technologies for Cardiovascular Diseases", People's Military Medical Press, 324: 3P., 2015. ( Chinese only).

Wikswo Jr. et al. "Magnetic Field of A Nerve Impulse: First Measurements", Science, 208: 53-55, Apr. 4, 1980.

Wilcox "Resistant Hypertension and the Role of the Sympathetic Nervous System", Medtronic, 30 P.

Williams et al. "Laser Energy Source in Surgical Atrial Fibrillation Ablation: Preclinical Experience", The Annals of Thoracic Surgery, 82: 2260-2264, 2006.

Witkowski "Future Perspective in Renal Denervation: Congestive Heart Failure, Insulin Resistance and Sleep Apnea", Innovations in Cardiovascular Interventions, ICI Meeting 2011, Tel Aviv, Israel, Dec. 4-6, 2011, 23 P., 2011.

Witkowski et al. "Effects of Renal Sympathetic Denervation on Blood Pressure, Sleep Apnea Course, and Glycemic Control in Patients With Resistant Hypertension and Sleep Apnea", Hypertension, 58(4): 559-565, Oct. 2011.

Witkowski et al. "Effects of Renal Sympathetic Denervation on Blood Pressure, Sleep Apnea Course, and Glycemic Control in Patients With Resistant Hypertension and Sleep Apnea", Hypertension, 58: 559-565, Aug. 15, 2011.

Witte et al. "Imaging Current Flow in Lobster Nerve Cord Using the Acoustoelectric Effect", Applied Physics Letters, 90: 163902-1-163902-3, 2007.

Wolf-De Jonge et al. "25 Years of Laser Assisted Vascular Anastomosis (LAVA): What Have We Learned?", European Journal of Vascular and Endovascular Surgery, 27(5): 466-476, May 2004.

Worthington et al. "Changes in Ultrasound Properties of Porcine Kidney Tissue During Heating", Ultrasound in Medicine & Biology, 27(5): 673-682, 2001.

Worthington et al. "Ultrasound Properties of Human Prostate Tissue During Heating", Ultrsound in Medicine & Biology, 28(10): 1311-1318, 2002.

Wright "On A Relationship Between the Arrhenius Parameters From Thermal Damage Studies", Transactions of the ASME, Technical Brief, Journal of Biomechanical Engineering, 125(2): 300-304, Apr. 9, 2003.

Wu et al. "A Quality Control Program for MR-Guided Focused Ultrasound Ablation Therapy", Journal of Applied Clinical Medical Physics, 3(2): 162-167, Spring 2002.

Wu et al. "Noninvasive Cardiac Arrhythmia Therapy Using High-Intensity Focused Ultrasound (HIFU) Ablation", International Journal of Cardiology, 166(2): e28-e30, Available Online Feb. 26, 2013.

Xu et al. "Experimental Nerve Thermal Injury", Brain, 117: 375-384, 1994.

Zeller "Percutaneous Renal Denervation System. The New Ultrasound Solution for the Mangament of Hypertension", Paradise Ultrasound Denervation System, ReCor Medical, 27 P., 2013.

Zhang et al. "Pulmonary Arterial Hypertension: Pharmacologic Therapies and Potential Pulmonary Artery Denervation Treatment", EuroIntervention, XP009524288, 9(Suppl.R): R149-R154, May 2013.

Zhou et al. "Pulmonary Artery Denervation Attenuates Pulmonary Arterial Remodeling in Dogs With Pulmonary Arterial Hypertension Induced by Dehydrogenized Monocrotaline", JACC: Cardiovascular Interventions, 8(15): 2013-2023, Dec. 28, 2015.

Restriction Official Action Dated Dec. 14, 2022 from the US Patent and Trademark Office Re. U.S. Appl. No. 17/187,813. (8 pages).

Communication Pursuant to Article 94(3) EPC Dated Mar. 1, 2023 From the European Patent Office Re. Application No. 18771348.2 (6 Pages).

Cheever "An Overview of Pulmonary Arterial Hypertension: Risks, Pathogenesis, Clinical Manifestations, and Management", The Journal of Cardiovascular Nursing 20(2): 108-116, Mar. 2005. Abstract.

Interview Summary Dated May 1, 2024 from the US Patent and Trademark Office Re. U.S. Appl. No. 16/494,322. (2 pages).

(56)        References Cited

OTHER PUBLICATIONS

Notice of Allowance Dated Apr. 3, 2023 from US Patent and Trademark Office Re. U.S. Appl. No. 16/451,087. (9 pages).
Notice of Allowance Dated Sep. 17, 2024 from the US Patent and Trademark Office Re. U.S. Appl. No. 17/752,879. (12 pages).
Official Action Dated Apr. 3, 2023 from the US Patent and Trademark Office Re. U.S. Appl. No. 17/187,813. (55 pages).
Official Action Dated Mar. 7, 2024 from the US Patent and Trademark Office Re. U.S. Appl. No. 17/719,412. (57 pages).
Official Action Dated Nov. 14, 2023 from the US Patent and Trademark Office Re. U.S. Appl. No. 17/187,813. (15 pages).
Official Action Dated Jun. 23, 2023 From the US Patent and Trademark Office Re. U.S. Appl. No. 17/752,879. (53 Pages).
Official Action Dated Jan. 24, 2024 From the US Patent and Trademark Office Re. U.S. Appl. No. 16/439,816. (16 Pages).
Official Action Dated Jan. 24, 2024 From the US Patent and Trademark Office Re. U.S. Appl. No. 17/752,879. (15 pages).

Official Action Dated May 24, 2023 from the US Patent and Trademark Office Re. U.S. Appl. No. 16/494,322. (113 pages).
Official Action Dated Apr. 25, 2024 from the US Patent and Trademark Office Re. U.S. Appl. No. 18/235,904. (46 pages).
Official Action Dated Jun. 26, 2023 from the US Patent and Trademark Office Re. U.S. Appl. No. 16/439,816. (59 pages).
Official Action Dated Aug. 28, 2024 from the US Patent and Trademark Office Re. U.S. Appl. No. 16/494,322. (50 pages).
Restriction Official Action Dated Aug. 1, 2023 from the US Patent and Trademark Office Re. U.S. Appl. No. 17/719,412. (8 pages).
Communication Pursuant to Article 94(3) EPC Dated Mar. 11, 2025 From the European Patent Office Re. Application No. 18771348.2 (8 Pages).
Notice of Allowance Dated Mar. 19, 2025 from the US Patent and Trademark Office Re. U.S. Appl. No. 18/235,904. (10 pages).
Official Action Dated Apr. 11, 2025 from the US Patent and Trademark Office Re. U.S. Appl. No. 16/494,322. (38 pages).
Official Action Dated Mar. 14, 2025 from the US Patent and Trademark Office Re. U.S. Appl. No. 16/439,816. (28 Pages).

* cited by examiner

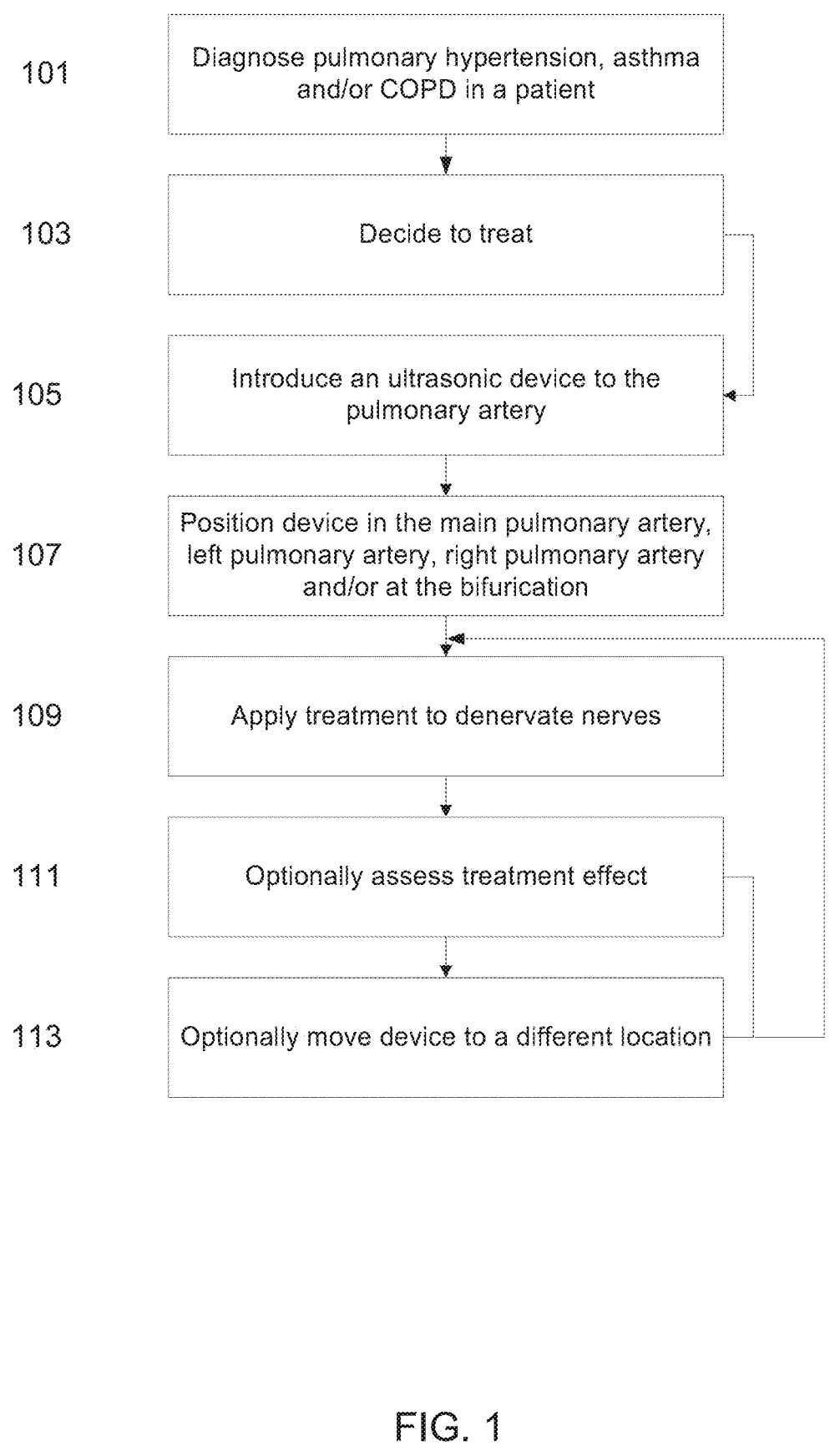

| 101 | Diagnose pulmonary hypertension, asthma and/or COPD in a patient |
|---|---|
| 103 | Decide to treat |
| 105 | Introduce an ultrasonic device to the pulmonary artery |
| 107 | Position device in the main pulmonary artery, left pulmonary artery, right pulmonary artery and/or at the bifurication |
| 109 | Apply treatment to denervate nerves |
| 111 | Optionally assess treatment effect |
| 113 | Optionally move device to a different location |

FIG. 1

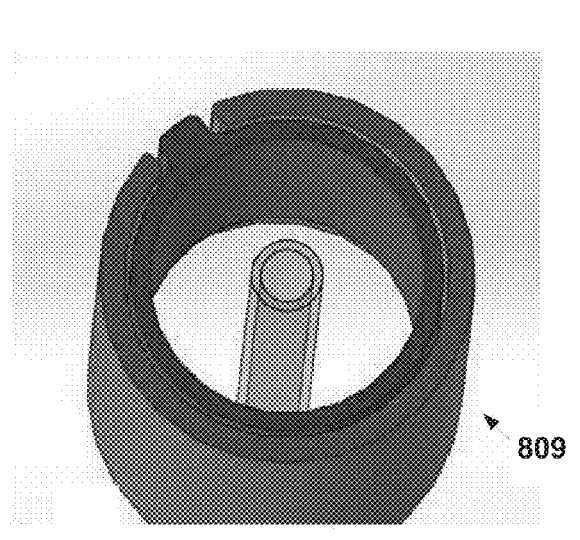
FIG. 8D2
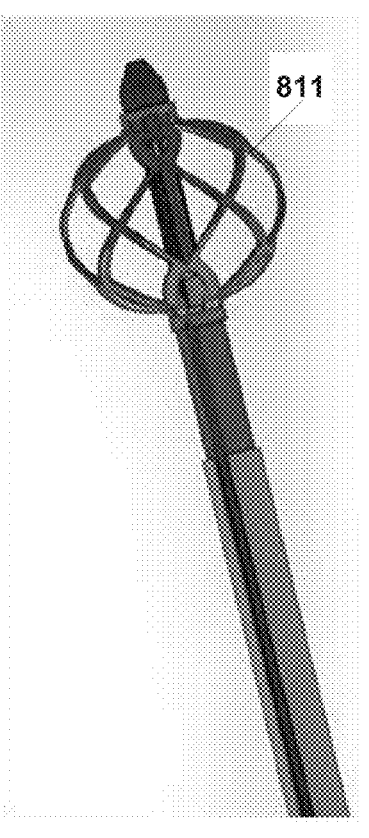
FIG. 8D1
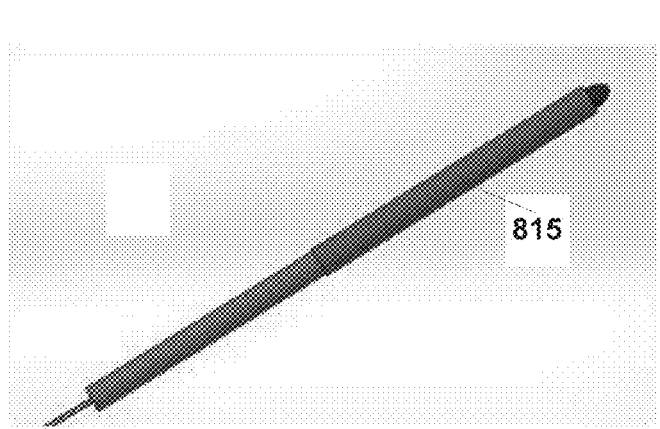
FIG. 8E2
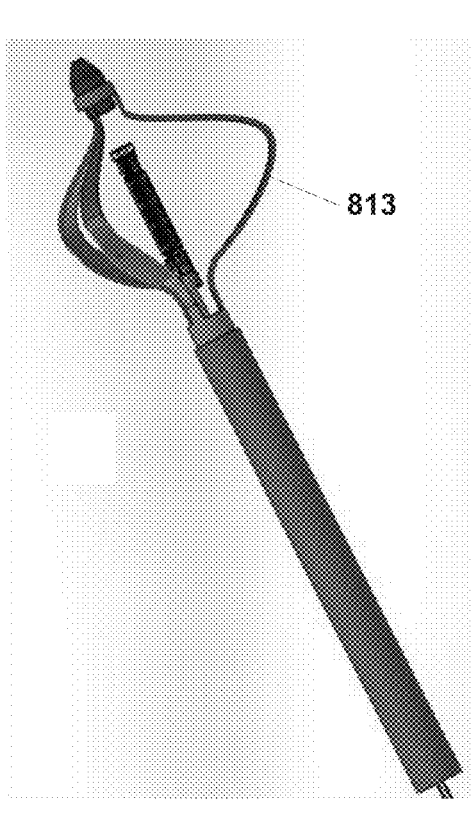
FIG. 8E1

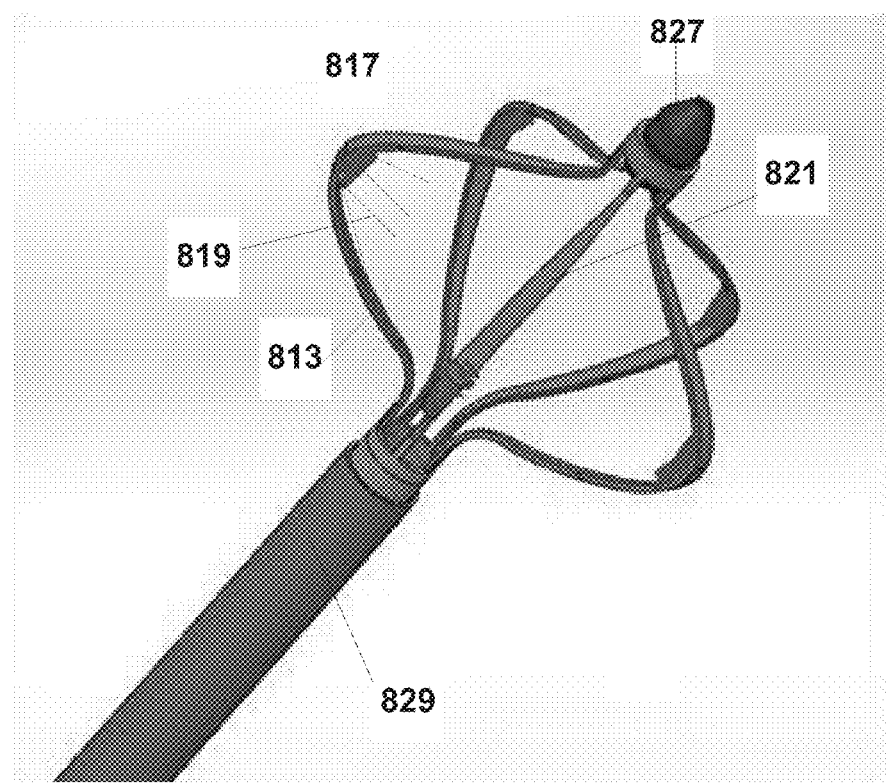
FIG. 8F1
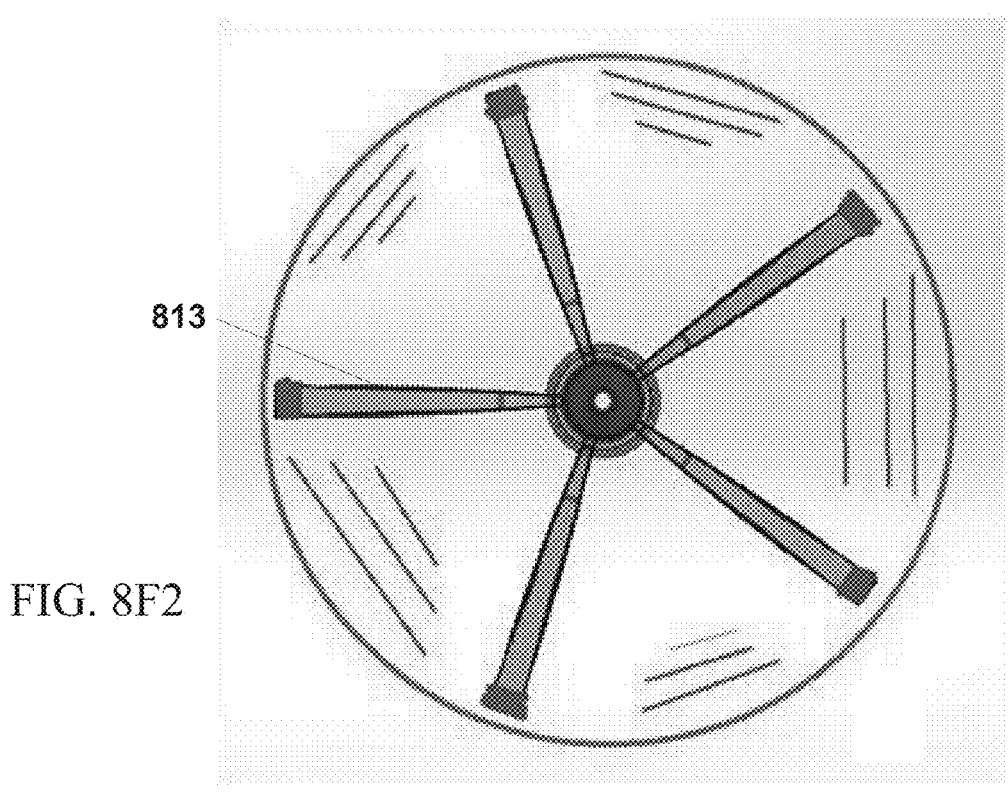
FIG. 8F2

901    Diagnose pulmonary hypertension, asthma and/or COPD in a patient

903    Decide to treat

905    Introduce an ultrasonic device comprising a fluid circulation system to the trachea 907    Position device in the trachea 909    Apply treatment to denervate nerves 911    Optionally assess treatment effect 913    Optionally move device to a different location FIG. 10A
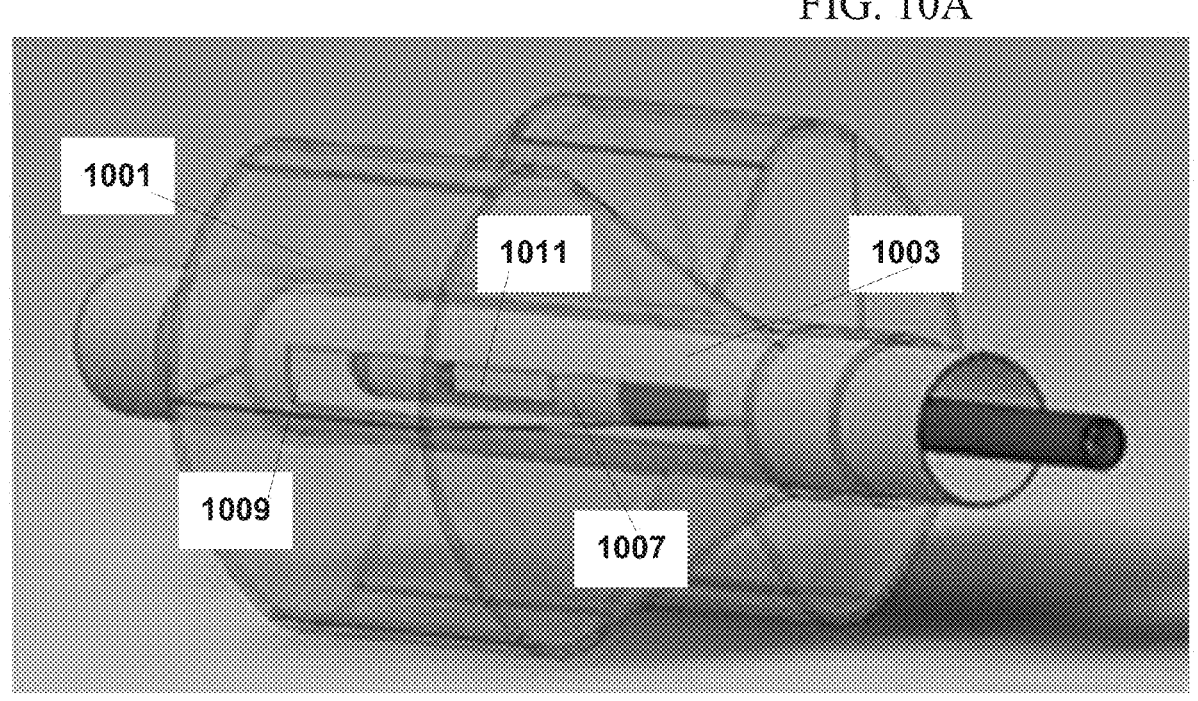
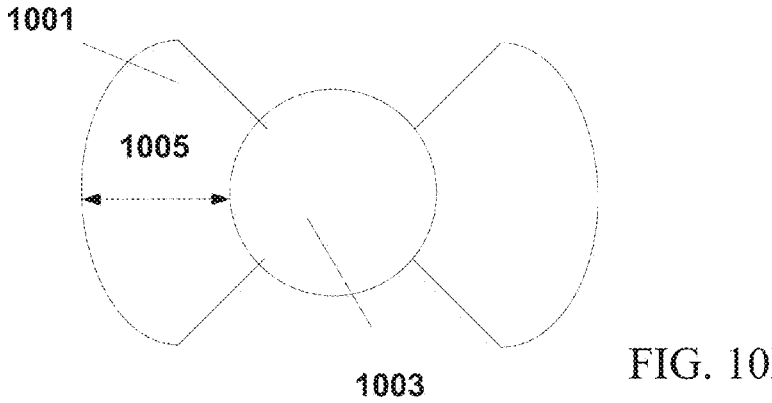
FIG. 10B

Figure 12:
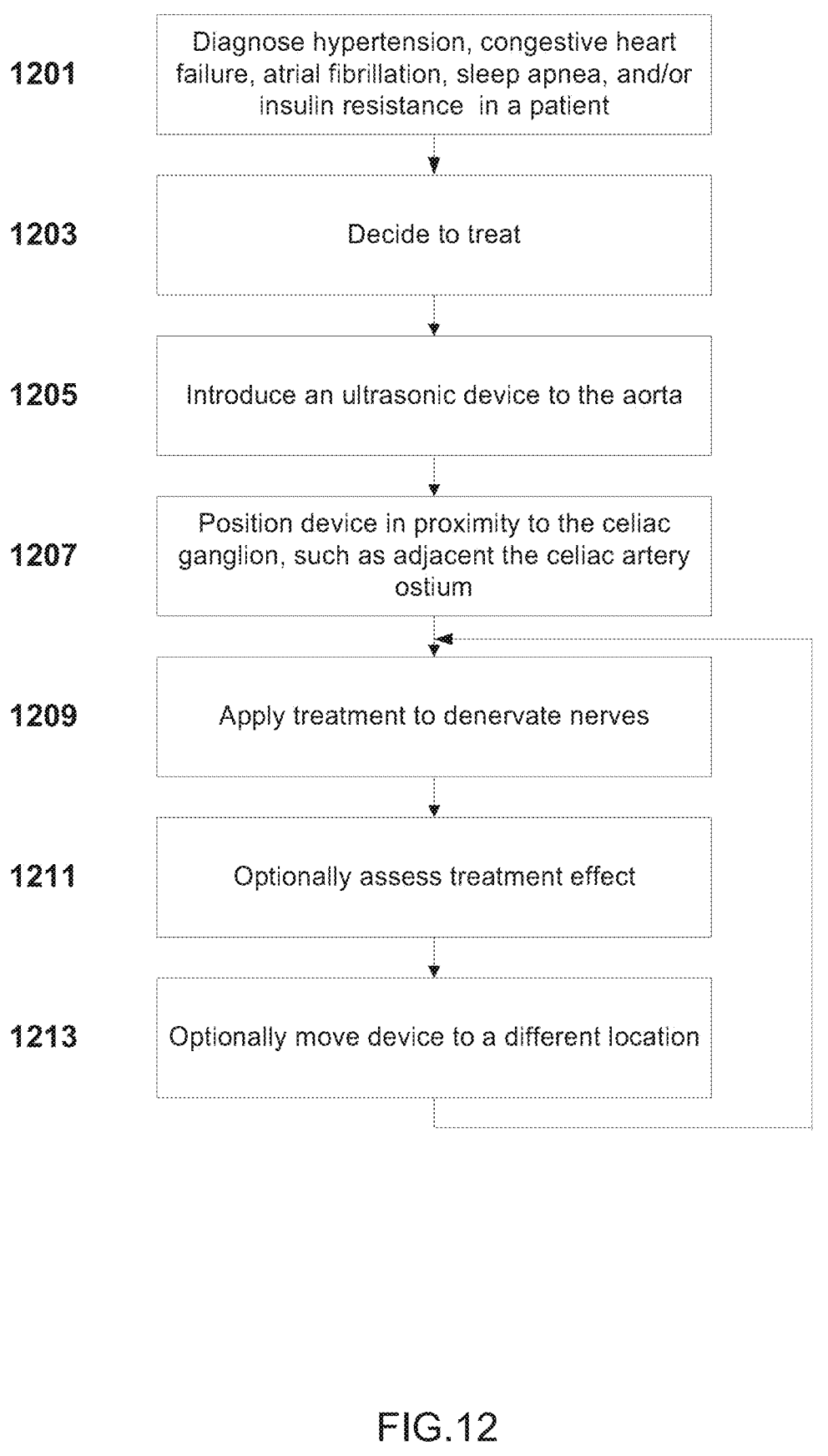

1201    Diagnose hypertension, congestive heart failure, atrial fibrillation, sleep apnea, and/or insulin resistance in a patient

1203    Decide to treat

1205    Introduce an ultrasonic device to the aorta

1207    Position device in proximity to the celiac ganglion, such as adjacent the celiac artery ostium

1209    Apply treatment to denervate nerves

1211    Optionally assess treatment effect

1213    Optionally move device to a different location

DEVICES AND METHODS FOR PULMONARY HYPERTENSION TREATMENT

RELATED APPLICATIONS

This application is a division of U.S. patent application Ser. No. 15/529,137 filed on May 24, 2017, which is a National Phase of PCT Patent Application No. PCT/IL2015/051145 having International Filing Date of Nov. 25, 2015, which claims the benefit of priority under 35 USC § 119(e) of U.S. Provisional Patent Application No. 62/084,782 filed on Nov. 26, 2014. The contents of the above applications are all incorporated by reference as if fully set forth herein in their entirety.

FIELD AND BACKGROUND OF THE INVENTION

The present invention, in some embodiments thereof, relates to hypertension treatment and, more particularly, but not exclusively, to treatment of pulmonary hypertension and associated conditions.

U.S. Patent Application Publication No. US20130204068 to Gnanashanmugam et al. teaches "A method is described for decreasing activity of at least one sympathetic nerve, nerve fiber or neuron innervating at least one blood vessel in the pulmonary vasculature of a patient to ameliorate pulmonary hypertension. In one embodiment, the method may involve advancing an intravascular treatment device to a target location in a target blood vessel within the pulmonary vasculature of the patient and using the treatment device to decrease activity of at least one sympathetic nerve, nerve fiber or neuron innervating the target blood vessel at or near the target location to ameliorate pulmonary hypertension".

SUMMARY OF THE INVENTION

According to an aspect of some embodiments there is provided method for selectively modifying nerve activity without causing substantial damage to non-targeted tissue, comprising: introducing a catheter device comprising one or more ultrasonic transceivers to the pulmonary artery lumen; receiving, using the one or more ultrasonic transceivers, echo signals reflected from the non-targeted tissue following emission of ultrasound energy by the one or more ultrasonic transceivers; analyzing the received echo signals to identify at least one of a type and location of the non-targeted tissue relative to the one or more ultrasonic transceivers; and emitting ultrasound energy from the one or more ultrasonic transceivers in accordance with the analyzing, to modify nerve activity without substantially damaging the identified non-targeted tissue. In some embodiments, the method further comprises selecting at least one of a location of the transceivers, an orientation of the transceivers, and a denervation treatment profile according to the analyzing. In some embodiments, the non-targeted tissue comprises one or more of: lung, trachea, vagus, lymph, bronchi. In some embodiments, analyzing comprises determining a distance between the non-targeted tissue and the one or more transceivers. In some embodiments, analyzing comprises identifying targeted tissue. In some embodiments, emitting comprises targeting nerve tissue at a distance ranging between 0.5 mm to 10 mm from an inner wall of the artery lumen. In some embodiments, ultrasound energy is non-focused energy applied at an intensity sufficient to cause at least semi-permanent nerve modification to targeted tissue. In some embodiments, the method further comprises diagnosing the patient with one or more of pulmonary hypertension, asthma and/or COPD, and selecting a denervation treatment profile in accordance with the diagnosing. In some embodiments, the method further comprises collecting feedback and modifying the emitting based on the feedback by measuring one or more physiological parameters before and after the emitting. In some embodiments, one or more physiological parameters include one or more of heart rate, pulmonary artery diameter, bronchi diameter, cardiac output, respiratory rate, lung volumes, arterial constriction, pulmonary artery pressure, blood flow, artery stiffness. In some embodiments, the pulmonary artery diameter is estimated by analyzing echo signals reflected by walls of the artery and received by the one or more ultrasonic transceivers. In some embodiments, measuring comprises stimulating the sympathetic nervous system, and measuring the physiological parameter in response to the stimulation.

According to an aspect of some embodiments there is provided a method for selectively targeting nerve tissue, comprising: introducing a catheter comprising one or more ultrasonic transceivers to the pulmonary artery lumen; selecting to damage only nerves that are not coated by myelin; emitting ultrasound energy at a frequency, intensity and duration sufficient to damage only nerves that are not coated by myelin, by producing a predetermined temperature profile in the treated tissue, the temperature profile ranging between 47-57 degrees C. In some embodiments, the method comprises modifying at least one of the frequency, intensity and duration of the energy to produce a temperature profile ranging between 58-70 degrees C. in the treated tissue, to selectively damage both myelin coated nerves and non-coated nerves. In some embodiments, the method further comprises assessing a bronchial reaction to the emitting as feedback to the targeting, and modifying at least one of the frequency, intensity and duration of the energy in accordance with the bronchial reaction. In some embodiments, the method comprises positioning the one or more ultrasonic transceivers away from a wall of the pulmonary artery lumen to allow blood to flow between the transceivers and the wall.

According to an aspect of some embodiments there is provided an ultrasonic catheter for selectively targeting nerve tissue from a pulmonary artery lumen, comprising: a head configured at a distal end of the catheter, the head comprising one or more ultrasonic transceivers, the transceivers configured to emit non-focused ultrasound energy; a controller configured to select one or more of frequency, intensity and duration of the non-focused ultrasound energy emitted by the transceivers to selectively damage only nerves that are not coated by myelin. In some embodiments, the controller is configured to select one or more of the frequency, intensity and duration of the non-focused ultrasound energy emitted by the transceivers to selectively damage both myelin coated nerves and non-coated nerves.

According to an aspect of some embodiments there is provided an ultrasonic catheter device comprising: an elongated shaft; a head configured at a distal portion of the shaft, the head comprising a plurality of leaflets expandable in a radially outward direction relative to the shaft, each of the leaflets comprised of a rod-like element bendable into an elbow shaped configuration; and a plurality of ultrasonic transceivers, each transceiver mounted onto one of the expandable leaflets. In some embodiments, each of the transceivers comprises an energy emitting surface and an opposing surface, the opposing surface coupled to the leaflet to position the energy emitting surface to face a central direction. In some embodiments, a distal tip of the shaft is retractable for expanding the leaflets relative to the shaft and advanceable for contracting the leaflets closer to the shaft. In some embodiments, the transceiver is mounted onto the leaflet at the elbow shaped bend of the leaflet.

According to an aspect of some embodiments there is provided an ultrasonic catheter device for modifying nerve activity from an air filled lumen, comprising: a head comprising one or more ultrasonic transceivers, the transceivers configured to emit energy having parameters suitable to modify nerve tissue in target tissue; a balloon arrangement in which fluid is circulated, the balloon arrangement comprising at least an inner balloon, surrounding the transceivers, and an outer balloon, surrounding the inner balloon, wherein cold fluid is circulated in the inner balloon for cooling the one or more transceivers, and warm fluid is circulated in the outer balloon for enhancing a thermal heating effect of energy emitted by the transceivers, to effectively increase a depth of the produced ultrasonic field in the target tissue. In some embodiments, cold fluid and the warm fluid are the same fluid, the cold fluid heated as a result of cooling the transceivers and circulated as the warm fluid to enhance the thermal heating effect of the emitted energy. In some embodiments, the balloon arrangement comprises two or more balloons which when inflated cover only portions of the head, and do not surround the head circumferentially. In some embodiments, emitting surfaces of the one or more transceivers are exposed in between the balloons. In some embodiments, the balloon arrangement is configured to push the one or more transceivers away from a wall of the lumen when inflated. In some embodiments, the air filled lumen is the trachea.

According to an aspect of some embodiments there is provided a method for modifying nerve activity, comprising introducing a catheter device comprising at least one ultrasonic transceiver to the aorta; engaging the celiac artery ostium using an elongated tool extending from the catheter; and emitting ultrasound energy to modify nerve activity of the celiac ganglion. In some embodiments, the method comprises selecting a position of the at least one transceiver in the aorta in accordance with a location of the celiac artery ostium. In some embodiments, the method comprises positioning and orienting the at least one transceiver relative to the celiac artery ostium using the elongated tool.

According to an aspect of some embodiments there is provided a kit for modifying nerve activity of the celiac ganglion, comprising a catheter comprising at least one ultrasonic transceiver; an elongated tool extendible from the catheter, the tool long enough to engage the celiac artery ostium, the tool comprising a curvature suitable to direct the ultrasonic transceiver towards the celiac artery ostium when the tool engages the ostium. In some embodiments, the elongated tool comprises a rod insertable through a cannulated shaft of the catheter and extendible from a distal opening of the catheter shaft.

According to an aspect of some embodiments there is provided an ultrasonic catheter system for modifying nerve activity, comprising a catheter comprising a head at its distal end, the head comprising one or more ultrasonic emitters, the emitters configured to emit energy suitable for modifying nerve activity; a tool usable with the catheter, the tool comprising: a supporting section; an emitter-positioning section configured distally to the supporting section; wherein the catheter is cannulated to be advanced over the tool into a blood vessel, until the emitters are axially aligned with the emitter positioning section of the tool; wherein the tool is shaped and sized such that the supporting section leans against a vessel wall opposite the wall to be treated, setting a location of the emitter positioning section at a predetermined radial distance from the vessel wall to be treated. In some embodiments, the tool comprises a sigmoid shaped curvature, so that when the tool is within the blood vessel, the emitter-positioning section is located away from a central longitudinal axis of the vessel, at an angle to the longitudinal axis. In some embodiments, an arrangement of the emitters on the catheter head is selected so that when the head is advanced over the emitter-positioning section, an emitting surface of at least one of the emitters faces the vessel wall to be treated. In some embodiments, at least one of advancement of the catheter over the tool, and axial rotation of the tool when the catheter is positioned over it provide for treating the blood vessel circumferentially. In some embodiments, the tool is a guide wire, the guide wire comprising a spiral shape, the spiral having a cross sectional diameter which is no more than 10% smaller than a cross sectional diameter of the lumen. In some embodiments, the tool is a guide wire the guide wire comprising a Z shape, tracing a jagged path between the opposite walls of the body lumen so that when the guide wire is rotated, at least the one or more emitters are maintained at the predetermined radial distance from the lumen wall. In some embodiments, catheter is positionable over the tool such that the head is proximal to at least one of the supporting section, and the emitter-positioning section.

According to an aspect of some embodiments there is provided an ultrasonic catheter for modifying nerve activity from within a blood vessel, comprising a shaft comprising at least one curved portion; a head configured at a distal end of the shaft, the head comprising one or more ultrasonic emitters, the emitters configured to emit energy suitable for modifying nerve activity; wherein the curved portion of the shaft comprises a sigmoid-shape curvature which pushes the head away from one wall of the blood vessel and in proximity to an opposite wall of the blood vessel. In some embodiments, the sigmoid shaped shaft portion distances the head away from a central longitudinal axis of the vessel, at an angle to the longitudinal axis. In some embodiments, an arrangement of the emitters on the catheter head is selected so that an emitting surface of at least one of the emitters faces the vessel wall to be treated. In some embodiments, axial rotation of the catheter provides for treating the blood vessel circumferentially. In some embodiments, the sigmoid shaped shaft portion comprises a cross sectional diameter which is no more than 10% smaller than a cross sectional diameter of the blood vessel.

According to an aspect of some embodiments there is provided a method for advancing an ultrasonic catheter within a body lumen while keeping at least emitters of the catheter at a predetermined radial distance range from the walls of the body lumen, comprising delivering a catheter comprising one or more ultrasonic emitters over a guide wire into a body lumen, the guide wire comprising a curvature selected in accordance with a cross sectional profile of the body lumen; advancing the catheter over the guide wire within the lumen, while the emitters are maintained within the predetermined radial distance range from a wall of the body lumen. In some embodiments, the radial distance range is between 1 mm from the wall of the body lumen, and 1 mm from a central longitudinal axis of the body lumen. In some embodiments, the cross sectional profile comprises a diameter of the body lumen, and the curvature of the guide wire comprises a diameter at least 5% shorter than the lumen diameter. In some embodiments, the catheter is advanced over the guide wire to a position in which the emitters are located proximally to the curvature of the guide wire. In some embodiments, the catheter comprises a single ultrasonic emitter, and wherein the method further comprises rotating the guide wire to treat the body lumen circumferentially.

According to an aspect of some embodiments there is provided an ultrasonic catheter structured to reduce movement of a distal portion of the catheter when at least a proximal portion of the catheter is subjected to movement resulting from heart pulsation, comprising a head configured at a distal end of the catheter, the head comprising one or more ultrasonic emitters configured to emit energy to modify nerve activity; a shaft comprising at least one axial decoupling at a distance of no more than 10 cm away from the head. In some embodiments, the axial decoupling is provided by a coil configured to dampen movement of the head when a proximal portion of the catheter is moved due to heart pulsation. In some embodiments, the catheter is sized for insertion into the pulmonary artery, the distance between the head and the axial decoupling selected so that when the head is positioned within the pulmonary artery, the axial decoupling is between the heart and the catheter head.

According to an aspect of some embodiments there is provided a method for treating pulmonary hypertension, comprising inserting a catheter comprising one or more ultrasonic emitters into the pulmonary artery; emitting nonfocused ultrasound energy to thermally damage nerve tissue; measuring pulmonary arterial pressure; modifying the emitting in accordance with the pulmonary arterial pressure. In some embodiments, the catheter is equipped with one or more pressure sensors, and the measuring of pulmonary arterial pressure is performed using the one or more pressure sensors. In some embodiments, the method further comprises measuring one or more of cardiac output, systemic pressure. In some embodiments, emitting is performed at a distance of at least 1 mm from the wall of the pulmonary artery, allowing blood to flow between the emitter and the wall.

According to an aspect of some embodiments there is provided a method for modifying nerve activity from within the pulmonary artery, comprising introducing a catheter comprising an ultrasonic emitter into the pulmonary artery; emitting ultrasound energy having parameters suitable for thermally damaging nerve tissue; axially rotating the catheter to emit the energy circumferentially towards the walls of the artery.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a flowchart of a method for treating nerves by positioning an ultrasonic device in the pulmonary artery, according to some embodiments of the invention;

FIG. 2 is a schematic illustration of neural networks and organs in the vicinity of a pulmonary artery, in a human thorax;

FIGS. 3A-3B illustrate an ultrasonic device positioned within a pulmonary artery, according to some embodiments of the invention;

FIGS. 4A-4B illustrate an ultrasonic catheter device, according to some embodiments of the invention;

FIGS. 5A-5B illustrate an ultrasonic device used with a distancing device, according to some embodiments of the invention;

FIGS. 6A-6B are a flowchart of various aspects of selective treatment (6A), and a schematic graph of selectively treating different types of nerve tissue (6B), according to some embodiments of the invention;

FIG. 7 is a flowchart of an exemplary feedback loop associated with a denervation procedure, according to some embodiments of the invention;

Figure 9:
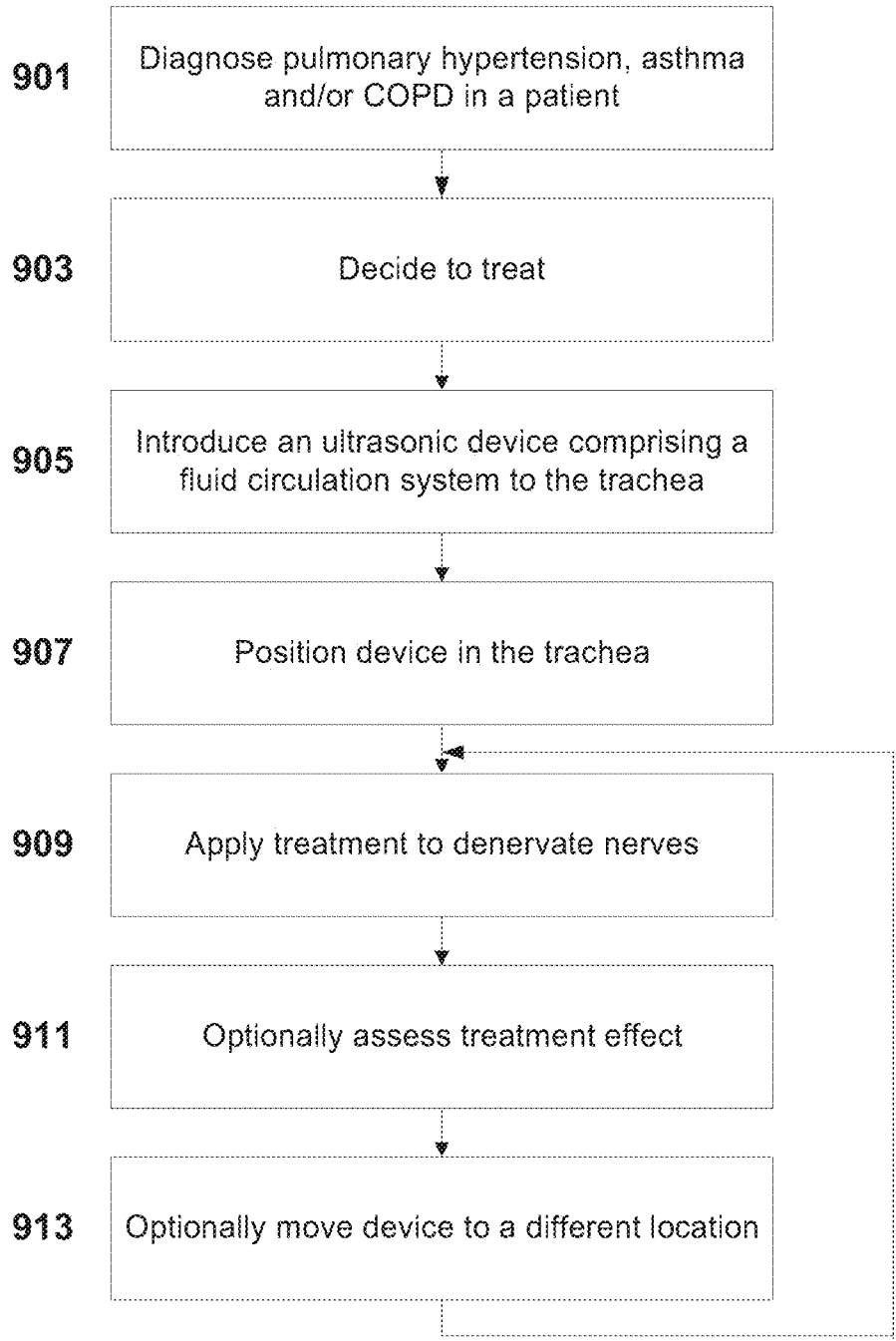
Figure 11A:
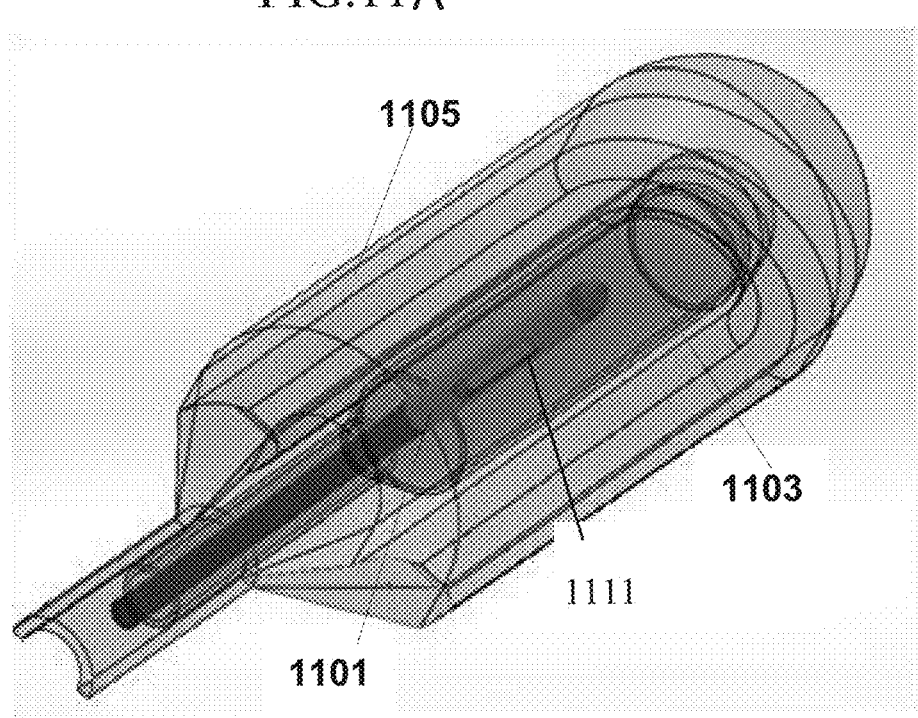
Figure 11B:
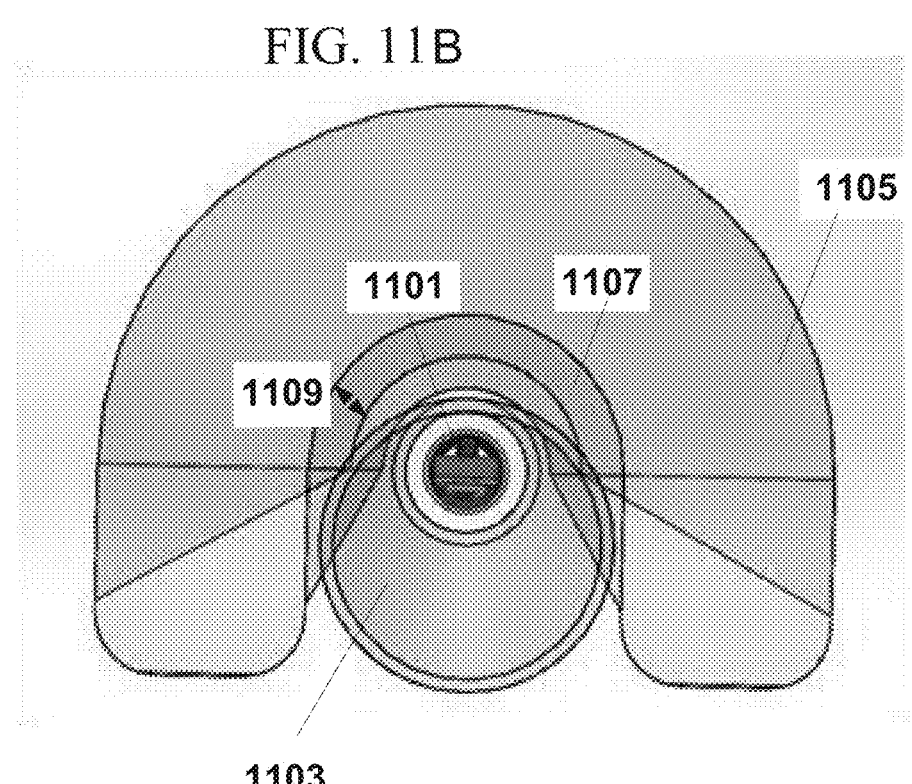
Figure 13:
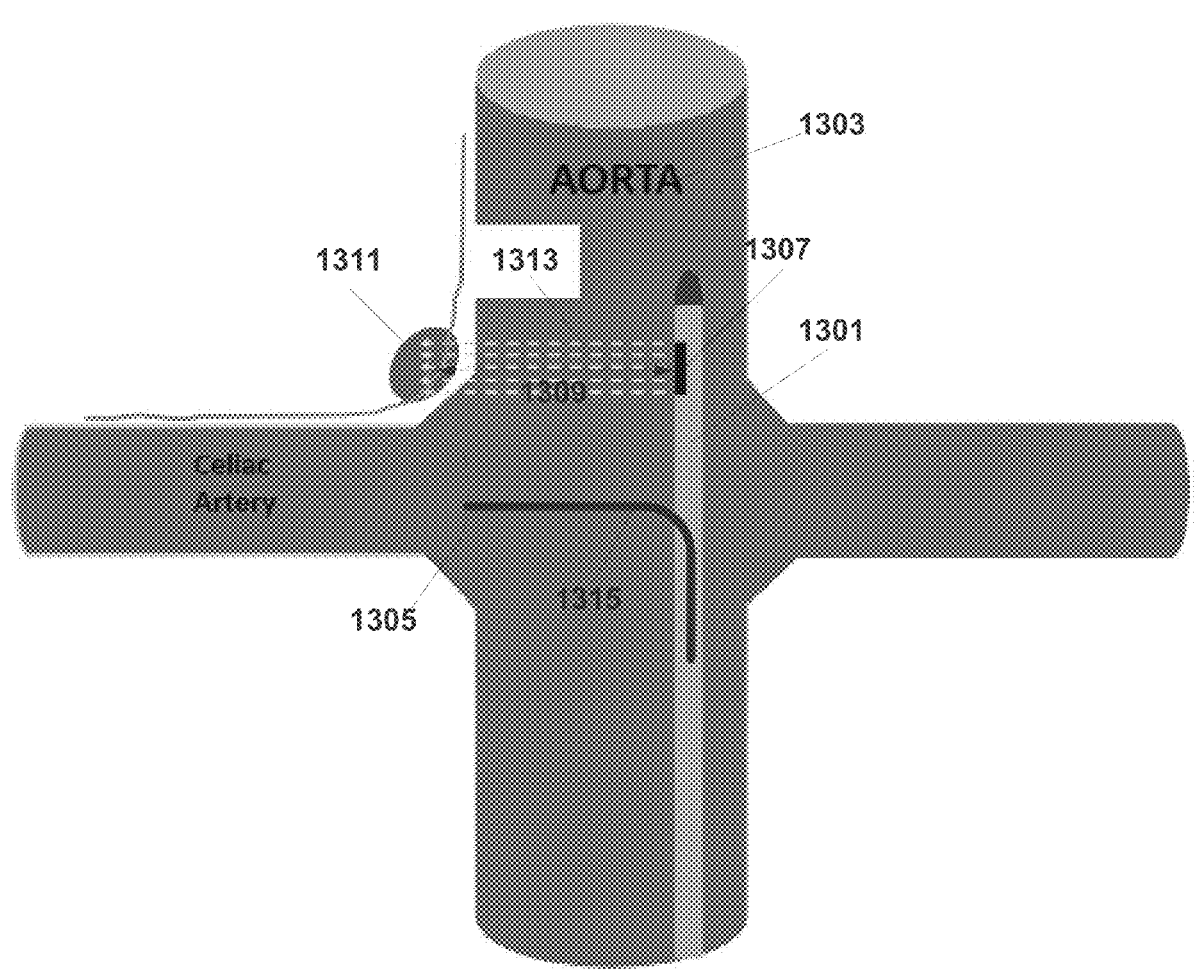
Figure 19:
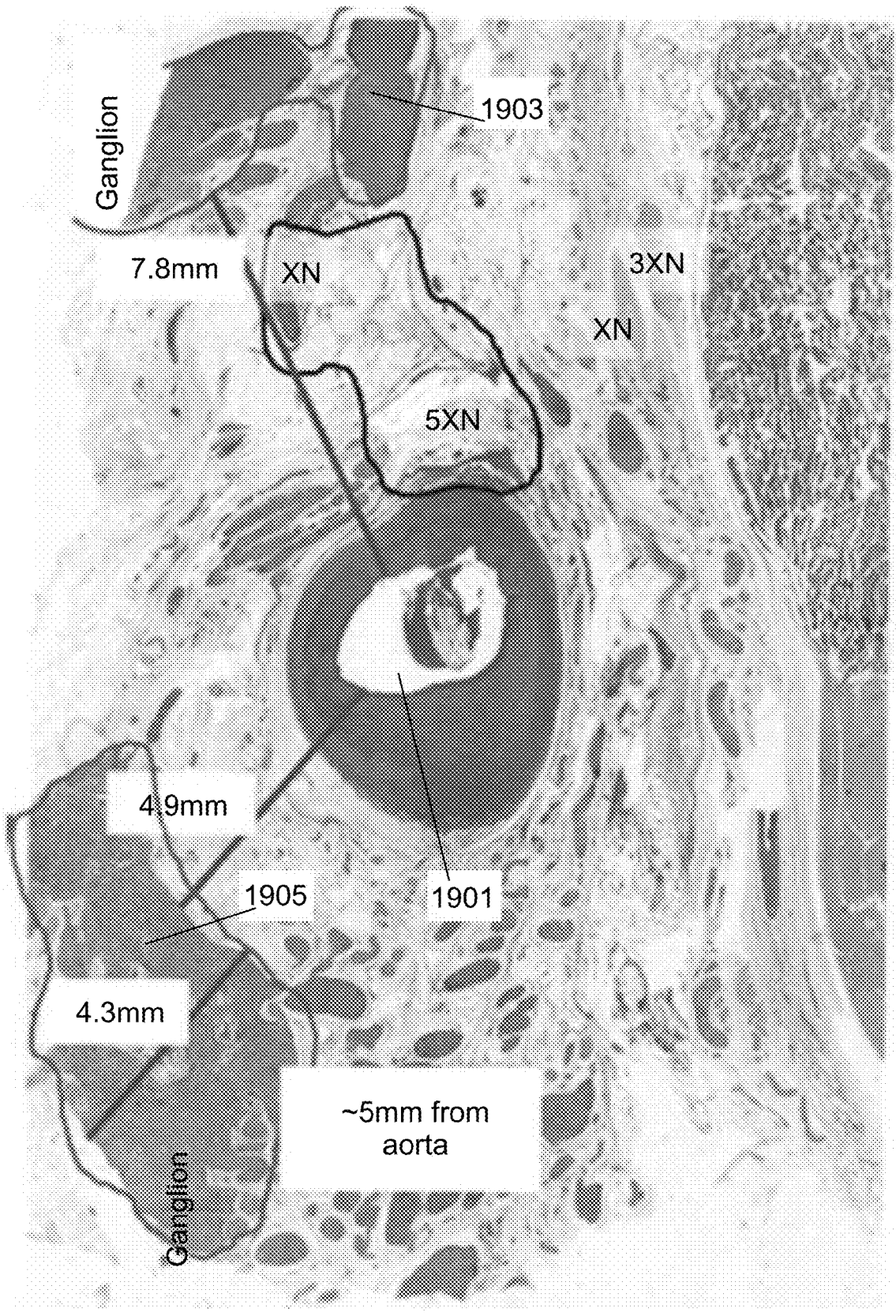

FIGS. 8A, 8B, 8C, 8D1, 8D2, 8E1, 8E2, 8F1 and 8F2 are various configurations of an ultrasonic catheter device, according to some embodiments of the invention;

FIG. 9 is a flowchart of a method for treating nerves by positioning an ultrasonic device in the trachea, according to some embodiments of the invention;

FIGS. 10A-10B show an ultrasonic catheter equipped with one or more balloons, according to some embodiments of the invention;

FIGS. 11A-11B shows an ultrasonic catheter equipped with a multiple balloon assembly for providing heating and/or cooling fluid circulation, according to some embodiments of the invention;

FIG. 12 is a flowchart of a method for treating the celiac ganglia by positioning an ultrasonic device in the aorta, according to some embodiments of the invention;

FIG. 13 illustrates an ultrasonic device positioned within the aorta to denervate nerve tissue of the celiac ganglia, according to some embodiments of the invention;

Figure 14:
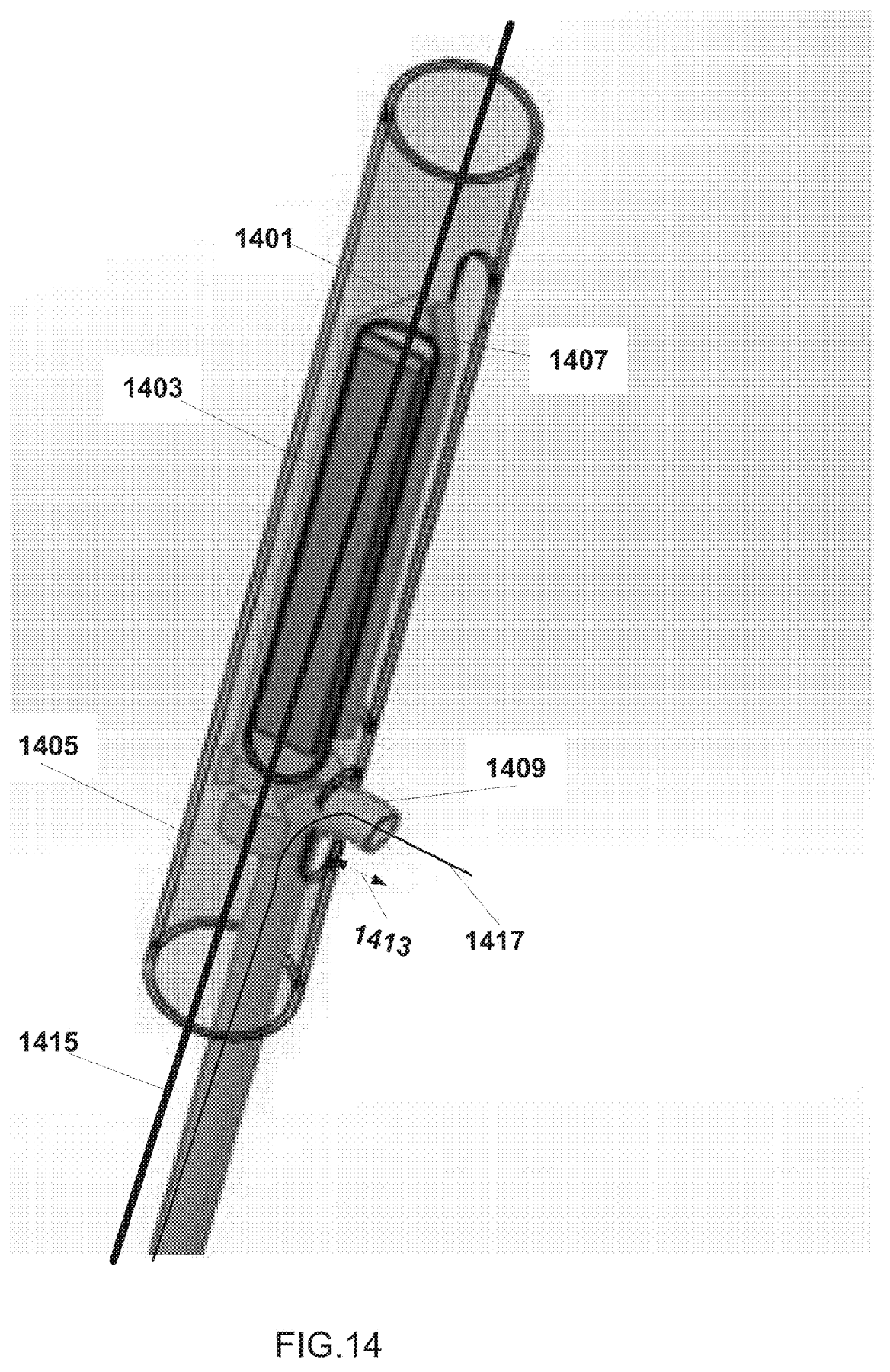

FIG. 14 illustrates an ultrasonic device comprising an element adapted for distancing the device away from a vessel wall and/or fixating the device at a selected location and/or orientation, according to some embodiments of the invention;

FIGS. 15, 16, 17 and 18 are histopathology images from experimental results in swine, showing thermally damaged nerve tissue, treated from a pulmonary artery location, according to some embodiments of the invention;

FIG. 19 is a histopathology image from a swine experiment for treating the celiac ganglion from an aorta location, according to some embodiments of the invention; and FIGS. 20A-20D illustrate various mechanisms for positioning and/or orienting at least a head of the catheter, comprising the one or more ultrasonic transceivers at a selected position within the vessel, according to some embodiments of the invention.

DESCRIPTION OF SPECIFIC EMBODIMENTS OF THE INVENTION

The present invention, in some embodiments thereof, relates to hypertension treatment and, more particularly, but not exclusively, to treatment of pulmonary hypertension.

A broad aspect of some embodiments relates to positioning an ultrasonic catheter in the pulmonary artery, trachea and/or aorta for targeting and treating nerve tissue by thermally damaging the nerve tissue. In some embodiments, treating comprises emitting ultrasound energy, such as non focused ultrasound, for modifying nerve function. In some embodiments, activity of one or more nerves, nerve segments, nerve plexuses and/or other nerve tissue is reduced or eliminated. In some embodiments, treatment comprises ablating nerve tissue, such as nerve tissue of the pulmonary vasculature, and causing a damage sufficient to prevent regeneration of the tissue.

An aspect of some embodiments relates to selectively treating nerve tissue, using at least one ultrasonic transceiver to characterize tissue and using that same transceiver to emit energy for treating targeted tissue. In some embodiments, selective treatment comprises causing damage to selected nerves without causing substantial damage to non-targeted tissue, such as surrounding organs and/or other nerve tissue. In some embodiments, characterizing tissue comprises identifying one or more organs such as the lungs, trachea, lymph, bronchi or others. In some embodiments, organs are identified based on their echo signal reflection. Optionally, the reflected signals are received by the one or more ultrasonic transceivers of the catheter device, and are analyzed to determine the organ type and/or the relative distance of the organ from the lumen from which treatment is applied, such as the pulmonary artery lumen. In some embodiments, the ultrasonic transceivers are activated at a first energy profile to identify and/or characterize tissue, and at a second energy profile to treat tissue. Optionally, non-targeted tissue is identified. Additionally or alternatively, targeted tissue is identified.

In some embodiments, selective treatment comprises differentiating between nerves during treatment, for example by producing a predetermined temperature profile in the treated nerves. Optionally, the predetermined temperature profile is obtained by emission of ultrasound energy at a selected profile, suitable to heat the nerves to a desired temperature or range of temperatures. In an example, differentiating between nerves comprises causing damage only to nerves that are not coated by myelin by producing a first temperature range, and causing damage to both coated and non-coated nerves by producing a second temperature range.

In some embodiments, selective treatment comprises emitting energy for thermally damaging nerve tissue without causing substantial damage to the artery wall. Optionally, damage to the wall is reduced by keeping the one or more ultrasonic transceivers away from the wall, for example by using a distancing device. In some embodiments, selective treatment comprises treating from an artery in which a wall disorder such as thrombus or atheroma exist, while reducing a risk of breakage of the thrombus or atheroma, which may result in emboli and possibly occlude the artery.

Selective treatment is pursued, in some embodiments, by activating one or more transceivers to emit energy towards a selected direction, and/or deactivating one or more transceivers to reduce or prevent emission in one or more other directions.

An aspect of some embodiments relates to feedback based treatment of the pulmonary vasculature. In some embodiments, treatment is continued and/or modified based on one or more measurements of physiological control parameters, including local parameters such as, for example, pulmonary artery diameter, bronchi diameter, and/or systemic parameters, which may be a byproduct of denervation, including, for example, heart rate, respiratory volume, and/or other physiological parameters. In some embodiments, the physiological parameters are measured internally to the body. Additionally or alternatively, the physiological parameters are measured externally to the body. In some embodiments, the ultrasonic catheter is configured to acquire the one or more physiological parameters. In an example, a physiological parameter such as a diameter of the pulmonary artery is estimated by analyzing echo signals reflected by the artery walls and received by the one or more transceivers of the catheter device. In some embodiments, the physiological parameter is acquired by stimulating the nervous system to evoke an observable physiological response and/or a chain of responses, one or more of which are detectable and optionally measureable.

In some embodiments, a measurement of the physiological parameter acquired before treatment is compared to a measurement of the same physiological parameter following treatment, to determine treatment effectiveness. For example, an increase in artery diameter above a certain threshold, measured following treatment, may indicate that the treatment was effective.

In some embodiments, immediate feedback is provided, and treatment is modified and/or ceased based on the feedback. In an example, immediate feedback comprises assessing dilation of the bronchi, which may be observed shortly after denervation. In another example, immediate feedback comprises assessing arterial blood pressure.

An aspect of some embodiments relates to an ultrasonic catheter structure and/or to elements used with the catheter that are suitable for reducing unwanted movement of the catheter, and more specifically movement of at least a distal portion of the catheter when a more proximal portion of the catheter is passed through cardiac vasculature, where it is subjected to movement resulting from heart pulsation. In some embodiments, the catheter is passed through the right ventricle of the heart. In some cases, contraction of the ventricle may cause movement of the catheter shaft, thereby possibly moving the distal head of the catheter, which comprises the one or more transceivers.

In some embodiments, a structure of the catheter shaft is selected to damp movement resulting from heart pulsation, potentially reducing a number of movements and/or a range of movement of at least a distal head of the catheter. In some embodiments, one or more locations along the catheter shaft are structured to provide a full or partial axial decoupling between axial segments of the catheter, for example so that movement of the head at a distal end of the device is least affected by movement of a more proximal portion of the catheter shaft. Additionally or alternatively, the catheter is anchored to a certain location in the artery and/or to other tissue or organs, to prevent or reduce movement of the catheter relative to the tissue, for example during emission of ultrasound. Optionally, a small range of movement is permitted, such as movement to an extent which does not affect targeting. Additionally or alternatively, a "working frame" is provided, and the catheter is maneuvered within the working frame. Additionally or alternatively, movement of the catheter is synchronized with movement of the targeted tissue, for example by anchoring the catheter to a structure that moves in a similar pattern to the targeted tissue.

In some embodiments, at least a head of the catheter, comprising the one or more ultrasonic transceivers, is positioned and/or oriented within the lumen from which treatment is applied at a predetermined location. Optionally, positioning of the catheter and/or directing of the ultrasonic beam is selected based on one or more of: a distance from the tissue to be treated, a distance from the lumen wall, a position along the length of the lumen, parameters of the ultrasonic beam emitted by the transceivers (e.g beam shape), and/or others. In some embodiments, positioning of the catheter and/or directing of the beam is performed by delivering the catheter over a pre-shaped guide wire, for example a spiral guide wire or a guide wire curved to a substantial Z shape. A potential advantage of the spiral configuration may include setting an advancement path for the catheter in which at any point along the path, at least the catheter head is maintained at a selected distance from the lumen wall, for example in proximity to the lumen wall. Optionally, the catheter is positioned a distance between 0.1 mm to 20 mm from the lumen wall. Optionally, the distance is selected in accordance with the intensity applied, for example a distance ranging between 0.1 mm to 5 mm, 5 mm-10 mm, 15 mm-20 mm or intermediate, larger or smaller distance ranges are used with an intensity between 20 W/cm^2 to 80 W/cm^2. In some embodiments, the spiral diameter (i.e. a diameter of a loop) is selected according to the lumen diameter. Additionally or alternatively, the spiral diameter is selected according to the catheter diameter, for example a diameter of the catheter head. In some embodiments, a similar effect to delivering the catheter over a helical structure may be obtained by delivering the catheter over the Z-shaped wire, and rotating the wire. Optionally, the catheter is introduced over the wire to a position in which the catheter head is proximal to the curved portion of the wire. Alternatively, the catheter is introduced over the wire to a position in which the catheter head is distal to the curved portion of the wire. Another potential advantage of the spiral and/or Z-shaped configurations (and/or any other configurations suitable to position the catheter away from the center of the lumen and in proximity to the walls) may include facilitating treating the lumen circumferentially. Optionally, when applying circumferential treatment by delivering the catheter over a curved guide wire, the curvature of the wire can be selected to obtain a certain orientation of the transceivers at the head of the catheter, for example positioning a transceiver such that a longer dimension of the transceiver (for example being a rectangular transceiver) extends at an angle relative to a longitudinal axis of the lumen.

An aspect of some embodiments relates to applying treatment by positioning an ultrasonic catheter comprising a temperature-controlled balloon arrangement in an air filled lumen, such as the trachea. In some embodiments hot and/or cold fluid is circulated within the balloons. In some embodiments, circulation of fluid at selected temperatures or ranges thereof is controlled to shape the treated tissue area, such as to obtain a predetermined depth of the effective field in the tissue. In an example, cold fluid is circulated within an inner balloon which surrounds the catheter, for cooling the one or more transceivers, and warm fluid is circulated within an external balloon, for enhancing the thermal heating effect of the emitted energy and potentially increasing a depth of the effective ultrasound field in the tissue. In an embodiment, cool fluid flows over the transceivers to cool them, thereby absorbing the excess heat and warming up. Optionally, the same warmed-up fluid or a partial volume thereof is then circulated to the outer balloon, to enhance the thermal heating effect.

In some embodiments, the balloons do not surround a full circumference of the catheter head. Optionally, the balloons are arranged relative to the catheter head and/or relative to each other such that an emitting surface of the one or more transceivers is exposed to face the tissue. Alternatively, the balloons are positioned to cover at least a portion of the transceiver's surface.

In some embodiments, a balloon arrangement comprises a plurality of balloons which are effective to push the catheter away from the wall of the trachea.

In some embodiments, the fluid in the one or more balloons acts as a transferring medium for carrying the ultrasound energy from the transceivers to the trachea wall.

In some embodiments, the catheter, even when the one or more balloons are inflated, does not block the airway. Optionally, a total cross sectional diameter of the catheter with the inflated balloons is at least 5%, at least 10%, at least 20% or intermediate, larger or smaller percentages smaller than a cross sectional diameter of the trachea.

In some embodiments, one or more organs and/or tissues are identified for selectively applying the treatment from the air filled lumen, such as the trachea. In an example, cartilage rings of the trachea are identified, and energy is emitted in between the rings. Optionally, the cartilage rings are identified by processing of echo signals reflected from the rings and received by the transceivers of the catheter.

An aspect of some embodiments relates to treating nerve tissue of the celiac ganglia from an aortic position. In some embodiments, the celiac artery ostium is identified, and energy is emitted to thermally damage the celiac ganglion. Optionally, the ostium is engaged by a mechanical element, such as a rod, extending from the catheter.

It is noted that various conditions may be treated using the methods and/or devices described herein, including, for example, one or more of pulmonary hypertension, pulmonary arterial hypertension (PAH), asthma, chronic obstructive pulmonary disease (COPD), mesothelioma, heart failure, atrial fibrillation, sleep apnea, insulin resistance and/or other conditions directly or indirectly associated with nerve activity.

Throughout the application, when the term "pulmonary artery" is used, the term may refer to one or more of the pulmonary artery trunk, the right pulmonary artery, the left pulmonary artery, and/or the bifurcation area of the pulmonary artery. In some embodiments, a catheter structure and/or a treatment protocol are selected based on an anatomy of the pulmonary artery region intended for treatment. For example, when treating the pulmonary artery trunk, in which the cross sectional area is relatively large (comprising a diameter which is about 1.5 times a diameter of the right or left pulmonary arteries), it may be desirable to position the catheter head closer to the lumen wall as compared to, for example, when treating in an artery region of smaller cross sectional area. Optionally, when treating an artery region having a relatively large cross sectional area, higher intensities are applied. In some embodiments, a high intensity is applied to compensate for undesired movement of the catheter within the large artery region. Optionally, by directing energy at a high intensity towards a large volume or cross section of tissue, the energy spreads over the large volume, thereby reducing the actual intensity of energy that effectively reaches the various tissue locations within the large volume.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

A General Method for Treating Nerves Using an Intravascular Catheter in the Pulmonary Artery Referring now to the drawings, FIG. 1 is a flowchart of a method for treating nerves, according to some embodiments of the invention.

In some embodiments, a patient is diagnosed with a respiratory condition such as one or more of pulmonary hypertension (including, for example, pulmonary arterial hypertension), asthma, and/or chronic obstructive pulmonary disease (COPD) (101). In some cases, a decision is made, such as by a physician, to treat the condition (103).

In some embodiments, an intravascular ultrasonic catheter device is introduced to the pulmonary artery (105), to treat one or more sympathetic nerves which innervate the pulmonary vasculature. In some embodiments, the catheter device is configured to emit ultrasound energy having parameters suitable for treating the nerves, for example as further described herein. In some embodiments, treating comprises modifying nerve activity, for example reducing the activity of one or more nerves. In some cases, treating comprises thermally damaging the nerves, to reduce or eliminate their function. In some embodiments, treatment comprises ablating nerves and causing enough damage to prevent the nerves from regenerating.

In some embodiments, treatment includes applying the ultrasonic treatment, in addition to administrating pharmaceutical treatment (e.g. medication such as diuretics, beta blockers, ACE inhibitors or other). Alternatively, the ultrasonic treatment alone is provided.

In some cases, the device is introduced to the body in a percutaneous procedure. In some embodiments, the device is passed through the right atrium, into the right ventricle, and advanced into the main pulmonary artery. In some cases, the device is further advanced into the left pulmonary artery and/or the right pulmonary artery (107). In some cases, the device is positioned in the vicinity of the bifurcation.

In some embodiments, positioning of the device within the vessel involves anchoring the device. In some embodiments, positioning of the device involves stabilizing the device, for example reducing movement of the device resulting from the flow of blood within the artery, and/or reducing movement of the device resulting from muscular contraction such as heart contraction, for example in cases in which the catheter is passed through the heart. Optionally, if treatment is performed in the vicinity of the bifurcation, the device is anchored against turbulent flow at the bifurcation. In an example, the head of the catheter is held in place in the bifurcation area by an anchoring element, such as a curved rod or a spring coil which is coupled to a more proximal portion of the catheter, and extends into the left and/or right pulmonary arteries to anchor the more proximal of the catheter to the smaller artery region, thereby reducing or preventing movement of the more distal portion of the catheter comprising the head.

In some embodiments, positioning of the device involves distancing one or more emitting elements of the catheter away from the wall of the artery lumen. In some embodiments, positioning of the device is selected in accordance with heart pulsation, for example by locating the catheter in an area in which it is least subjected to movement.

In some embodiments, since the pulmonary artery (for example at the main pulmonary artery section) comprises a relatively larger artery diameter, for example ranging between 15 mm to 40 mm, for example 20 mm, 30 mm, 37 mm, or intermediate, larger or smaller diameters. In some embodiments, a catheter comprising a diameter of between 4 F to 11 F is used. A potential advantage of treating from within the relatively large pulmonary artery using a catheter with a large head diameter may include increased circumferential coverage of the artery walls, for example as compared to a catheter having a smaller head diameter.

In some embodiments, various positioning elements such as a distancing device and/or one or more balloons may be used with the catheter to assist in locating the catheter at a desired location for applying treatment.

In some embodiments, the catheter itself and/or a guide wire used with the catheter (e.g. a guide wire over which the catheter is delivered) is configured to obtain and/or maintain a selected position in the vessel. In some embodiments, the selected position is one in which the one or more transceivers at a distal head of the catheter are positioned adjacent the vessel wall. Additionally or alternatively, the selected position is one in which a maximal coverage of the vessel circumference is obtained, for example by positioning the one or more transducers substantially aligned with the vessel axis. In an example, a shaft of the catheter is mechanically deflectable only in certain directions and/or angles. In another example, a guidewire used with the catheter comprises a predefined curvature, which places the catheter that is delivered over it at a selected location, for example relative to the vessel walls. Optionally, the guide wire comprises memory shape material, such as nitinol.

In some embodiments, treatment is applied to modify the activity of one or more nerves, nerves sections, and/or nerve plexuses (109). In some embodiments, applying treatment comprises emitting ultrasound energy. In some embodiments, non-focused ultrasound is applied. Optionally, treatment is applied in pulses.

In some embodiments, treatment parameters are selected to produce an ultrasonic field which is effective to modify nerves within a certain distance range from the lumen wall, for example a distance of up to 5 mm, up to 8.5 mm, up to 10 mm or intermediate, larger or smaller distances from the artery wall. Optionally, parameters are selected such as not cause damage to the vessel wall tissue.

In some embodiments, emitting is performed from a minimal radial distance away from the artery wall, such as at least 1 mm from the wall, allowing a sufficient amount of blood to flow between the transceiver and the wall, potentially cooling the transceiver and/or reducing a risk of thermal damage to the vessel wall.

Exemplary treatment parameters usable when treating nerves from a pulmonary artery location may include one or more of an intensity of at least 35 W/cm^2, at least 40 W/cm^2, at least 45 W/cm^2, at least 55 W/cm^2, at least 65 W/cm^2 or intermediate, higher or lower intensities, a frequency ranging between 10 MHz to 20 MHz, such as 12 MHz, 15 MHz, 18 MHz or intermediate, higher or lower frequencies, and/or a waveform which is sinusoidal. It is noted that other parameters may be used, including various intensity and/or frequency ranges, and/or various waveforms such as squared or triangular. In some embodiments, an effect of the treatment is assessed (111). In some embodiments, immediate feedback is provided, such as by observing physical changes to the bronchi, for example as further described herein. In some embodiments, treatment is applied and/or modified based on feedback. In some embodiments, obtaining feedback comprises assessing a condition of the artery, such as by processing of echo signals received by the device. In an example, a diameter of the artery, for example at one or more treatment locations, is estimated. Optionally, vasodilation or constriction of the artery are assessed using the diameter estimation.

In some embodiments, the device is moved to a different location (113) along the pulmonary artery, for example in attempt to target other nerve tissue. In some embodiments, one or more of steps 109-113 are repeated. In some embodiments, treatment is applied at a plurality of locations, for example a first location in the main pulmonary artery, before the bifurcation, a second location in the vicinity of the bifurcation, and a third location within the right and/or left branches of the artery. Typically, the device is positioned within the pulmonary vasculature, and does not enter the lungs.

Examples of Targeted Nerve Tissue

Figure 2:
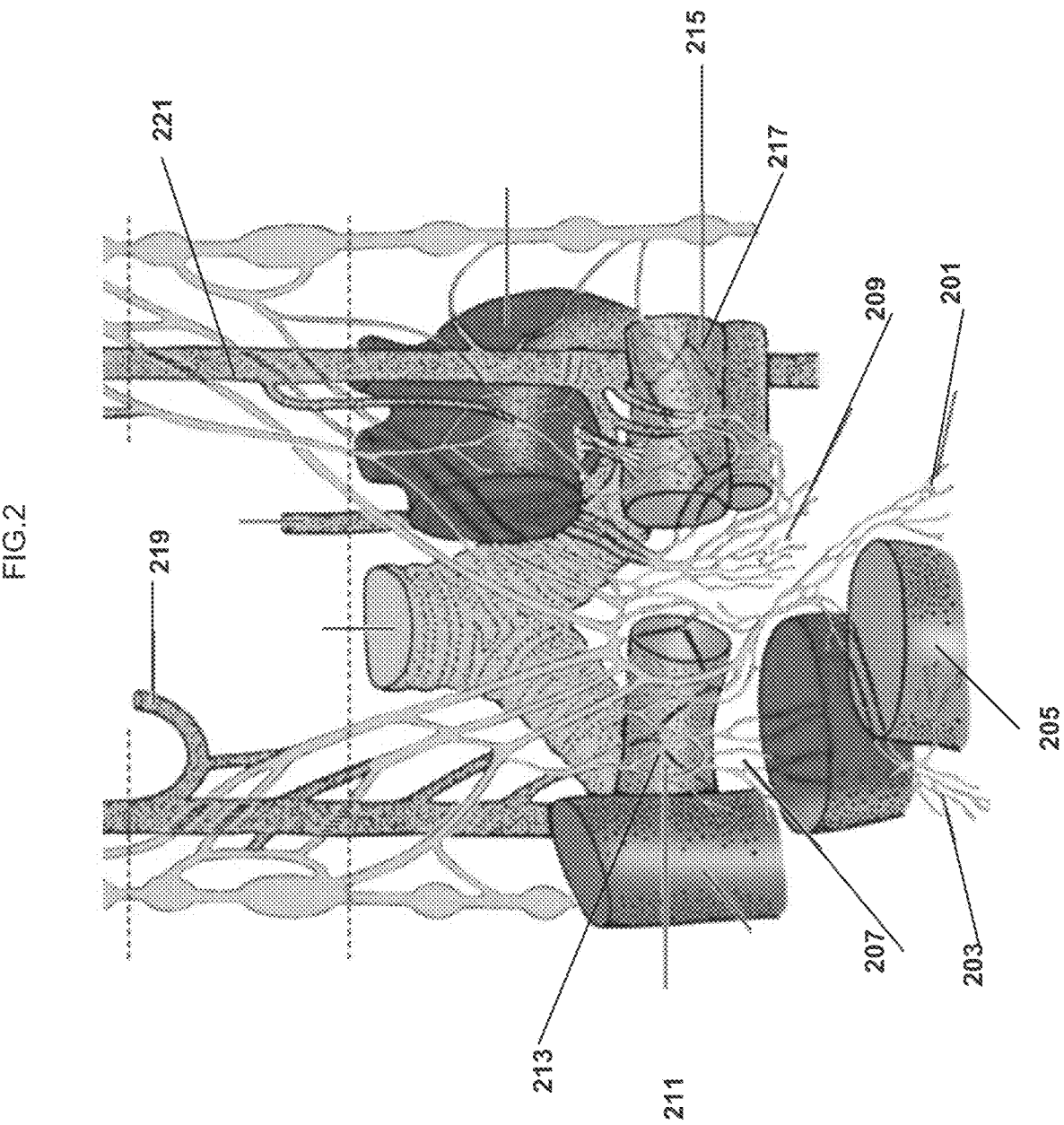

FIG. 2 is a schematic illustration of neural networks and organs in the vicinity of a pulmonary artery, in a human thorax. Some of the organs are shown only in part, to enable viewing adjacent organs. The illustration shows the layout of nerves and nerve plexuses, which may be treated by an apparatus for example as described herein. In some embodiments, the targeted nerves may include one or more of, for example, the left coronary plexus 201 and/or the right coronary plexus 203, surrounding the main pulmonary artery 205; the right atrial plexus 207 and/or the left atrial plexus 209; the right pulmonary plexus 211, surrounding the right pulmonary artery 213; and the left pulmonary plexus 215, surrounding the left pulmonary artery 217.

In some embodiments, damage to nerves such as the laryngeal nerve 219 and/or the vagus nerves such as the left vagus nerve 221 is reduced or prevented. Alternatively, in some cases, pulmonary branches of the vagus nerve are treated, for example to modify bronchi activity.

Position and Operation of an Ultrasonic Catheter
Inside the Pulmonary Artery

Figure 3A:
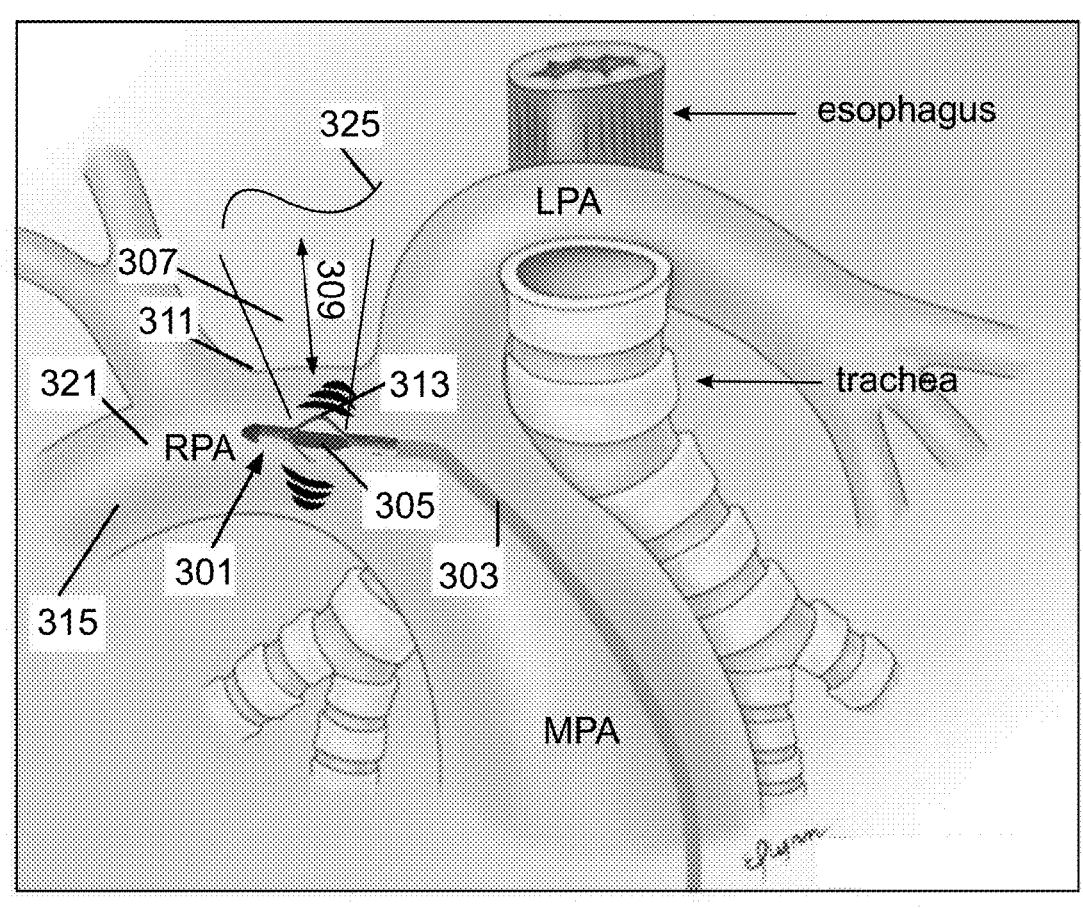
Figure 3B:
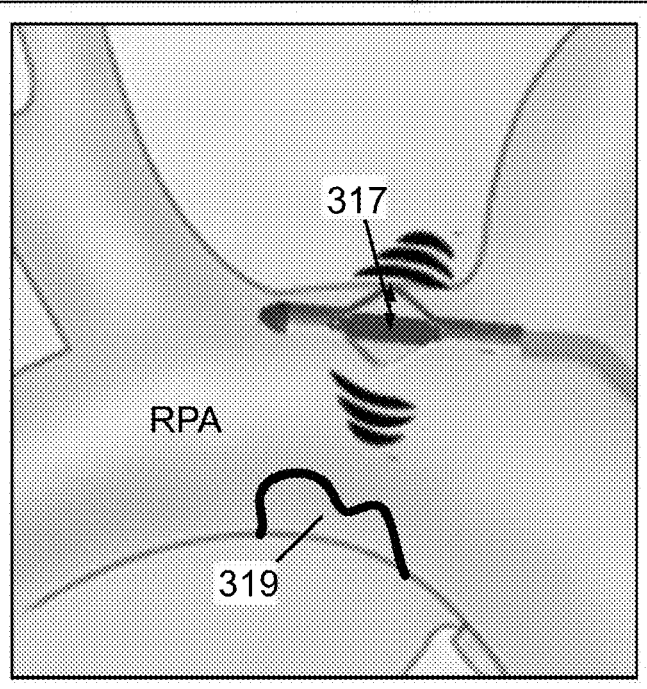

FIGS. 3A-3B illustrate an ultrasonic device positioned within a pulmonary artery, according to some embodiments of the invention. In some embodiments, device 301 is delivered to the pulmonary artery, for example to the right pulmonary artery 321, as shown in this example.

In some embodiments, device 301 is introduced to the artery with the aid of a guiding sheath or catheter 303. In some embodiments, a size of the catheter ranges between 4-12 Fr, such as a 4 Fr, 6 Fr, 8 Fr.

In some embodiments, device 301 comprises one or more ultrasonic transceivers 305, adapted for emitting and/or receiving ultrasound energy. In some embodiments, an ultrasonic field 307 produced by the one more transceivers is effective to modulate nerve activity to a depth 309 of, for example, up to 10 mm, up to 8 mm, up to 6 mm, up to 12 mm, or intermediate, larger or smaller ranges from the artery wall 311.

In some cases, for example in patients diagnosed with pulmonary arterial hypertension, a thickness of wall 311, for example a thickness of a medial layer of the wall, increases. In some cases, the thickness may increase in 1-3 mm. In a situation in which the artery wall is characterized by increased thickness, relative to a normal wall, emission of unfocused ultrasound which is effective to travel a relatively large distance may be advantageous.

In some embodiments, device 301 comprises one or more transceivers facing a single direction. Alternatively, device 301 comprises a plurality of transceivers, such as 2, 3, 4, 6, 8, or intermediate, larger or smaller number, facing various directions. Optionally, the transceivers are arranged circumferentially. In some embodiments, for example when the device is unidirectional, the device is rotated axially within artery lumen 315, such as to treat circumferential segments of the artery.

In some cases, the device is centered with respect to artery lumen 315, for example as shown in FIG. 3A. Alternatively, the device is positioned closer to one of the artery's walls, for example as shown in FIG. 3B.

In some embodiments, device 301 is equipped with a distancing device 313, for example as further described herein. In some embodiments, the distancing device pushes the device away from artery wall 311. Optionally, the distancing device pushes transceiver 305 away from wall 311, for example away from an innermost layer of the wall such as the intima, to a distance 317 (as shown in FIG. 3B) ranging between 1 mm to 10 mm, such as 3 mm, 5 mm, 7 mm or intermediate, longer or shorter distances.

A potential advantage of keeping at least transceiver 305 away from the wall may include reducing a risk of damage to the wall, for example a risk of thermal damage caused by overheating of the tissue. In some embodiments, enough blood is allowed to flow between the transceiver and the artery wall, to cool the wall. Another potential advantage may include reducing a risk of damage to the transceiver, for example damage caused by material such as organic material charring over the transceiver surface.

In some cases, thrombi, atherosclerotic atheroma and/or other wall related disorders 319 exist in the artery. In such a case, a distance between device 301 which is located within lumen 315 and the surrounding nerves 325 which are intended to be treated is effectively increased. By producing an ultrasonic field with a relatively large effective range, an interfering effect of the wall disorder with the transfer of energy may be overcome.

In some cases, as ultrasound energy is expected to be absorbed in the artery tissue more than it is absorbed in the thrombus or atheroma, the energy may pass through the thrombus or atheroma with a minor or no substantial decrease in intensity. A potential advantage of using ultrasound to treat the nerves, for example in comparison to radiofrequency (RF) or laser, may include the transferring of an increased amount of energy through the wall disorder, for ablating nerves located beyond the artery wall. RF or laser energy are expected to be absorbed in the tissue of the wall disorder more than ultrasound energy is absorbed, therefore when using ultrasound energy, a larger amount of energy is expected to reach the nerves intended for treatment.

In some cases, in which a narrowing of the artery is observed, for example due to plaque, the catheter device is used for preventing partial or total occlusion of the artery, for example by targeting nerves associated with constriction of the artery, to prevent spasm and/or cause permanent dilation of the artery which will reduce the risk of the artery being occluded, for example by the plaque.

In some embodiments, the distancing device pushes the catheter away from the wall disorder, reducing a risk damage which may be caused, for example, by breakage of a thrombus or atheroma, which could result in an embolus. A risk of breakage may be reduced by the relatively low energy absorption of the thrombus or atheroma.

In some embodiments, guiding catheter 303 is passed through the right ventricle of the heart. Contraction of the ventricle may cause periodical movement of the catheter, possibly resulting in movement of transceiver 305. In some cases, when applying treatment, it is desirable to stabilize device 301 in position, for example stabilize the device with respect to a longitudinal, axial direction of the artery and/or with respect to a horizontal, cross sectional direction of the artery.

In some embodiments, for example as further described herein, device 301 is anchored with respect to the artery walls and/or with respect to the targeted nerves 325, for example by a positioning element, as further described herein. Optionally, the device is anchored in a constant, fixed position. Alternatively, the anchoring allows for a certain range of axial and/or cross sectional movement of the device, for example axial movement within a distance range smaller than twice a maximal axial spread of the effective field. In some embodiments, the device is anchored in a configuration which provides for the device and the target, such as nerves 325, to move together in a synchronized manner, for example move periodically with heart pulsation. Optionally, the device is equipped with an expandable member, which engages the artery walls when expanded, anchoring at least a portion of the device (such as a distal portion on which the transceivers are mounted) in place (e.g. in a selected cross sectional and/or axial position relative to the artery), allowing the device and artery to move together in a synchronized manner.

Additionally or alternatively to anchoring, for example as further described herein, the device is provided with an axial decoupling, for example in which a segment of a shaft of the device dampens or does not transfer axial forces, to reduce movement of the one or more transceivers 305 resulting from movement of a more proximal portion of guiding catheter 303. Optionally, the axial decoupling is structured to allow sufficient transmission of torque in a distal direction, to enable maneuvering the catheter.

In some embodiments, a "working frame" is constructed, in which the device is oriented and/or positioned relative to the target, such as nerve 325. Optionally, a guiding pattern is used, for example comprising one or more markings which indicate a current and/or desired position of the device. In an example, the markings comprise a dot, arrow or other localized marker which is fitted within a larger marker defining the working frame, for example a marker in the form of a circle. In some embodiments, imaging modalities are used. Optionally, angiography images are marked to indicate a location and/or direction for energy emission. Optionally, the markings are placed to indicate non-targeted tissue, to prevent or reduce emission towards tissue or anatomical structures such as the lungs, the vagus, the trachea, the aorta.

Additionally or alternatively, the device is not anchored but rather positioned at a location in which movement of the device is synchronized with movement of the targeted tissue. In an example, considering that for some targeted tissues movement of the heart moves the targeted tissue, the device is positioned in proximity to the heart.

An Ultrasonic Catheter Structure

Figures 4A, 4B:
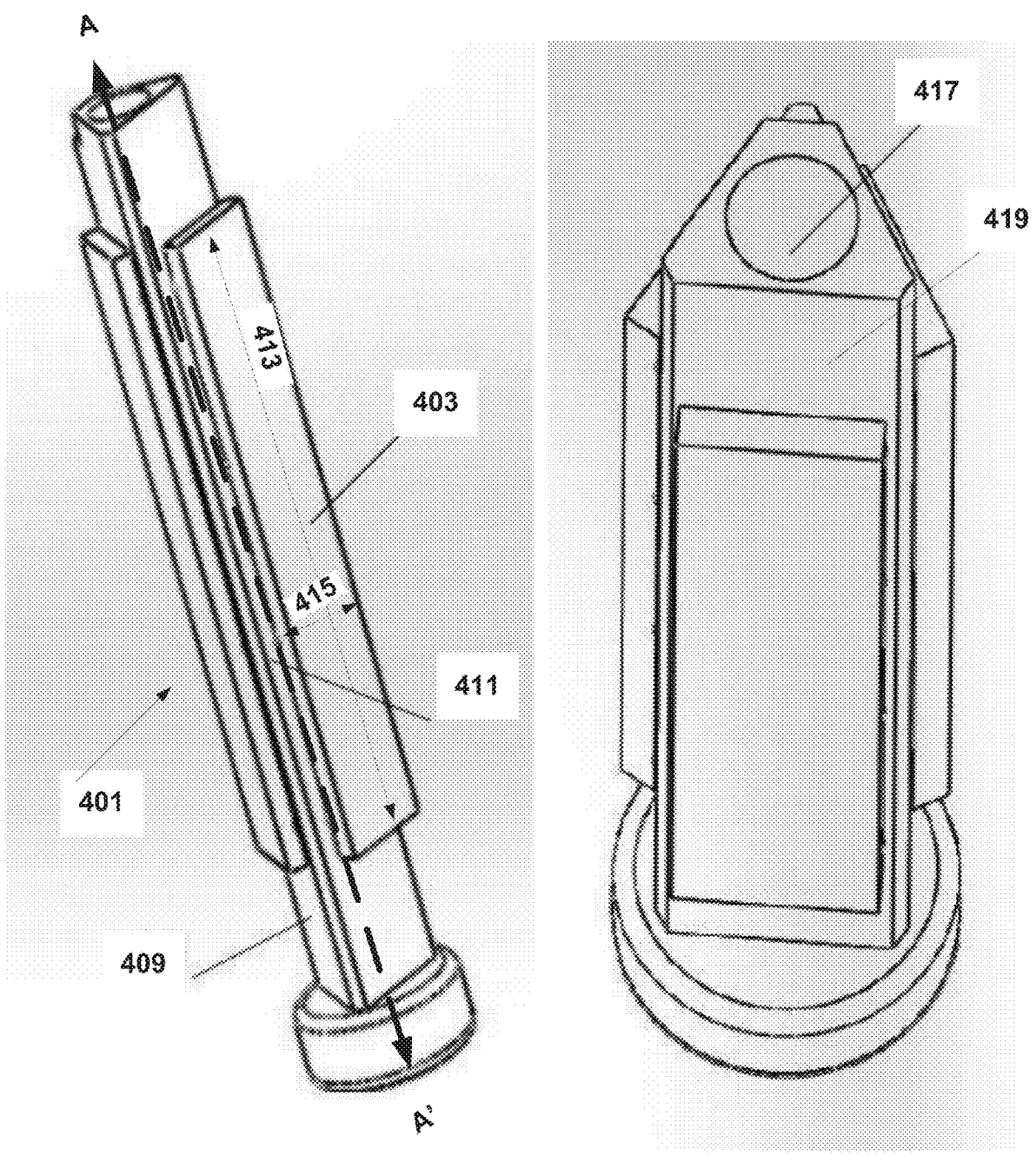

FIGS. 4A-4B are isometric drawings of an exemplary catheter head comprising a plurality of ultrasonic transceivers, according to some embodiments of the invention.

In some embodiments, head 401 comprises one or more piezoelectric transceivers such as transceiver 403, configured for emitting and/or receiving ultrasound by comprising a body vibratable at ultrasonic frequencies. In some embodiments, the transceivers are coupled to a chassis 409 of head 401. Optionally, the transceivers are mounted onto one or more external surfaces of chassis 409.

In some embodiments, catheter head 401 is sized to fit within the pulmonary artery, the head having a diameter ranging between, for example, 1.3 mm to 4 mm (corresponding with a catheter of between 4-12 F). Optionally, head 401 is sized such that it occupies less than 50%, less than 40%, less than 30% or other percentage of the cross section of the artery, to reduce interference with and/or obstruction of blood flow.

In some embodiments, the plurality of transceivers include three transceivers, for example arranged in a triangular configuration. Alternatively, the head comprises a different number of transceivers, such as 2, 4, 5, 6, 8 or intermediate, larger or smaller number. The transceivers may be arranged in various configurations, such as a squared configuration, a hexagonal configuration, an octagonal configuration, or other polygonal configurations. Optionally, the spatial arrangement of the transceivers is configured such that a periphery of head 401 is reduced to a minimum.

In some embodiments, adjacent transceivers are positioned such that a spacing 411 is formed between them. Optionally, spacing 411 provides an electrical and/or thermal isolation between the adjacent transceivers.

In some embodiments, one or more of the transceivers is adapted for emitting ultrasound. In some embodiments, one or more of the transceivers is adapted for receiving ultrasound. In some embodiments, a single transceiver is adapted for both emitting and receiving ultrasound. Optionally, a portion of the transceiver is adapted for emitting ultrasound, and another portion is adapted for receiving ultrasound.

In some embodiments, the one or more transceivers are adapted for receiving echo signals, such as echo signals reflected by walls of the pulmonary artery.

In some embodiments, the transceivers are arranged circumferentially. Optionally, the irritated energy is suitable for treating a circumferential region of tissue.

In some embodiments, each of the transceivers faces a different direction than the other transceivers. Optionally, each of the transceivers is configured for emitting and/receiving ultrasound from a different portion of the artery wall. Additionally or alternatively, two or more of the transceivers face the same portion of the artery wall. Optionally, the transceivers are arranged so that each of the transceivers covers a sector of the cross section of the artery, such as a semicircle, a quadrant, a sextant, or a sector having other central angle such as 20 degrees, 40 degrees, 70 degrees.

In some embodiments, for example as shown in this figure, a transceiver is shaped as a rectangle. Exemplary dimensions of a rectangular transceiver include a length 413 ranging between, for example, 3 mm to 8 mm, and a width 415 ranging between 0.8 mm to 2 mm. Optionally, all transceivers are uniformly shaped, for example all transceivers are shaped as rectangles. A potential advantage of uniformly shaped transceivers may include producing a symmetric effective field. Optionally, by having a symmetric field, additional safety is provided, for example in cases where an uncontrolled axial rotation of the catheter head occurs within the artery. Another potential advantage may include simplifying the manufacturing process. Alternatively, in some embodiments, each of the transceivers comprises a different shape, for example one transceiver shaped as a rectangle, a second transceiver shaped as a trapezoid, etc. Additionally or alternatively, in some embodiments, all transceivers are uniformly shaped with a shape other than a rectangle, such as a trapezoid, a circle, a triangle, or any other shape.

In some embodiments, the transceivers are selected during the assembling of the catheter. Optionally, the transceivers are sorted according to characteristics such as a resonant frequency and/or impedance properties. Optionally, a catheter assembled with pre-sorted transceivers can be operated at a frequency range that is determined according to the resonant frequencies of its transceivers, thereby optionally increasing the efficiency of the catheter.

In some embodiments, the transceivers of a single catheter comprise different resonant frequencies. Optionally, the transceivers are operated independently of one another. Alternatively, two or more of the transceivers are operated together.

In some embodiments, the catheter can be used as a unidirectional catheter, a bidirectional catheter, a triple directional catheter or any multidirectional catheter. Optionally, this is obtained by selectively operating one or more transceivers at an efficiency higher than one or more other transceivers.

In some embodiments, the operating frequency is selected and/or modified so that two opposing transceivers of a catheter (for example transceivers that are furthest apart from each other on a squared shaped catheter) are operated together. The operating frequency may then be modified to sweep between the transceivers and operate a second set of transceivers. A potential advantage of alternating between the transceivers may include reducing overheating of the transceivers, which may occur when a transceiver is activated over time. Optionally, one or more transceivers that are directed towards the target tissue are activated, while one or more transceivers that are directed towards non-target tissue are deactivated.

In some embodiments, the transceivers are operated (e.g. by a controller, for example comprised within a console of the catheter) according to a lookup table. Optionally, the lookup table correlates between an efficiency of each of the transceivers and a certain operating frequency. By operating the transceivers according to the lookup table, various combinations and alternations between the transceivers can be obtained.

In some embodiments, a radially outward facing surface of the one or more transceivers is flat. Additionally or alternatively, one or more transceiver surfaces are concave. Additionally or alternatively, one or more surfaces are convex.

In some embodiments, chassis 409 is formed as an elongated shaft, in this example having a triangular cross section profile. Alternatively, in other embodiments, the chassis may comprise a square profile, a rectangular profile, a circular profile, a hexagonal profile, or an arbitrary profile. Optionally, a cross sectional profile of the chassis corresponds with the transceiver configuration, for example, a triangular configuration of transceivers is mounted (directly or indirectly) onto a triangular chassis.

In some embodiments, chassis 409 is cannulated. Optionally, a lumen 417 (as clearly shown, for example, in FIG. 4B) within the chassis is dimensioned to receive a guide wire. In some embodiments, lumen 417 is sized to receive a pressure measurement device, for example a guide wire comprising one or more pressure sensors. In some embodiments, lumen 417 is sized and/or shaped to receive a guide wire of a predefined curvature, for example a Z-shaped guide wire.

Optionally, when head 401 is positioned within the artery, blood flow is allowed to pass through the lumen. In some embodiments, substances such as saline, cooling fluid, contrast liquid, medication and/or other fluids are delivered through the lumen of chassis 409. In some embodiments, a collapsed balloon is delivered through the lumen of chassis 409, and delivered through the distal tip of the catheter to be inflated within the artery. Optionally, an inflating substance such as air or saline are passed through the lumen to fill the balloon. In some embodiments, the balloon comprises one or more pressure sensors. Optionally, the one or more sensor are configured on an external wall of the balloon, for example at a distally facing wall, and are used for assessing pressure within the artery.

In some embodiments, a radially outward facing surface of chassis 409 such as facet 419 serves as a platform onto which a PCB and/or one or more transceivers can be mounted.

In some embodiments, chassis 409 is formed of an electrically conductive material. Additionally or alternatively, chassis 409 is formed of a thermally conductive material, for transferring heat away from the transceivers. Optionally, chassis 409 is coated by a thermally and/or electrically conductive material. Exemplary materials include metal such as gold or copper. Optionally, various components of the catheter such as electrical wiring are soldered onto a surface of the chassis, and may thereby reduce the need for soldering pads. Optionally, chassis 409 is rigid enough to prevent deformation of the piezoelectric transceivers that are mounted onto it.

In some embodiments, the facets of chassis 409 are evenly distributed with respect to a longitudinal axis AA' of the chassis. For example, each facet of a triangular chassis is positioned at an equal radial distance from longitudinal axis AA'. Optionally, by mounting the transceivers onto facets such as facet 419 of the chassis, the transceivers are aligned with respect to longitudinal axis AA' and/or with respect to each other. Optionally, a radial distance between each transceiver and axis AA' is equal for all peripherally arranged transceivers. Alternatively, the distance varies for different transceivers. A potential advantage of utilizing a periphery of the catheter head for mounting of components such as the transceivers may include a simpler, more reliable manufacturing and assembly process.

In some embodiments, one or more of the transceivers is electrically coupled to a circuit board (not shown in this figure). Optionally, a surface of the PCB opposite the transceiver is mounted onto a chassis 409. Additionally or alternatively, one or more of the transceivers is mounted directly onto chassis 409.

In some embodiments, catheter head 401 is in communication, such as by a wire connection or wireless connection, with an operating console. In some embodiments, the console comprises software for processing the acquired echo signals.

In some embodiments, the console is configured for scanning an impedance of the transceivers and comparing the scanning results to calibrated values, to determine if the catheter is qualified for use.

An Intravascular Distancing Device of a Catheter

Figures 5A, 5B:
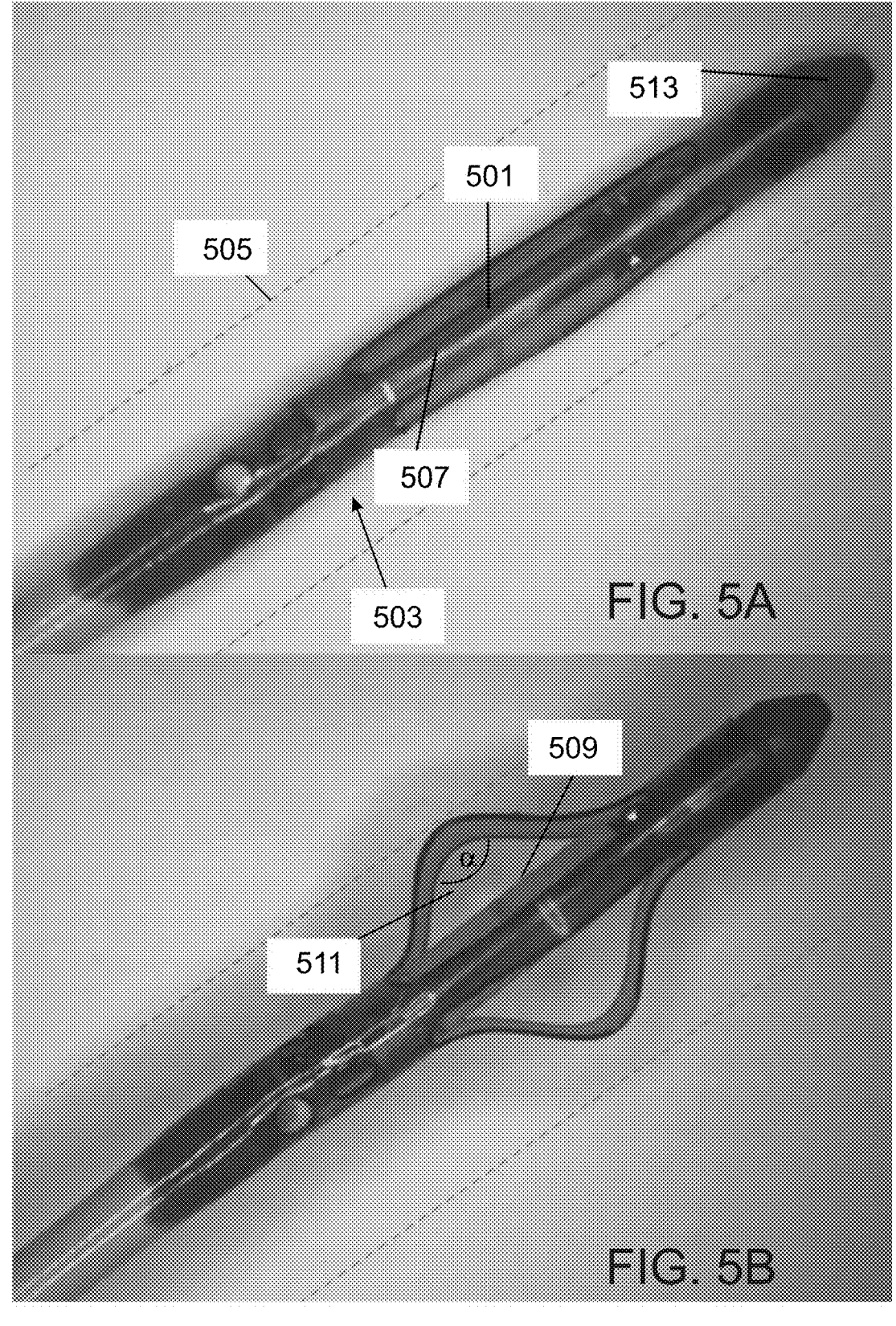

FIGS. 5A-5B are photos a distancing device 501 of a catheter in a closed configuration (FIG. 5A) and an expanded configuration (FIG. 5B), according to some embodiments of the invention. In some embodiments, distancing device 501 is configured for pushing catheter head 503 away from the artery wall 505. In some embodiments, one or more of the transceivers 509 is pushed away from the wall. In some embodiments, distancing device 501 is configured for centering head 503 with respect to the artery wall.

In some embodiments, when device 501 is in the closed configuration, a total diameter of the catheter head 503 including the distancing device threaded onto the head is small enough to provide for insertion and/or removal and/or positioning of the catheter within the artery. For example, the total diameter ranges between 1.3 mm to 2.6 mm or intermediate, longer or shorter diameters. In some embodiments, a total diameter of head 503 is small enough to enable delivery through a guiding catheter or sheath.

In some embodiments, distancing device 501 is formed in the shape of a slotted cylinder. Optionally, cylinder portions 507 in between the slots form bendable leaflets. In some embodiments, in an expanded configuration, as shown for example in FIG. 5B, the leaflets are forced into a rounded 'elbow' shaped configuration, pushing the one or more transceivers 509 away from wall 505. Optionally, the transceiver is pushed at least 1 mm, at least 0.5 mm, at least 2 mm or intermediate, large or smaller distances away from the vessel wall.

In some embodiments, leaflets 507 are positioned such that in the open position, they do not interfere with the field of emitted ultrasound, and in the closed position, the leaflets conform into recesses between the transceivers for maintaining a minimal diameter of the catheter.

In some embodiments, in the closed configuration, leaflets 507 cover at least a portion of the transceiver surface and protect it. In some embodiments, a width of a leaflet is small enough to reduce an unwanted thermal effect on the vessel wall. Additionally or alternatively, a width of a leaflet 507 is selected such as to prevent mechanically induced damage such as scratches to the artery wall tissue.

In some embodiments, even when distancing device 501 is expanded, blood is allowed to flow between the artery wall and the one or more transceivers 509. For example, blood may flow through an aperture 511 formed by bending leaflet 507 to the elbow configuration. Optionally, the flow of blood cools down the artery wall.

In some embodiments, distancing device 501 is expanded in multiple steps, for example 2, 3, 4, 5 steps. In an exemplary embodiment, distancing device 501 is first bended such that an angle a ranging between 110-175 is formed by leaflet 507, and in the second step angle a is reduced to, for example, 90-110 degrees, as transceiver 509 is being pushed further away from wall 505.

In some embodiments, distancing device 501 is transferred into an open configuration by retracting distal tip 513 of catheter head 503 in the proximal direction. Optionally, retraction is performed by pulling an internal shaft of the catheter which is connected to tip 513, such as a guide wire shaft, in the proximal direction. Optionally, retraction is performed by pulling on an inner cable coupled to tip 513. In some embodiments, the guide wire shaft and/or the cable are coupled on one end to distal tip 513, and on an opposite end to a handle configured externally to the body. Optionally, the handle comprises a lever for operating the distancing device, for example by remotely pulling on tip 513 to move it in the proximal direction. In some embodiments, a diameter of the proximal end of tip portion 513 is equal to a diameter of the cylinder of distancing device 501, and by retraction of tip 513 force is applied by the tip on the cylinder of distancing device 501, causing leaflets 1307 to bend.

In some embodiments, distancing device 501 comprises a combination of rigid and soft materials, for example layered on top of each other. Optionally, by using a rigid material, the distance between catheter head 503 and wall 505 is maintained. Optionally, by using a soft material, damage to the tissue of wall 505 is reduced or prevented. In some embodiments, distancing device 501 comprises a soft plastic material embedded with fibers such as Nitinol fibers.

Selective Treatment

Figure 6A:
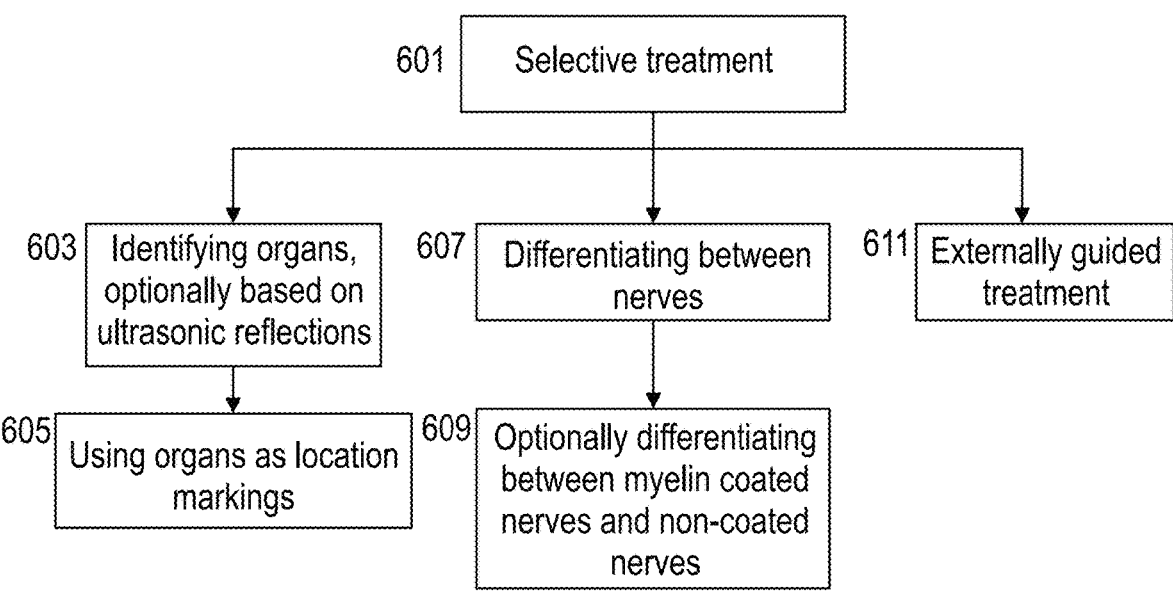

FIG. 6A is a flowchart describing a variety of options for selectively treating nerve tissue, according to some embodiments of the invention. It is noted that any of the described options may be used independently and/or together with one or more of the other options described.

In some embodiments, selective treatment (601) comprises targeting nerves while damage to non targeted tissue, such as surrounding organs and/or non targeted nerves, is reduced or prevented. In some embodiments, selective treatment comprises targeting a predetermined nerve, nerve segment, and/or nerve plexus. In some embodiments, selective treatment comprises identifying nerves according to their innervating function, and targeting those nerves. In some embodiments, selective treatment comprises modifying energy emission parameters such as intensity, frequency, duration, timing and/or other operational parameters according to the selected target, for example according a size of the target and/or a distance of the targeted nerve(s) from the artery lumen. Optionally, the temperature profile is selected according to desired level of thermal damage and/or according to a location of the targeted nerves with respect to the catheter and/or according to the type of nerve tissue intended for treatment.

In some embodiments, one or more organs are identified before and/or during the procedure (603). Optionally, a location of the organs relative to the artery lumen is identified based on an ultrasonic reflection of an organ. Additionally or alternatively, organs are identified using imaging modalities.

In some embodiments, echo signals reflected by one or more surrounding organs are received by the one or more transceivers of the catheter device. Optionally, the signals are processed, for example by a console in communication with the device, to identify one or more organs which reflected the signals, such as, for example, one or more of the heart, lungs, aorta, and/or trachea. In an example, a distinctive echo signal pattern may be acquired from the trachea, since it is mostly filled with air. A potential advantage of identifying organs may include increasing a safety level of the device, by distinguishing between the organs even though they may be located very close to each other, and orienting the catheter device to emit energy in certain directions, selected with respect to the identified organs so that damage to those organs is reduced. In some embodiments, the identified organs are used as location markers (605). Optionally, a position of the catheter along the artery and/or an angular orientation of the catheter are selected using the location markers. In some embodiments, an operating console of the device is configured to provide, for example to a physician, an indication to activate and/or deactivate emission of ultrasound energy, in accordance with the detected location of one or more identified organs. A potential advantage of treating nerves using location markers, such as identified organs acting as location markers, may include reducing a risk of damage to non-targeted tissue. In an example, air ways such as the trachea are identified based on a relatively strong ultrasonic reflection. In another example, the esophagus is identified based on an echo pattern indicating peristaltic movement.

Figure 6B:
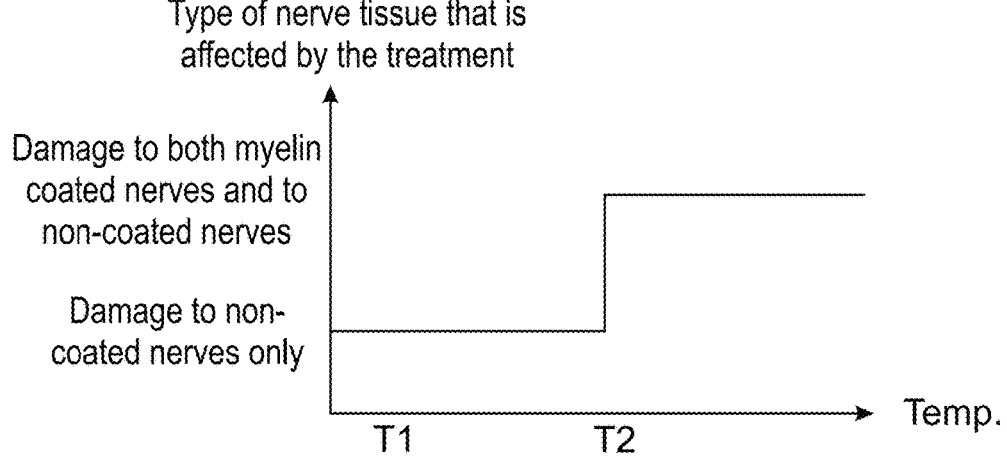

In some embodiments, applying selective treatment includes differentiating between nerves (607). Optionally, differentiating comprises not causing thermal damage to myelin coated nerves (609). The inventors have observed that by selecting a certain temperature profile, for example by denervating using a temperature above, for example, 47 degrees C., yet below, for example, 57 degrees C., thermal damage is caused to nerves that are not coated by myelin, while myelin coated nerves are not damaged. By increasing the temperature, for example to a temperature of 58 degrees C. or higher, myelin coated nerves are damaged. Differentiating between myelin coated and non coated nerves may provide an advantage when treating nerves which innervate the lung vasculature. According to Schelegle et al. (Respir Physiol Neurobiol. 2012 May 31; 181(3): 277-285. doi: 10.1016/j.resp.2012.04.003., "Vagal afferents contribute to exacerbated airway responses following ozone and allergen challenge") myelinated fibers initiate bronchodilation. FIG. 6B is a schematic graph illustrating selectively treating nerves by modifying a temperature profile. As explained hereinabove, when heating at certain temperature range T1, for example ranging between 47-57 degrees C., only non-coated nerves are damaged. When increasing the temperature to a range T2, for example ranging between 58-70 degrees C., both non-coated nerves and myelin coated nerves are thermally damaged.

In some embodiments, differentiating between nerves comprises identifying the vagus or its branches. A potential advantage of identifying the vagus may include reducing a risk of damaging or affecting the heart, for example due to heating of the vagus which may affect heart rate. Alternatively, the vagus and/or its branches are treated, for example vagal fibers are treated to affect dilation and/or constriction of the bronchi. In some embodiments, the vagus is identified by emission of short bursts of ultrasonic energy, which are capable of exciting the vagus to an extent that substantially does not cause damage to structures that are innervated by the vagus. In some cases, excitation of the vagus affects heart pulsation, and measuring a change in heart rate may provide an indication that the vagus is located within the range of the ultrasonic field emitted by the catheter. Additionally or alternatively, in some embodiments, branches of the vagus such as the recurrent laryngeal nerve are excited by emission of ultrasonic energy, and a response to the stimulation is assessed for identifying whether the vagus and/or one or more of its branches are located within the treatment region.

In some embodiments, for applying selective treatment, an external guiding element is used with the catheter device. Optionally, the external guiding element is positioned externally to the body, for example adjacent the patient's chest. In some embodiments, the guiding element comprises a receiver which receives signals from the catheter device, for example during treatment. Additionally or alternatively, the guiding element is configured to send data to the catheter device, for example to activate or deactivate emission. In some embodiments, the guiding element is in communication with the catheter's operating console. Optionally, the guiding element indicates a current position and/or orientation of the catheter to the console, and treatment is initiated and/or modified and/or ceased based on the indication.

While ultrasound energy, such as non-focused energy, may be specifically advantageous when targeting nerve tissue to modify nerve activity, selective targeting can be performed by using other energy forms and/or methods, such as RF, application of direct heat, and/or other energy forms or methods suitable to thermally affect the targeted nerves.

Feedback

Figure 7:
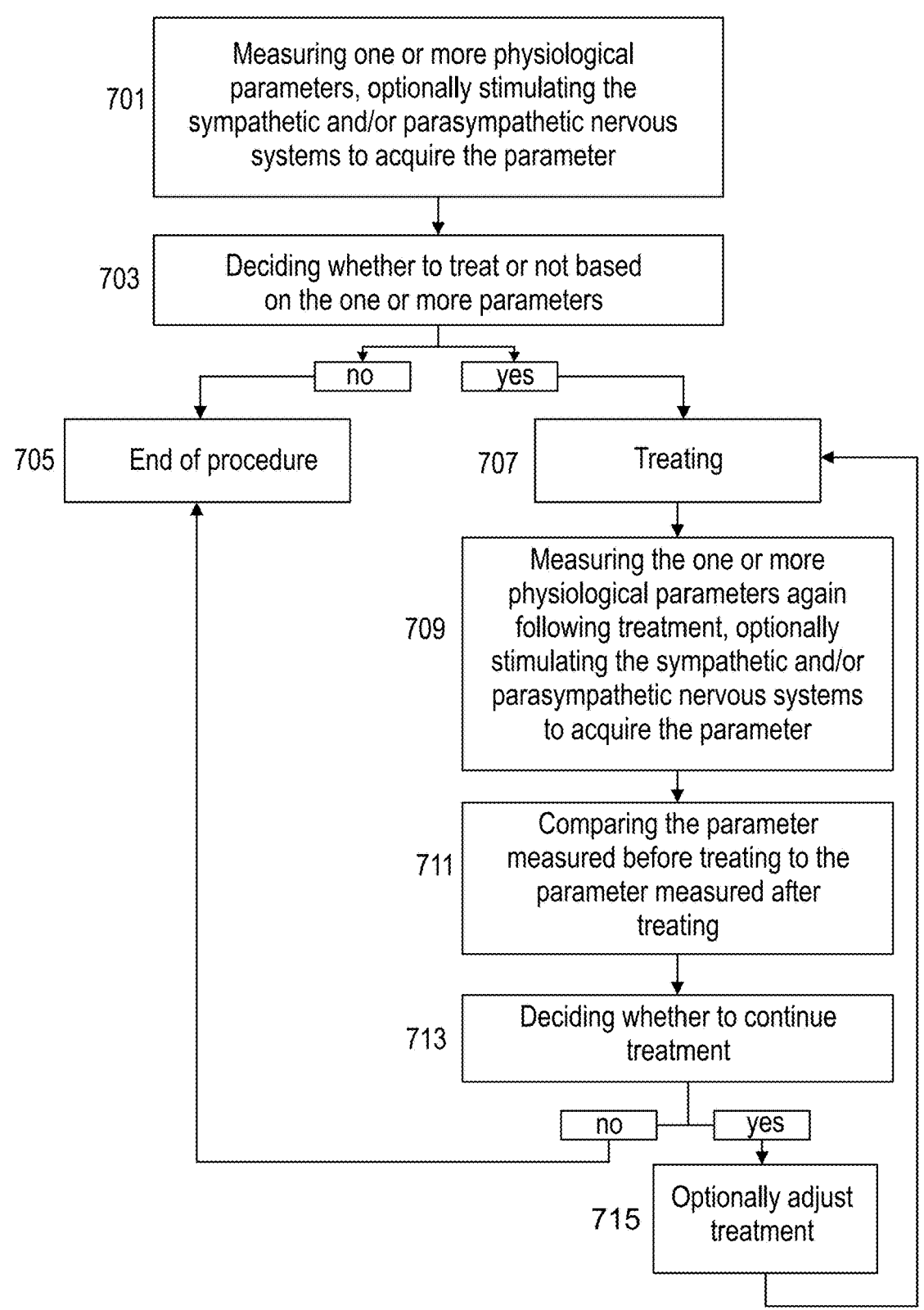

FIG. 7 is a flowchart of an exemplary feedback loop associated with a pulmonary denervation procedure, according to some embodiments of the invention. In some embodiments, the treatment is modified according to the feedback, for example treatment parameters such as one or more of intensity, duration, frequency, timing, and/or power may be adjusted based on the feedback.

In some embodiments, immediate feedback is obtained in real time. Optionally, feedback is obtained within time periods in between energy emissions. Additionally or alternatively, feedback is obtained before the catheter device is moved to a different location. Additionally or alternatively, feedback is obtained following an excitation and/or a set of excitations of the one or more transceivers, for example 30 seconds, 1 minute, 15 minutes, 1 hour or intermediate, shorter or longer time periods following excitation. In an example, immediate feedback includes observing a visible effect of treatment on the bronchi, such as bronchodilation or bronchoconstriction, which are expected to occur within a relatively short time period, such as 10-120 sec, for example 15 seconds, 30 seconds, 80 seconds or intermediate, longer or shorter time periods following ablation of the nerves which innervate the bronchi, such as the anterior and/or posterior pulmonary plexuses.

In some embodiments, additionally or alternatively to immediate feedback, long term feedback is obtained. Exemplary physiological parameters that can be assessed to obtain long term feedback for the denervation treatment may include one or more of blood pressure, cardiac output, artery wall thickness, artery flow resistance, lung volume, diastolic pressure, and/or other parameters.

In some embodiments, physiological and/or functional changes to the heart, pulmonary artery and/or bronchus are monitored. Optionally, changes are assessed to indicate the effect of treatment. In some embodiments, one or more physiological parameters are measured. Optionally, the parameters are used as control parameters, for deciding whether to continue the treatment and/or whether to modify the treatment.

For example, when monitoring the heart, a parameter such as heart rate may be measured. When monitoring the pulmonary artery, one or more parameters such as the artery diameter, arterial blood pressure, blood flow velocity and/or rate, and/or artery stiffness may be measured and/or estimated. When monitoring the bronchus, parameters such as the bronchus diameter and/or the flow rate of air through may be measured and/or estimated.

In some embodiments, one or more parameters are monitored continuously. In an example, heart rate is measured continuously, and if arrhythmia is detected, energy emission from the device is ceased. Alternatively, a parameter is measured once. Alternatively, a parameter is measured intermittently, for example every 30 seconds, every 2 minutes, every 15 minutes, or intermediate, shorter or longer time intervals.

In some embodiments, measurements obtained from the left and right pulmonary arteries are compared to each other, for example to detect a change in the branch that was treated with respect to the branch that was not treated.

In some embodiments, feedback is acquired by receiving echo signals, such as echo signals reflected by the artery wall, and processing the signals. Optionally, processing comprises estimating a physiological condition of the artery, for example assessing vasoconstriction or vasodilation based on an estimation of the artery diameter.

In some embodiments, feedback is acquired using a sensor, for example a pressure sensor, a flow sensor, and/or a temperature sensor. Optionally, the sensor is coupled to the catheter device. Additionally or alternatively, a sensor is positioned in the artery separately from the catheter. In some embodiments, one or more external sensors are used, such as a sensor adapted for detecting breathing of the patient. In some embodiments, a guide wire comprising one more sensors is delivered through a lumen of the catheter device.

It is noted that where "measurements" or "measuring" are referred to, these may include estimating and/or otherwise indicating a selected parameter.

In some embodiments, one or more physiological parameters are measured (701). In some embodiments, parameters are obtained before treatment. Optionally, the parameters are used as reference (or base line) measurements. In an example, a baseline indication of blood pressure within the pulmonary artery is measured.

In some embodiments, measuring includes one or more of, for example:

assessing heart function, such as heart rate, for example using electrocardiography. In some cases, a change in heart rate is associated with treatment of the vagus and/or vagal nerves. In some cases, a change in heart rate may include arrhythmia.

measuring muscle sympathetic nerve activity (MSNA).

measuring arterial blood pressure and/or other hemodynamic properties, such as mean pulmonary arterial pressure, for example using a "Swan-Ganz" catheter, and/or a pressure sensor mounted onto the catheter device and/or onto a guide wire inserted along with device, for example through a lumen of the device.

measuring artery dimensions, such as diameter, by processing echo signals received by the catheter device and/or by using angiography.

measuring arterial stiffness, for example by processing of echo signals received on the device to determine a movement pattern of the artery wall.

measuring arterial resistance to flow, for example by assessing a difference between pulmonary artery pressure and diastolic left ventricle pressure.

measuring bronchial dimensions, such as diameter, for example by using a balloon. In some embodiments, the balloon is filled with fluid, and a volume of the filled balloon and/or inflation pressure of the balloon is measured for assessing bronchial dimension. Additionally or alternatively, bronchial dimensions are measured using angiography. Additionally or alternatively, dimensions of the bronchus are estimated based on returning echo signals. Optionally, the emitting catheter is located within the pulmonary artery.

measuring air flow (for example measuring parameters such as flow volume, flow rate).

In some embodiments, measuring includes stimulating the sympathetic and/or parasympathetic nervous systems. Optionally, the physiological parameter is a parameter measured in response to the stimulation. In some embodiments, one or more nerves are stimulated to assess their innervating function. Optionally, the nerves that are stimulated are targeted during the treatment. Additionally or alternatively, different nerves than the ones that were stimulated are targeted during treatment.

In some embodiments, stimulating involves one or more of, for example:

using the ultrasonic catheter device for stimulating the nerves. In some embodiments, the device is configured to apply ultrasound energy having parameters suitable for causing a stimulation effect, which does not thermally damage the nerve tissue. Optionally, parameters such as frequency, power, intensity, temperature range, beam shape, catheter location and/or orientation and/or other parameters are selected to produce a stimulating effect, while reducing or preventing thermal damage to the nerves. Optionally, the selected set of parameters defines a stimulating profile that is different from the treating profile.

applying pressure onto the artery wall, for example by inflating a balloon, which may cause spasm of the artery.

blocking or partially blocking the blood flow, for example by inflating a balloon. Blocking the blood flow may affect the resistance of the artery walls.

electrically stimulating the nerves. In some embodiments, electrification is provided using one or more electrodes. Optionally, the electrodes are delivered over a balloon which is inflated within the artery. Additionally or alternately, electrification is applied externally.

heating and/or cooling the trachea which may cause bronchoconstriction.

injecting one or more substances which have a stimulating effect, for example injecting thromboxane A, which induces constriction of the artery which may thereby increase blood pressure.

injecting air bubbles which may have a similar constricting effect on the artery.

In some embodiments, optionally based on the measurement, a decision is made whether or not to treat (703). In some cases, the measured parameter may indicate that treatment (or, in some cases, additional treatment) is not required, and the procedure will end (705). Alternatively, treatment is applied (707). Optionally, parameters of the treatment (for example frequency, power, intensity, duration, temperature profile, and/or other parameters) are selected according to the measurement. Optionally, the targeted nerves are selected according to the measurement. Optionally, a location of the catheter in the artery is selected according to the measurement.

In some embodiments, the one or more parameters that were measured before the treatment are measured again after the treatment. In some cases, the parameters are measured following emission of a pulse and/or a set of pulses, for example measured 30 seconds, 1 minute, 15 minutes, 1 hour, 3 hours or intermediate, longer or shorter time periods following emission. Additionally or alternatively, the parameters are measured before moving the catheter to a different location.

In some embodiments, parameters acquired before the treatment are compared to the parameters acquired after the treatment (711). In some cases, a change between the response of the nervous system to stimulation before treatment and the response of the system after treatment is observed. Optionally, a threshold is set for defining if the change is significant and indicates that the treatment was effective. Exemplary thresholds may include: a mean diameter of the artery increasing by at least 5%, a heart rate being slowed down by at least 10%, flow pressure in the artery decreasing by at least 20%.

In some embodiments, a decision is made whether or not to continue treatment (713). Optionally, if the parameter comparison indicates that a desired change was observed, for example a mean diameter of the artery increased, for example by at least 5%, 15%, 20% or intermediate, larger or smaller percentages, the treatment is not continued (705). Alternatively, if the comparison indicates that no or partial effects of the treatment were achieved, the treatment is continued. Optionally, treatment parameters are adjusted according to the observed change.

In the following, an exemplary feedback controlled operation of the catheter is described, in which blood pressure in the pulmonary artery is the physiological control parameter that is measured.

In some embodiments, the pressure is measured using an intravascular pressure sensor. Optionally, devices and methods known in the art are used for assessing the intravascular pressure. Additionally or alternatively, in some embodiments, the catheter device is equipped with a pressure sensor, and pressure is measured by the device.

In some embodiments, flow rate, which depends, at least in part, on the resistance of the artery walls to the flow, is estimated, and the arterial pressure is calculated using the flow rate. Optionally, flow rate is estimated using one or more measurements obtained by the catheter device. In some embodiments, flow rate is calculated using the estimated artery cross section area and the flow velocity. Optionally, the artery cross section is estimated using an artery diameter estimation, which was optionally estimated by analysis of echo signals reflected by the artery walls and received by the catheter. Optionally, blood flow velocity is measured using a Doppler device, and/or by using angiography, and/or by thermodilution. Optionally, the catheter device comprises an integrated flow velocity measurement mechanism.

In some embodiments, once a reference pressure measurement is obtained, a balloon is inflated in the artery to apply pressure on at least a portion of the artery wall. In some cases, the applied pressure stimulates the nerves, activating innervations which may cause, for example, spasm of the artery. In some embodiments, the pressure is measured again, for example immediately after stimulation, to assess to the response of the artery to stimulation.

In some embodiments, treatment is applied. In some embodiments, to gain feedback following treatment, arterial pressure is measured again. Optionally, stimulation using the balloon is repeated, and the pressure measurements obtained following treatment are compared to the pressure measurements obtained before the treatment. If a change in pressure above a certain threshold is observed, for example the pressure is reduced by at least 5%, at least 15%, at least 50%, at least 70% or intermediate, higher or lower percentages, the treatment is completed. If a sufficient change is not observed, treatment may be repeated, and parameters of the treatment may be modified according to the observed change in attempt to increase the efficiency of the next treatment.

In another exemplary feedback controlled operation regime, the bronchus diameter is measured. Optionally, the diameter is measured continuously. Optionally, the diameter is measured using the catheter device. In some embodiments, the device is positioned within the pulmonary artery, and measurements of the bronchus are performed from within the artery. Treatment is then applied, for example with a gradually increasing intensity level, in parallel to monitoring of the bronchus diameter. Optionally, the treatment is modified based on the measured diameter. In some embodiments, treatment is ceased when reaching a certain intensity level, for example an intensity level above which myelin coated fibers are damaged, since damage to myelin coated fibers may cause constriction instead the desired dilation of the bronchus. In some cases, dilation of the bronchus is achieved by damaging the non-myelin coated fibers, which are prone to thermal damage more than the myelin coated fibers.

The inventors have performed experiments in swine models to obtain a feedback acquiring protocol, in which the parameters are selected to indicate a change in the hypertension condition.

Exemplary Configurations of an Ultrasonic Catheter

FIGS. 8A-8F are various configurations of an ultrasonic catheter device, according to some embodiments of the invention.

In some embodiments, a structure of the device is selected such as to reduce unwanted movement of the device. It is assumed that unwanted movement (i.e. movement beyond a small, allowable range of movement may reduce the efficiency of the treatment, by potentially disrupting the ability to apply a minimal energy intensity level over a minimal period of time which are sufficient to cause a desired effect on the tissue.

In some embodiments, a structure of the device is selected to damp movement caused by heart pulsation, which may move the device for example because at least a portion of the catheter shaft is passed through the heart (such as through the right ventricle) when a distal portion of the catheter is positioned in the pulmonary artery. In some embodiments, axial decoupling or partial axial decoupling is provided between a distal portion of the catheter, which includes the head with the ultrasonic transceivers, and a proximal portion of the catheter.

In some embodiments, a structure is selected to provide damping of movement on one hand, but on the other hand to enable transferring of torque from a proximal portion of the catheter (for example from a handle positioned externally to the body) towards the distal end of the catheter.

In some embodiments, at least a portion of the shaft is rigid enough to enable maneuvering the catheter, for example advancing the catheter within the artery. In some embodiments, the shaft comprises one or more flexible portions, facilitating advancing the device along curves of the artery.

Figure 8A:
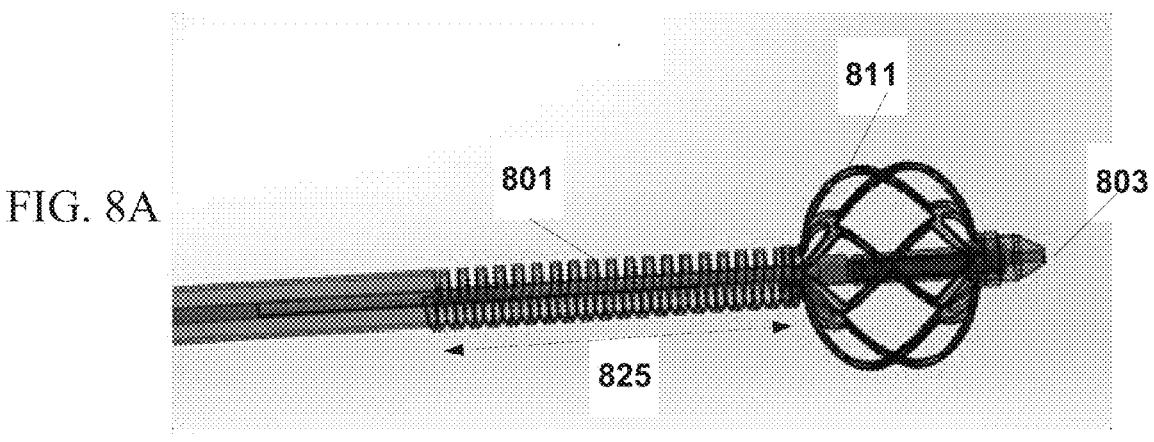

In some embodiments, movement damping is provided by a coil 801, for example as shown in FIG. 8A. Optionally, the coil is positioned in proximity to a distal end 803 of the catheter. Optionally, a length 825 of coil 801 is selected according to an expected movement range of head portion 805, for example movement due to heart contraction. In an example, length 825 is selected according to a length of a catheter portion that is most subjected to movement and/or proximal to that part.

Figure 8B:
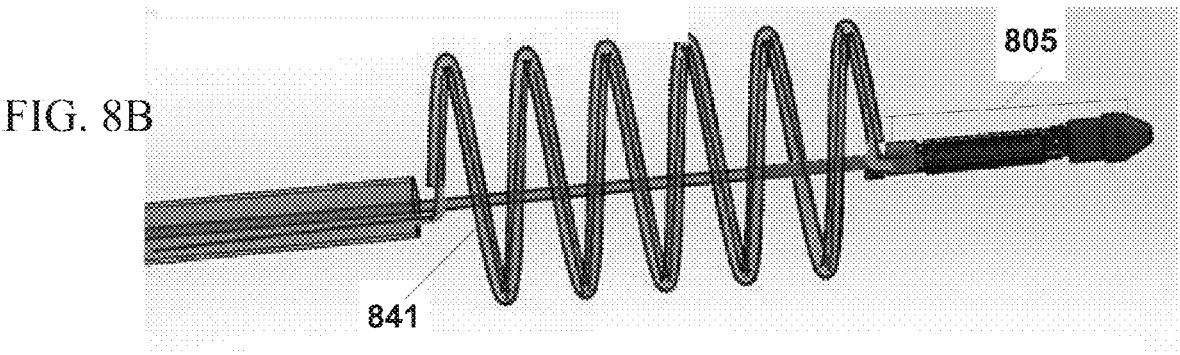

In some embodiments, for example as shown in FIG. 8B, a coil 841 is positioned to reduce movement of head portion 805, for example by extending to a diameter large enough to engage the walls of the artery.

Figure 8C:
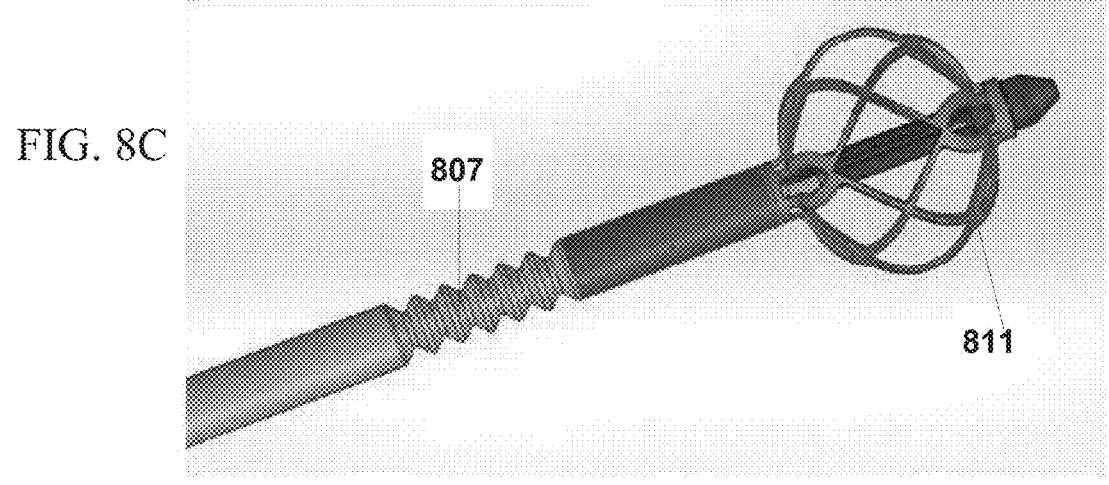

In some embodiments, movement damping is provided by an accordion like portion of the shaft 807, for example as shown in FIG. 8C. In some embodiments, movement damping is provided by a telescopic shaft assembly 809, for example as shown in FIGS. 8D1 and 8D2.

In some embodiments, the catheter device is used with a positioning element. Optionally, the positioning element is shaped to temporarily anchor the device at a certain location and/or orientation. Optionally, the positioning element is shaped to fixate at least a portion of the device in place. In some embodiments, the positioning element is structured to allow blood to flow through the element, for example allowing blood to flow over a surface of the transceivers to cool the transceivers. In some embodiments the positioning element is structured to push the device, such as push head portion 805, away from one or more artery walls. Optionally, the positioning element centers the device with respect to artery walls.

In some embodiments, the positioning element is delivered into the artery in a collapsed configuration, and is expanded in the artery, for example at a location where treatment is applied. Optionally, the positioning element is expanded in a radially outward direction. In some embodiments, the positioning element is expanded mechanically, for example by pulling at least a portion of the catheter shaft, which is coupled to the positioning element, in a proximal direction, and/or by inflating a balloon within the positioning element, and/or by using an elastic element, such as a spring. In some embodiments, for example as shown in FIGS. 8E1 and 8E2, the positioning element is elastic, and is compressibly folded within a shaft 815 of the catheter. Optionally, when shaft 815 is pulled in a proximal direction, the positioning element is released and is free to expand outwardly.

In some embodiments, for example as shown in FIGS. 8A, 8C and 8D1, a positioning element is shaped as a braided cage 811. Optionally, the braided cage 811 is configured to fixate the catheter device, such as a head portion of the device, with respect to the targeted tissue. In some embodiments, cage 811 is expandable to a diameter in which it abuts against opposing artery walls, reducing axial and/or rotational movement of the catheter device. In some embodiments, cage 811 is formed of a slotted portion of the external shaft of the catheter, which defines expandable leaflets for example as described hereinabove with respect to a distancing device. Additionally or alternatively, cage 811 is threaded onto and/or mounted on the catheter shaft. Optionally, the cage is formed of a shape memory alloy such as nitinol.

In some embodiments, a positioning element comprises a circumferential arrangement of leaflets 813, for example as shown in FIGS. 8E1, 8F1 and 8F2.

In an exemplary embodiment of the catheter device, for example as shown in FIGS. 8F1 and 8F2, an ultrasonic transceiver 817 is coupled to a radially inward facing wall of leaflet 813. Optionally, an emitting surface of transceiver

817 faces a generally central direction, such as towards shaft 821 of the positioning element. In some embodiments, an energy field 819 produced by transceiver 817 is effective to treat nerves located in a radially opposing direction of the artery, for example nerves adjacent and/or beyond an artery wall portion located across from transceiver 817. Optionally, leaflets 813 are arranged with respect to each other in a configuration which permits energy emission in between the leaflets. In some embodiments, a thickness of leaflet 813 is selected to be small enough to reduce the amount of heat absorbed by the leaflet material (e.g. nitinol) during emission of transceiver 817, thereby reducing the amount of heat which may be transferred by the leaflet to a vessel wall that is contact with the leaflet.

In some embodiments, one or more transceivers 817 face a central direction. Additionally or alternatively, one or more transceivers 817 face a direction which is offset from the center.

In some embodiments, leaflets 813 are expandable by retracting a distal tip 827 of the positioning element in a proximal direction, towards a shaft 829 of the catheter. Additionally or alternatively, leaflets 813 are contracted and brought closer to shaft 821 of the positioning element by advancing distal tip 827 in a distal direction.

In some embodiments, the catheter is equipped with a hydrodynamic element, which is suitable, for example, for stabilizing the catheter within the pulmonary trunk, which has a relatively large diameter and carries vast amounts of blood.

A General Method for Treating Nerves Using an Ultrasonic Catheter in the Trachea FIG. 9 is a flowchart a method for treating nerves by positioning an ultrasonic device in the trachea, according to some embodiments of the invention.

In some embodiments, nerve treatment is applied from a tracheal position, for example to treat one or more conditions such as hypertension, asthma, and/or COPD (901, 903).

In some embodiments, an ultrasonic device is introduced to the trachea (905). Since the trachea is a tube like structure which delivers air to the lungs, in some embodiments, the ultrasonic device is adapted to treat surrounding nerves without blocking the air way.

In some embodiments, the ultrasonic device is equipped with a fluid circulation system. Optionally, the fluid in the circulation system (e.g. water, saline,) serves as a medium for transferring the ultrasonic energy from the transceivers to the trachea wall.

In some embodiments, fluid circulation system is configured to provide heating and/or cooling. Optionally, heating and cooling are applied simultaneously, for example cooling is applied to prevent over heating of the one or more transceivers, and heating is applied to enhance the thermal damage effect of the ultrasound energy, for example increasing the depth of the effective field in the tissue.

In some embodiments, when positioning the device in the trachea (907), the location and/or orientation of the catheter device are selected according to the relative location of other anatomical structures. For example, in some embodiments, the cartilage rings of the trachea are identified, and treatment is applied in between the rings. Optionally, the cartilage rings are identified by analyzing echo signals reflected by the cartilage tissue and received by the one or more transceivers. In another example, the catheter device is positioned in the trachea at a location in which it is effective to treat pulmonary artery nerves. Optionally, the pulmonary artery is identified according to echo signal reflections, for example signals that indicate pulsed movement of the artery walls.

In some embodiments, steps 909-913 are similar to steps 109-113 described hereinabove in FIG. 1. For treating in the trachea, various treatment parameters may be modified, for example frequency, intensity, beam shape, and/or other parameters.

An ultrasonic Catheter Equipped With One or More Balloons

FIGS. 10A-10B show an ultrasonic catheter used with one or more balloons, according to some embodiments of the invention.

In some embodiments, as shown for example in FIG. 10A, one or more balloons 1001 are used with the catheter. Optionally, the balloons are symmetrically arranged with respect to a tube 1003 in which catheter 1007 is received, for example as shown in this figure. Alternatively, the balloons are arranged asymmetrically with respect to tube 1003.

In some embodiments, tube 1003 comprises one or more windows 1009, which are sized, shaped and/or positioned to expose the one or more transceivers 1011 of the catheter device.

In some embodiments, the balloons encompass the catheter circumferentially. Alternatively, as shown for example in this figure, the balloons are configured such that they extend along only some portions of the circumference of tube 1003. In some embodiments, the balloons are positioned such that the ultrasonic transceivers lie within spaces in between balloons. In some embodiments, a mechanical element such as one or more rods extend between a transceiver 1011 and a balloon 1001, for example extending to a wall of the balloon, to position the transceiver relative to the balloon, such as axially and/or radially centralize the transceiver with respect to the balloon.

In some embodiments, the balloons are filled with fluid. Optionally, the fluid is heated or cooled. In some embodiments, the fluid is cooled in order to cool the transceiver, allowing it to operate in relatively high intensities, optionally for relatively long periods of time. In some embodiments, the fluid is cooled or heated to control an extent of thermal damage to the tissue, for example heated to increase a depth of thermal damage or cooled to reduce a depth of thermal damage. In some embodiments, an operation console used with the catheter is programmed to activate cooling and/or heating of the fluid, for example by a heating element and/or a cooling element, such as a heating wire positioned within and/or in contact with the fluid in the balloon.

In some embodiments, the balloons are arranged to allow flow in between them and/or over the catheter shaft, such as over the surfaces of the transceivers. In some embodiments, for example when the device is used in the trachea, the balloons are arranged to allow air to flow over the transceivers and/or over the walls of the trachea to cool them. In some embodiments, for example when the device is used in the pulmonary artery, the balloons are arranged to allow blood to flow in between them, over the transceivers and/or adjacent the artery walls to cool them.

In some embodiments, a balloon 1001 is inflated until it contacts the wall of the organ in which the catheter is positioned (such as the pulmonary artery wall, trachea wall). In some embodiments, the balloon is coated with a material suitable to prevent damage to the wall. Optionally, the material is a medicine having a therapeutic effect on the wall, such as Paclitaxel or Heparin. Additionally or alternatively, the material softens the contact of the balloon with the wall, for example having a lubricating effect which reduces friction upon contact with the wall, to reduce a risk of damaging the wall. Exemplary materials for softening a contact between the balloon and wall tissue are acoustic gel, saline and/or water.

In some embodiments, one or more dimensions of the inflated balloon, such as, for example, a distance 1005 (as shown, for example, in the cross section of FIG. 10B) in which the balloon extends radially outwardly from the catheter shaft, are selected to provide for energy transfer towards the wall of the organ. In an example, distance 1005 is selected according to the wavelength of the emitted energy.

In some embodiments, the balloons, when inflated, keep the ultrasonic transceivers 1011 of the catheter away from the wall, such as the arterial or tracheal wall.

In some embodiments, a fluid which fills the balloon acts as a transferring medium for the ultrasonic energy. Optionally, a fluid with selected energy transfer characteristics is used. In some cases, energy emitted by the one or more transceivers is modified by the fluid medium when it is transferred through the balloon.

In some embodiments, a balloon 1001 comprises a circular cross section profile, a substantially trapezoidal cross section (for example as shown in this figure), a triangular cross section profile, or other.

In some embodiments, for example during introducing of the catheter into the body, the balloons are in a collapsed configuration. Optionally, the folded balloons are contained within compartments of the catheter, for example compartments configured along an external wall of the catheter shaft. In some embodiments, when the catheter is advanced to a desired location, the balloons are inflated, such as by injection of fluid and/or air. Alternatively, the balloons are introduced separately from the catheter device, for example they are threaded over the guiding sheath following insertion of the catheter. In some embodiments, an angioplasty-like balloon in which the one or more transceivers are contained and/or received is delivered to the target location, and inflated before and/or during energy emission.

FIGS. 11A-11B are an isometric view (11A) and a cross section view (11B) of an ultrasound catheter equipped with a multiple balloon assembly, according to some embodiments of the invention.

In some embodiments, the catheter device 1101 is used with a multiple balloon assembly. In some embodiments, the balloon assembly includes 2, 3, 4, 5, or a higher number of balloons. In the example shown herein, the balloon assembly comprises an internal balloon 1103, which surrounds transceivers 1111, and an external balloon 1105, which encompasses internal balloon 1103 at least in part. A potential advantage of an external balloon which extends only partially over an internal balloon and does not fully surround it may include reducing obstruction of blood flow through the vessel.

In some embodiments, the balloon assembly is adapted to provide heating and/or cooling. Optionally, fluid is circulated within each of the balloons, and is heated and/or cooled according to the need.

In an example, internal balloon 1103 is cooled, for example to cool the ultrasonic transceivers 1111 of the device, and external balloon 1105 is heated, for example to enhance the thermal effect of the emitted ultrasonic energy. A potential advantage of using a hot external balloon may include increasing a depth of the effective field in the tissue.

Distance 1109 is a distance between the internal balloon 1103 and the external balloon 1105. Gap 1107 is a gap between the internal balloon 1103 and the external balloon 1105.

In some embodiments, a temperature of the fluid within a balloon is selected between 10-43° C., such as 20 degrees, 35 degrees, 40 degrees or intermediate, higher or lower temperature. In an example, fluid is cooled to 10 degrees to provide cooling. In another example, fluid is heated to 40 degrees to provide heating.

A General Method for Treating Nerves Using an Ultrasonic Catheter in the Aorta FIG. 12 is a flowchart of a method for treating nerves, such as celiac ganglion nerves, by positioning the ultrasonic catheter device in the aorta.

In some embodiments, a patient is diagnosed with one or more of hypertension, congestive heart failure, atrial fibrillation, sleep apnea, and/or insulin resistance (1201). In some cases, a physician decides to treat the nerves of the celiac ganglion, which innervate most of the digestive tract, in attempt to treat the above conditions (1203).

In some embodiments, an ultrasonic catheter device is introduced to the aorta (1205). Optionally, the device is advanced until reaching the celiac artery ostium (1207). In some embodiments, the device is anchored in the selected position, for example using anchoring elements which provide radial and/or axial fixation to hold the device in a position suitable for treating the celiac ganglion.

Once the device is positioned in place, treatment is applied (1209) to denervate the celiac ganglia nerve tissue.

In an example, a frequency of the applied energy is selected according to a distance of the device from the celiac artery ostium. In an example, a lower frequency such as, for example, 8-13 MHz and/or a transceiver with a larger surface area will be used when the device is positioned at a relatively large distance from the ostium, for example, a distance above 3 mm, above 5 mm, above 7 mm, or intermediate, larger or smaller distances. Optionally, a higher frequency of, for example, 13-20 MHz is applied when treating closer target tissue, for example tissue closer than 3 mm, 5 mm, 7 mm or intermediate, larger or smaller distances from the ostium.

FIG. 13 illustrates an ultrasonic catheter positioned with the aorta for treating the celiac ganglion, according to some embodiments of the invention.

In some embodiments, device 1301 is introduced to the aorta 1303, and is advanced until reaching a location proximal to the celiac artery ostium 1305. In some embodiments, device 1301 is positioned such that transceiver 1307 is located at a distance 1309 from celiac ganglion 1311.

In some embodiments, device 1301 is unidirectional, and is rotated around its axis until transceiver 1307 faces celiac ganglion 1311.

In some embodiments, emission of ultrasound by the transceiver, such as unfocused ultrasound, produces a field 1313 which is effective to reach the celiac ganglion 1311, and thermally damage at least some of the nerve tissue of the ganglion.

In some embodiments, a positioning element such as wire 1315 is used with device 1301 to locate the device with respect to the celiac artery ostium. Optionally, positioning element 1315 sets an axial position of device 1301 along the artery in accordance with the celiac artery ostium. Addition-ally or alternatively, positioning element 1315 sets an angular orientation of transceiver 1307 suitable for targeting the celiac ganglion 1311.

It is noted that in some embodiments, nerve tissue other than the celiac ganglion may be treated, for example from an aortic position.

A Positioning Element of an Ultrasonic Catheter

FIG. 14 illustrates an ultrasonic catheter device comprising an element adapted for distancing the device away from a vessel wall and/or positioning the device at a selected location and/or orientation, according to some embodiments of the invention. In some embodiments, the element is used in the aorta, to set a position of the ultrasonic device with respect to a location of the celiac artery ostium and/or the celiac ganglion.

In an exemplary configuration of the device, a head 1401 comprising a plurality of transceivers 1403, such as 3 transceivers arranged in a triangular configuration, as shown herein, is positioned within a shaft, such as cylindrical shaft 1405. In some embodiments, shaft 1405 comprises one or more recesses 1407, through which at least a portion of a surface of a transceiver 1403 is exposed.

In some embodiments, a positioning element, for example a rod shaped element 1409, is used with the device. Optionally, positioning element 1409 protrudes externally from shaft 1405, in a radial direction. In some embodiments, positioning element 1409 pushes at least a portion of the device away from the wall of the aorta. In some embodiments, positioning element 1409 aligns the device with respect to the celiac artery ostium, to locate transceiver 1403 at a location suitable for ablating the celiac ganglion nerve tissue.

In some embodiments, positioning element 1409 is controlled by a handle configured at a proximal end of the catheter, externally to the body. Optionally, positioning element 1409 is advanced distally through shaft 1405. Optionally, positioning element 1409 is advanced to extend through a recess in shaft 1405, for example extending to a radial distance 1413. In some embodiments, positioning element 1409 is threaded over a guiding wire 1417.

In some embodiments, for example when setting an angular orientation of the device which is suitable for targeting the celiac ganglion, contrast liquid is injected through the one or more recesses of shaft 1405, and an imaging modality is used to identify the celiac artery ostium.

In some embodiments, the catheter device is introduced over a wire 1415. Optionally, the wire is advanced ahead of the device, and sets a location for applying the treatment. In some embodiments, a positioning mechanism includes axial rotation of the catheter device as it is advanced along the wire, changing the angular positioning of the transceivers until reaching the treatment location, in which the transceivers will face the targeted tissue direction. Optionally, angiography is performed to visualize the catheter and orient it accordingly.

FIGS. 15-19 are referred to hereinbelow in the Examples section.

FIGS. 20A-20D illustrate various mechanisms for positioning and/or orienting at least a head of the catheter, comprising the one or more ultrasonic transceivers at a selected position within the vessel, according to some embodiments of the invention. In some embodiments, one or more positioning parameters such as an orientation of the transceivers with respect to the target tissue, a distance of the transceivers from the vessel wall, an axial position in the vessel, an emitting direction and/or other positioning parameters are controlled, for example by the mechanisms shown herein.

Figures 20A, 20B:
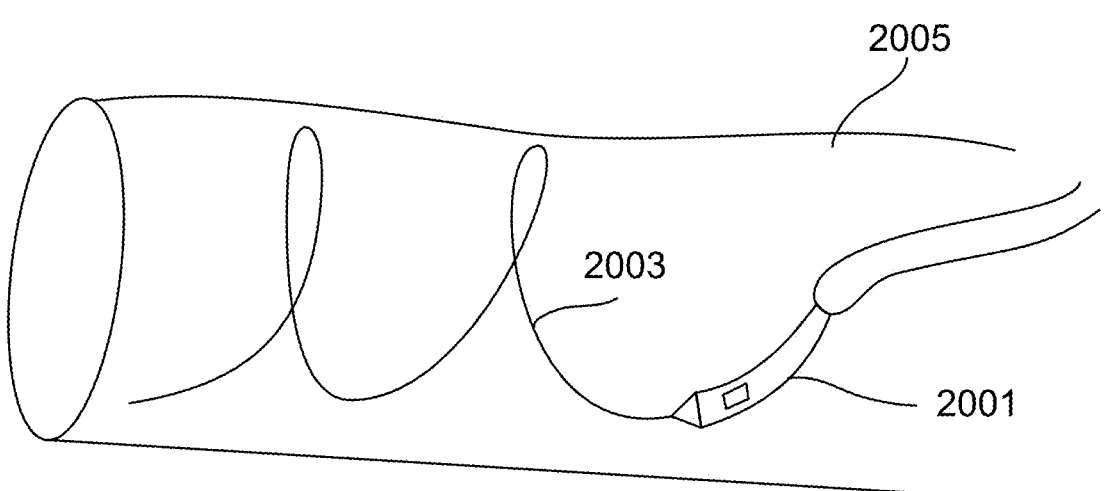
Figure 20C:
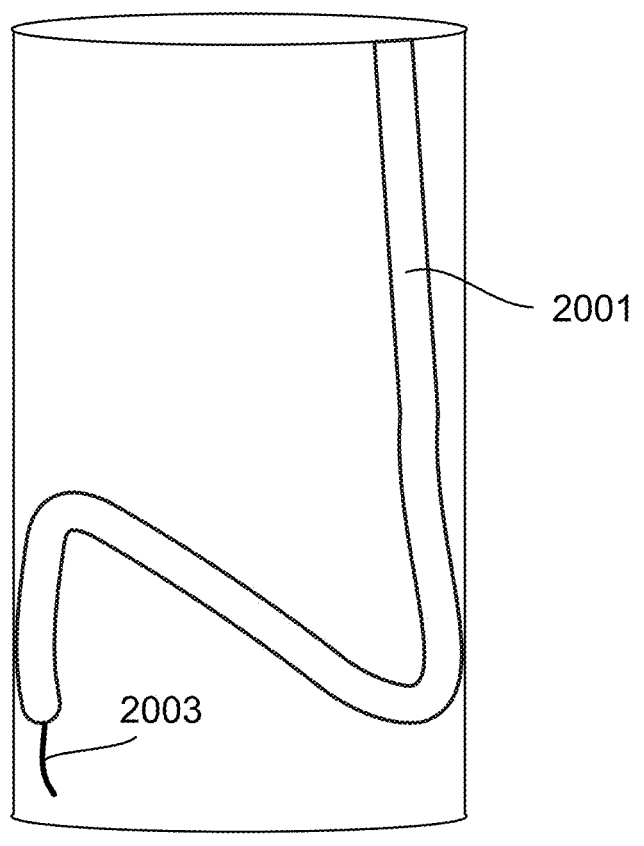

In FIGS. 20A-20C, catheter 2001 is introduced over a shaped guide wire 2003. Optionally, the guide wire is pre deformed to a desired configuration, such a spiral configuration for example as shown in FIG. 20A, or a Z-shape configuration as shown in FIG. 20B. Optionally, a diameter of the spiral configuration is selected according to a diameter of the vessel, so that when the catheter is advanced over the wire, at least a head of the catheter is maintained at a position in which it remains in proximity to the walls of vessel 2005. In an example, the spiral diameter is at least 5% smaller, 10% smaller, 20% smaller or intermediate, higher or lower percentages smaller than the vessel diameter. Additionally or alternatively, one or more dimensions of said spiral, such as the diameter, are selected according to dimensions of the catheter, such as the head diameter. In an example, the spiral diameter (i.e. a diameter of a single loop) is at least 4 times larger, 6 times larger, 3 times larger or intermediate, higher or smaller amounts larger than the catheter head diameter.

In some embodiments, a similar effect may be obtained by axially rotating the Z-shaped guide wire of FIG. 20B. Optionally, a long leg 2011 of the Z shaped wire comprises a length which is sufficient for keeping the catheter head away from a center of the vessel. FIG. 20C illustrates catheter 2001 introduced over the Z-shaped guide wire shown in FIG. 20B. Alternatively, a catheter comprising a shapeable shaft is deflected to a selected curvature, such as a Z-shape.

A potential advantage of the configurations described herein in FIGS. 20A-20C may include facilitating circumferential treatment of the vessel wall, by setting a path for advancement of the catheter which keeps the catheter head at a selected distance from the vessel wall, and optionally prevents it from being positioned at the center of the vessel. Alternatively, in some embodiments, it may be desirable to position the catheter head at the center of the vessel.

Figure 20D:
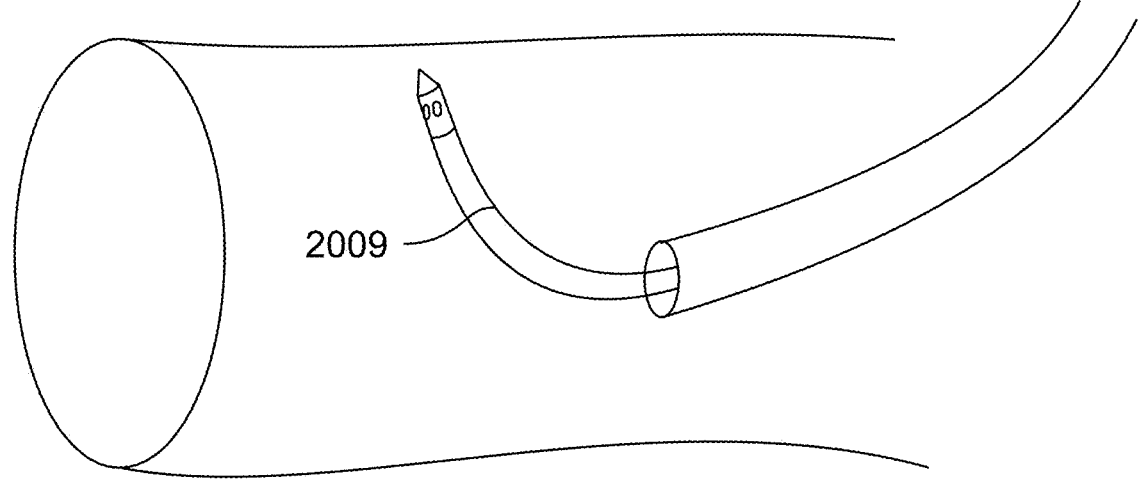

FIG. 20D illustrates a catheter comprising a mechanically deflectable shaft 2009, which can be bent with respect to the longitudinal axis, such as to direct the emitted energy to a selected location. In some embodiments, the shaft is bent to a configuration in which a portion of it leans against a wall of the blood vessel, pushing a more a distal portion of the catheter comprising the catheter head away from a center of the vessel, for example towards the opposite vessel wall.

In some embodiments, the shaft is deflected in vivo, for example by manipulating a pull cable which extends, for example, from a distal portion of the catheter to an operation handle of the catheter configured externally to the body. Additionally or alternatively, the catheter is predeformed, for example by threading it over a wire made of shape of memory material, such as nitinol.

It is noted that the devices and/or methods described herein may include features as disclosed, for example, in one or more of U.S. Provisional Application No. 61/826,583, filed 23 May 2013, U.S. Provisional Application No. 61/924, 778, filed 8 Jan. 2014, U.S. Provisional Application No. 61/924,848, filed 8 Jan. 2014, U.S. Provisional Application No. 61/931,838, filed 27 Jan. 2014, U.S. Provisional Application No. 61/931,890, filed 27 Jan. 2014, and PCT application number IL2014/050457, filed 22 May 2014, the contents of which are incorporated herein by reference.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

FIGS. 15-18 are histopathology images from a swine experiment. In the experiment, an ultrasonic catheter was introduced to the pulmonary artery, and a plurality of nerve regions, distributed at various distances from the artery, were treated, according to some embodiments of the invention.

In the images presented herein, a blue arrow bar indicates a minimal distance from the lumen of the pulmonary artery to non-targeted tissue, for example the lung or trachea; a green arrow bar indicates a distance from the lumen of the artery to the nerves that are targeted; a black arrow bar indicates a maximal distance of a region of nerves that were thermally affected by the treatment; a green line is used for bordering the targeted nerve regions; a black line is used for bordering the thermally affected nerve regions.

Each of the images includes a drawing, on the top left corner of the image, indicating a current position of the ultrasonic device in the pulmonary artery. In these examples, the catheter was positioned in the right pulmonary artery, but can also be positioned in the left pulmonary artery, pulmonary trunk and/or bifurcation.

Figure 15:
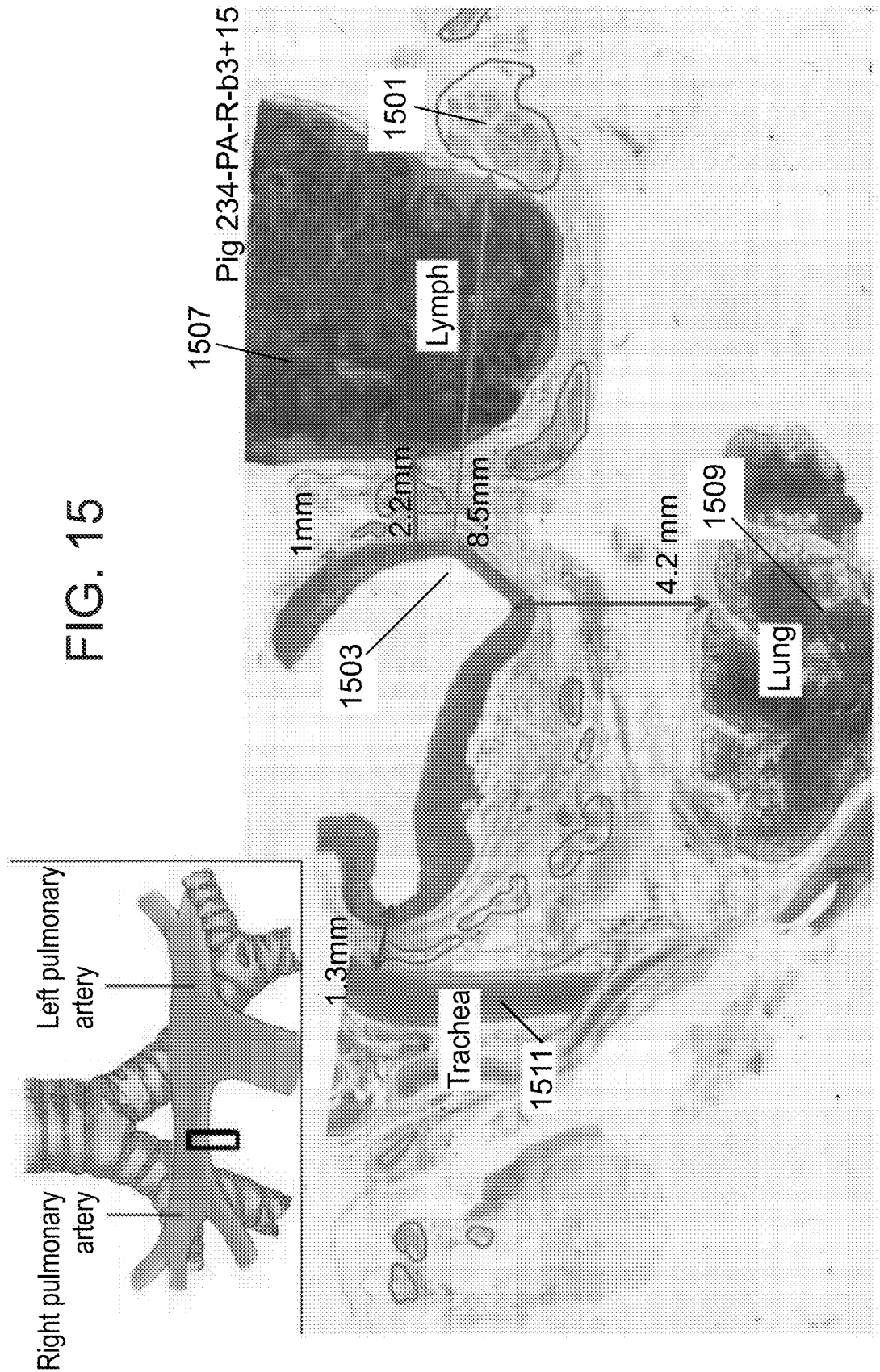

In FIG. 15, 1501 is one of the targeted nerve bundles. The bundle is located about 8.5 mm from the pulmonary artery lumen 1503, for example from a lumen location adjacent the artery wall, such as close the intima layer of the wall. Lymph 1507 is located between nerve bundle 1501 and artery 1503. In some embodiments, treatment parameters are selected to effectively target a nerve bundle such as bundle 1501, while reducing or preventing damage to the lymph 1507.

In some embodiments, the parameters are selected so that the applied energy does not damage the lung 1509 and/or the trachea 1511. Optionally, organs such as the lung and/or trachea are identified, using the device, based on their reflection, and a treatment location and/or treatment parameters are selected based on the detected location.

Figure 16:
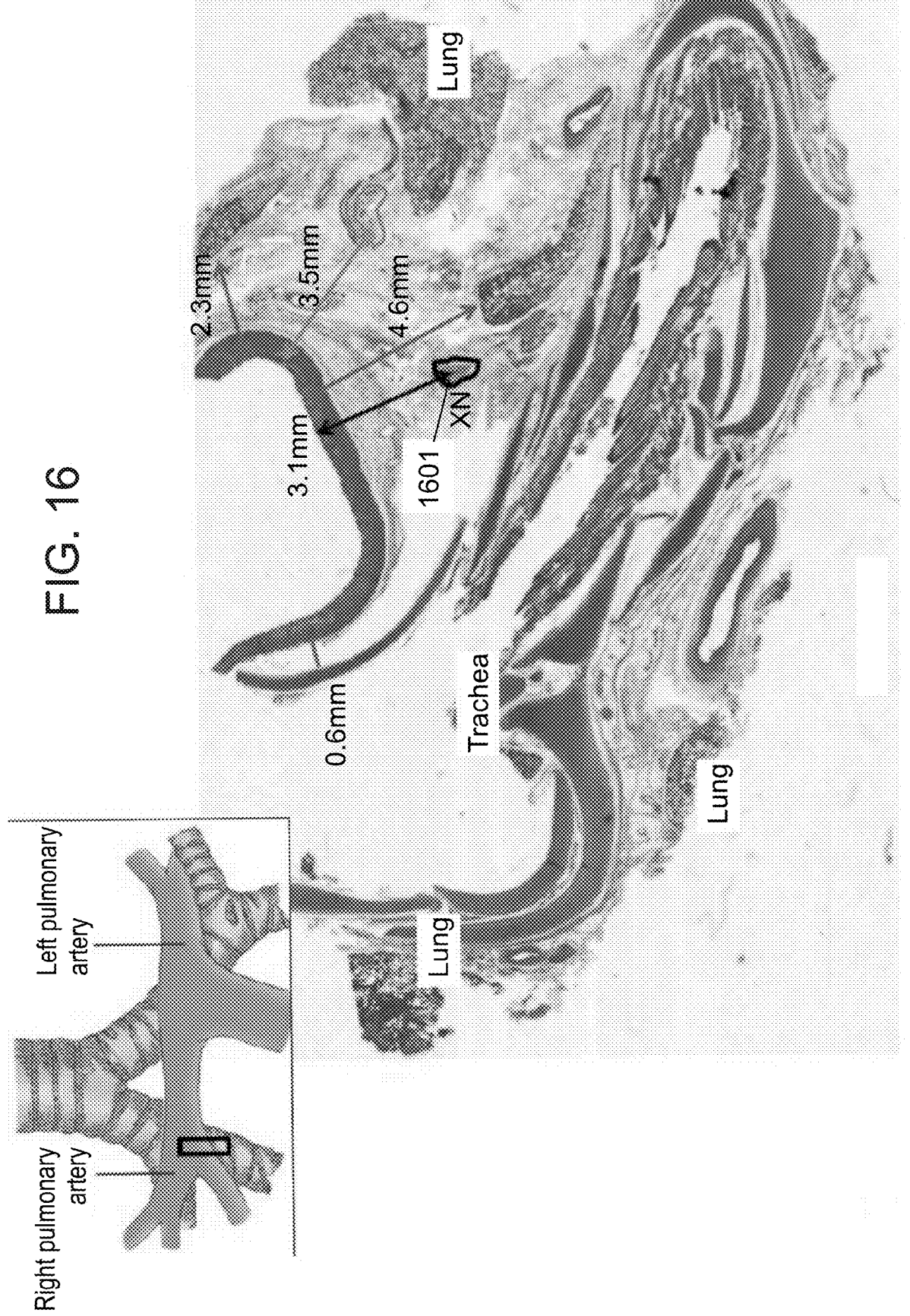

FIG. 16 shows an isolated nerve 1601 which was selectively targeted by the treatment and thermally damaged by the ultrasonic energy. No damage to surrounding nerves and other tissue was observed.

Figure 17:
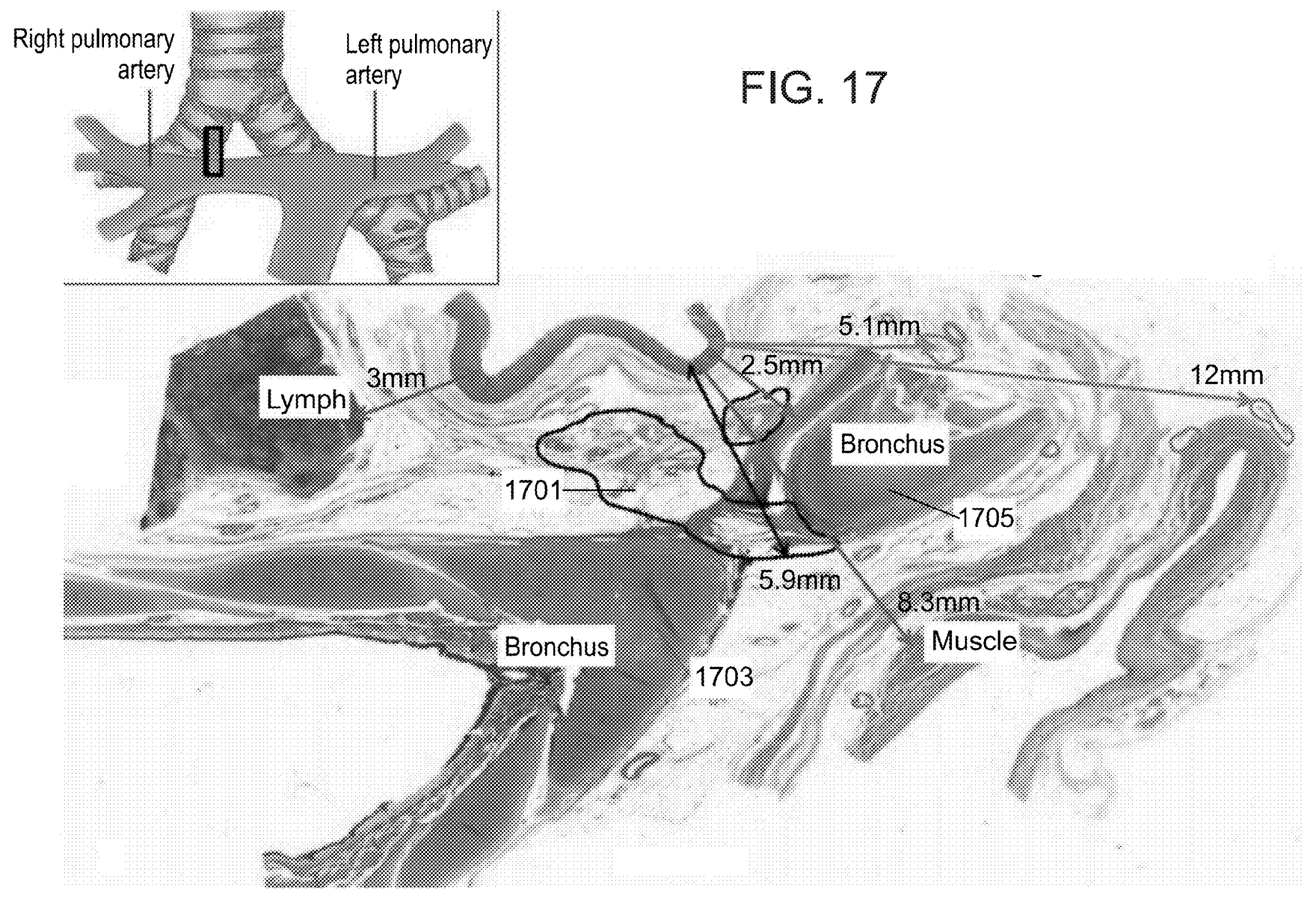

FIG. 17 shows an elongated thermally damaged area 1701 extending to a maximal distance of about 5.9 mm from the artery lumen. Damaged area 1701 is a connective tissue between two bronchi, 1703 and 1705. In this case, no damage was observed to the bronchi themselves, but only to the nerves of the connective tissue in between the bronchi.

Figure 18:
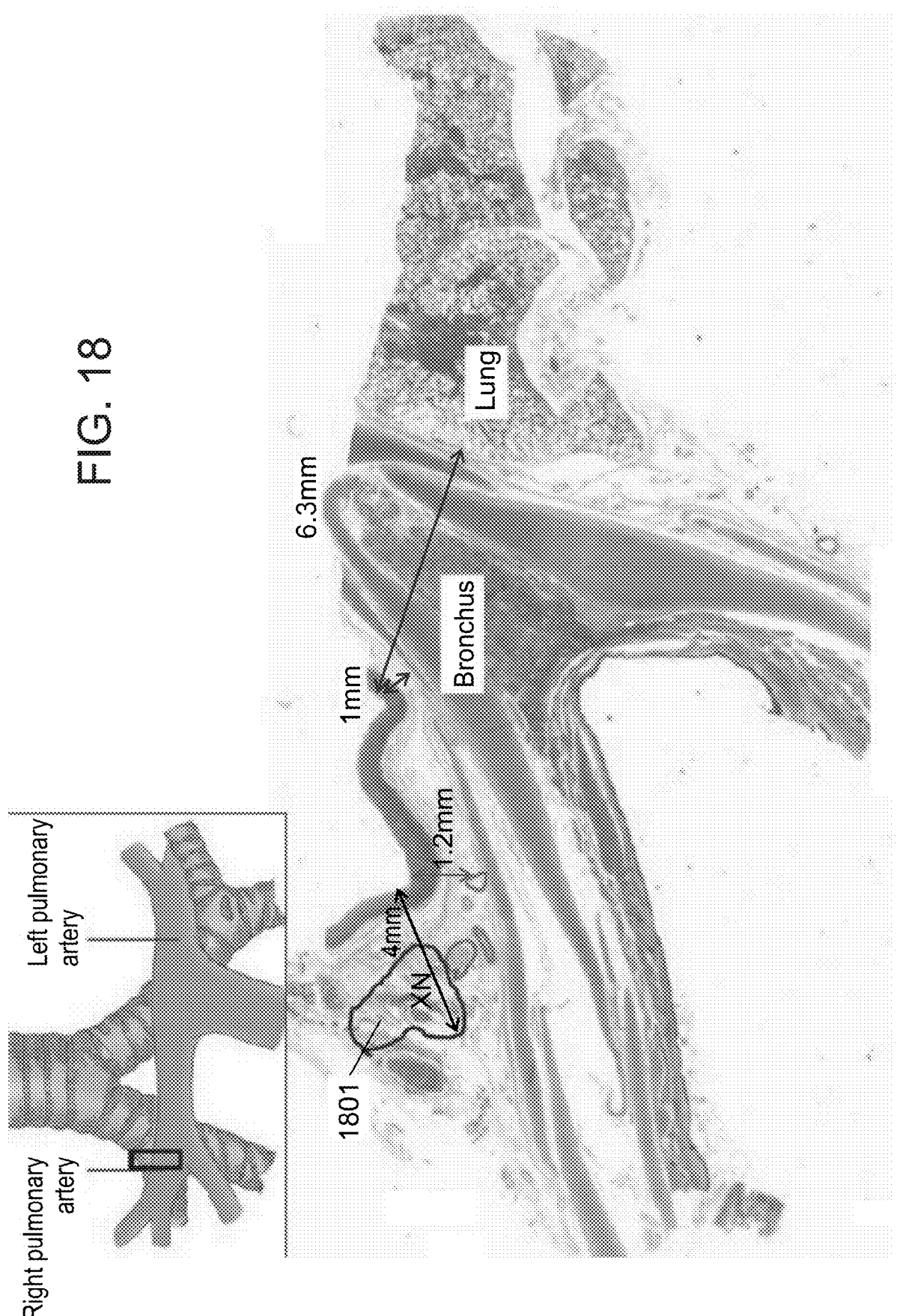

In FIG. 18, a relatively large nerve tissue region 1801, extending over an area of approximately 4 mm^2 was targeted and thermally damaged. Nearly no damage to surrounding tissue was observed.

FIG. 19 is a histopathology image from a swine experiment in which the celiac ganglion was targeted from an aorta location, according to some embodiments of the invention.

In this experiment, the ultrasonic catheter was introduced to the lumen of the aorta 1901, and positioned to treat the one or both of the celiac ganglia, 1903 and 1905. The first ganglion 1903 was located about 4.9 mm from the aortic lumen, and the second ganglion 1905 was located about 7.8 mm from the lumen. At the borders of the thermally damaged area protein denaturation was observed, indicating that the tissue was heated to a temperature above 55 degrees Celsius. Tissues that were close to the thermally damaged area, such as the ganglia, were thereby heated to a lower temperature, yet a temperature sufficient to cause at least some thermal damage to the nerves of the ganglia, for example a temperature above 47 degrees Celsius. In the described experiment, ultrasound at an intensity of 40 W/cm^2 was applied.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A method for selectively targeting nerve tissue, comprising:

introducing a catheter comprising one or more ultrasonic transceivers to a pulmonary artery lumen;

configuring an operating console of said catheter to activate said catheter to selectively damage nerves that are not coated by myelin, by emitting a field of unfocused ultrasound energy, wherein said emitted field of unfocused ultrasound energy is effective to selectively damage said nerves not coated by myelin at a distance larger than 12 mm from a wall of said pulmonary artery;

producing a temperature profile ranging between 47-57 degrees C. in said nerves by said catheter by emitting said field of unfocused ultrasound energy at frequency, intensity and duration selected to thermally damage said nerves not coated by myelin by said emitted field of unfocused ultrasound energy without causing bronchus constriction;

measuring a body lumen diameter while emitting the field of unfocused ultrasound energy, and modifying at least one of said frequency, intensity and duration of said ultrasound energy in accordance with the body lumen diameter.

2. The method according to claim 1, wherein myelin coated nerves remain substantially undamaged.

3. The method according to claim 1, wherein said frequency is between 8-13 MHz, and said intensity is between 35-65 W/cm^2.

4. The method according to claim 1, comprising, prior to said introducing, diagnosing a patient with at least one of: pulmonary hypertension, asthma and COPD.

5. The method according to claim 1, wherein the body lumen diameter is a bronchus diameter.

6. The method according to claim 1, comprising positioning said one or more ultrasonic transceivers away from a wall of said pulmonary artery lumen to allow blood to flow between said transceivers and said wall.

7. The method according to claim 1, comprising stabilizing said catheter at a treatment location within said pulmonary artery lumen by anchoring said catheter.

8. The method according to claim 1, comprising positioning said catheter within the main pulmonary artery, right pulmonary artery or left pulmonary artery at the vicinity of a bifurcation.

9. The method according to claim 8, wherein said positioning is at a location that is least subjected to movement due to heart pulsation.

10. The method according to claim 8, comprising anchoring said catheter to a tissue or organ which moves in a synchronized manner to the targeted nerve tissue.

11. The method according to claim 1, wherein said emitting comprises targeting sympathetic nerves, nerve segments and/or nerve plexuses which innervate the pulmonary vasculature.

12. The method according to claim 11, wherein said nerve plexuses are selected from the group of: a left coronary plexus, a right coronary plexus, a right atrial plexus, a left atrial plexus, a right pulmonary plexus, and a left pulmonary plexus.

13. The method according to claim 1, wherein said introducing comprises percutaneously introducing said catheter over a guide wire into the right atrium, via the right ventricle and into the main pulmonary artery.

14. The method according to claim 1, wherein said catheter comprises a 4F-11F diameter.

15. The method according to claim 1, comprising rotating said catheter axially within said pulmonary artery lumen to treat different circumferential segments of the artery wall.

16. The method according to claim 1, wherein said emitting is by 3-6 transceivers, each transceiver facing a different direction, each transceiver comprising a flat emitting surface.

17. The method according to claim 1, comprising, prior to said emitting, identifying specific nerves according to their innervating function, and targeting said nerves.

18. The method according to claim 1, wherein said method is a method for selectively targeting nerve tissue innervating lung vasculature, and wherein said selected frequency, intensity and duration of said emitted field of unfocused ultrasound energy are selected not to damage myelinated nerves, and without causing damage to tissue of said pulmonary artery wall.

19. The method of claim 18, wherein said selectively damage of said nerves not coated by said myelin results with bronchodilation.

20. The method according to claim 18, wherein said selected frequency, intensity and duration of said emitted field of unfocused ultrasound energy are selected not to damage a lung, a trachea and/or bronchi.

21. The method of claim 1, wherein said emitting comprises emitting said field of unfocused ultrasound energy to cover a sector of a cross section of the pulmonary artery having a central angle between 20 degrees and 180 degrees.

22. A method for selectively targeting nerve tissue, comprising:

introducing a catheter comprising one or more ultrasonic transceivers to a pulmonary artery lumen;

configuring an operating console of said catheter to activate said catheter to selectively damage nerves that are not coated by myelin, by emitting a field of unfocused ultrasound energy;

producing a temperature profile ranging between 47-57 degrees C. in said nerves by said catheter by emitting said field of unfocused ultrasound energy at frequency, intensity and duration selected to selectively thermally damage nerves not coated by myelin, and not to substantially damage nerves coated by myelin, and without causing bronchus constriction;

measuring a body lumen diameter while emitting the field of unfocused ultrasound energy; and modifying at least one of said frequency, intensity and duration of said ultrasound energy, in accordance with the body lumen diameter, to thermally damage the nerves not coated by myelin while not damaging the non-targeted tissue.

\* \* \* \* \*